(12) United States Patent
Hamanaka et al.

(10) Patent No.: US 6,777,404 B2
(45) Date of Patent: Aug. 17, 2004

(54) USE OF CORTICOTROPIN RELEASING FACTOR ANTAGONISTS AND RELATED COMPOSITIONS

(75) Inventors: Ernest S. Hamanaka, Gales Ferry, CT (US); Yuhpyng Liang Chen, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/413,879

(22) Filed: Apr. 15, 2003

(65) Prior Publication Data

US 2003/0199527 A1 Oct. 23, 2003

Related U.S. Application Data

(62) Division of application No. 09/696,822, filed on Oct. 26, 2000, now Pat. No. 6,589,947.
(60) Provisional application No. 60/162,340, filed on Oct. 29, 1999.

(51) Int. Cl.$^7$ ...................... A61K 31/33; C07D 215/00; C07D 265/00; C07D 498/02
(52) U.S. Cl. ..................... 514/183; 514/186; 514/228.8; 514/230.5; 514/299; 514/300; 544/63; 544/88; 544/90; 544/91; 544/95
(58) Field of Search ................................ 514/183, 186, 514/228.8, 300, 230.5, 299; 544/63, 88, 90, 95, 91

(56) References Cited

U.S. PATENT DOCUMENTS

| | | | |
|---|---|---|---|
| 4,605,642 A | 8/1986 | Rivier et al. .................. 514/12 |
| 5,063,245 A | 11/1991 | Abreu et al. ................. 514/404 |
| 5,962,479 A | 10/1999 | Chen .......................... 514/348 |

FOREIGN PATENT DOCUMENTS

| | | | |
|---|---|---|---|
| EP | 773023 | * 5/1997 | |
| EP | 0773023 | 5/1997 | ......... A61K/31/435 |
| EP | 0778277 | 6/1997 | ......... C07D/487/04 |
| EP | 0764166 | 9/2000 | ......... C07D/487/04 |
| WO | WO9413676 | 6/1994 | ......... C07D/487/04 |
| WO | WO9413677 | 6/1994 | ......... C07D/487/04 |
| WO | 951506 | * 4/1995 | |
| WO | WO9510506 | 4/1995 | ......... C07D/239/42 |
| WO | WO9533750 | 12/1995 | ......... C07D/487/04 |
| WO | WO9534563 | 12/1995 | ......... C07D/471/04 |
| WO | WO9700868 | 1/1997 | ......... C07D/277/42 |
| WO | WO9725042 | 7/1997 | .......... A61K/31/42 |
| WO | WO9729109 | 8/1997 | ......... C07D/487/04 |
| WO | WO9729110 | 8/1997 | ......... C07D/495/04 |
| WO | WO9805661 | 2/1998 | ......... C07D/471/04 |
| WO | 9808846 | * 3/1998 | |
| WO | WO9808846 | 3/1998 | ......... C07D/471/04 |
| WO | WO9808847 | 3/1998 | ......... C07D/487/04 |
| WO | WO9917761 | 4/1999 | .......... A61K/31/05 |

OTHER PUBLICATIONS

Coyle et al, Science vol. 214, 1184–1190(1983).*
Charmandari et al,PubMed Abstract12649570, also cited as Horm. Res.,59/4, 161–79(2003).*
Tsigos et al, PubMed Abstract 12377295, also cited as J. Psychosom. Res., 53/4, 865–71(2002).*
Ducolett et al, PubMed Abstract 12787849, also cited as Prog. Neuropsychopharmacol. Biol. Psychiatry, 27/4, 625–31(2003).*
"CRF Receptors:Inhibitors, Subtypes, . . . Roel in CN Sys.";Current Ph. Design,1, 305–16(1995).*
M. Hanefeld, Atherosclerosis X, Elsevier Science B.V., pp. 520–524, 1995, "The plurimetabolic syndrome and mortality: the diabetes intervention study (DIS)".
B. R. Walker, Endocrine Research, 22(4), 701–708 (1996), "Abnormal Glucocorticoid Activity in Subjects With Risk Factors for Cardiovascular Disease".
D. N. Brindley, et al., Pennington Cent. Nutr. Ser. 5(1996), (Molecular and Genetic Aspects of Obesity), pp. 340–352.
D. N. Brindley, et al., Progress in Obesity Research: 7, pp. 505–510, (1996), "Role of fatty acids, glucocorticoids and insulin resistance in the dyslipidaemia of the metabolic syndrome".
B. R. Walker, et al., Hypertension, 1998; 3.891–895, "Increased Glucocorticoid Activity in Men With Cardiovascular Risk Factors".
S. W. Turner, et al., J. Hypertension, 16:593–600 (1998), Adrenocorticotrophin dose–response relationships in the rat: haemodynamic, metabolic and hormonal effects.
T. E. Christos, et al, Exp. Opin. Ther. Patents (1998) 8(2):143–152, Corticotrophin–releasing factor receptor antagonists.
D. T. Chalmers, et al., Trends in Pharmacological Sciences, Apr. 1996, pp. 166–172, "Corticotrophin–releasing factor receptors: from molecular biology to drug design".
M. J. Owens, et al., Pharm. Rev., 43:425–473, 1991, "Physiology and Pharmacology of Corticotropin–releasing Factor.".
Goddman & Gilman's The Pharmacological Basis of Therapeutics, (1996), pp. 1466–1470, 9$^{th}$ edition; McGraw–Hill.
Stedman's Medical Dictionary, 24$^{th}$ Edition, 1982, p. 1386, definition of "Cushing's syndrome".

* cited by examiner

Primary Examiner—Mukund Shah
Assistant Examiner—Sudhaker B. Patel
(74) Attorney, Agent, or Firm—Peter C. Richardson; Paul H. Ginsburg; Andrea E. Dorigo

(57) ABSTRACT

The present invention relates to compositions and methods of achieving a therapeutic effect including, the treatment or prevention of Syndrome X in an animal, preferably a mammal including a human subject or a companion animal, using a corticotropin releasing factor (CRF) antagonist alone or together with a glucocorticoid receptor antagonist.

2 Claims, No Drawings

USE OF CORTICOTROPIN RELEASING FACTOR ANTAGONISTS AND RELATED COMPOSITIONS

CROSS REFERENCE TO RELATED APPLICATION

This application is a divisional and claims benefit of priority from United States nonprovisional patent application Ser. No. 09/696,822, filed Oct. 26, 2000 now U.S. Pat. No. 6,589,947, which claims benefit of priority from United States provisional patent application no. 60/162,340, filed Oct. 29, 1999.

BACKGROUND OF THE INVENTION

The present invention relates to compositions and methods of achieving a therapeutic effect, including the treatment or prevention of Syndrome X, in an animal, preferably a mammal, including a human subject, and a companion animal, using a corticotropin releasing factor (CRF) antagonist alone or together with a glucocorticoid receptor (GR) antagonist.

Syndrome X, also known as metabolic syndrome, plurimetabolic syndrome or insulin resistance syndrome, encompasses a complex of disturbances of carbohydrate and fat metabolism characterized by obesity, dyslipoproteinemia (low HDL and high LDL, VLDL and triglycerides), hyperinsulinemia, insulin resistance, glucose intolerance and hypertension (Atherosclerosis X, F. P. Woodford, J. Davignon, A. Sniderman (Eds.), Elsevier Science BV, Amsterdam (1995): 520–524.). Syndrome X is associated with an elevated risk for cardiovascular disease.

There are striking similarities between Cushing's disease and Syndrome X, both being characterized by visceral obesity, hypertension, insulin resistance, glucose intolerance and hyperlipidemia (Endocrine Research, 22(4), 701–708 (1996)). Cushing's disease is caused by hypersecretion of cortisol, the most important human glucocorticoid, by the adrenal cortex. Cortisol is known to cause visceral fat accumulation and insulin resistance (Pennington Cent. Nutr. Ser. (1996), 5 (Molecular and Genetic Aspects of Obesity), 340–352; Nutrition, 13:795–803 (1997); and Prog. Obes. Res., 7:505–510 (1996)). Cortisol promotes hepatic gluconeogenesis and glycogen deposition and increases blood glucose levels. Cortisol also increases the sensitivity of adipose tissue to lipolytic hormones, elevating fatty acid levels and thereby stimulating triglyceride synthesis and VLDL (very low density lipoprotein) secretion. The VLDL is converted to VLDL remnants or LDL (low density lipoprotein) which are largely taken up by the liver via the LDL receptors, resulting in down-regulation of the LDL receptor and consequently hypertriglyceridemia and hyperapobetalipoproteinemia. Abnormalities of glucocorticoid secretion and sensitivity in men have been shown to be associated with hypertension and insulin resistance (Endocrine Research, 22(4), 701–708 (1996); and Hypertension, 1998;31:891–895). Hypersecretion of cortisol is the result of excessive secretion of ACTH (adrenocorticotropic hormone). Administration of ACTH has been shown to increase blood pressure in animals (J. Hypertension, 16:593–600 (1998)). The secretion of ACTH is controlled by the releasing hormone, corticotropin releasing factor (CRF or CRH). Thus, a CRF (CRH) antagonist, by decreasing ACTH secretion, will amelioralte the hypersecretion of glucocorticoids and thereby be of therapeutic benefit in the treatment of Syndrome X.

In addition, the levels of glucocorticoids present in the body are primarily, but not solely, determined by the concentration of CRF, so the use of a combination of a CRF antagonist and a GR antagonist will be of greater therapeutic benefit in the treatment of Syndrome X than the use of a CRF antagonist alone.

International Patent Application Publication No. WO 97/25042, published Jul. 17, 1997, discloses methods for the treatment and/or prophylaxis of Syndrome X by the administration of an agonist of PPARα and PPARγ, or a pharmaceutically acceptable derivative thereof, to a human or non-human animal in need of such treatment.

International Patent Application Publication No. WO 99/17761, published Apr. 15, 1999, discloses the use of nordihydroguaiaretic acid to treat or ameliorate the characteristic manifestations of Syndrome X in a non-diabetic animal with normal serum glucose levels.

CRF antagonists are disclosed in U.S. Pat. Nos. 4,605,642 and 5,063,245. They are also disclosed in International patent publications WO 95/33750; WO 95/34563; WO 94/13661; WO 94/13644; WO 94/13643; WO 94/13676; WO 94/13677; WO 95/33727; WO 98/05661; WO 98/08847; WO 98/08846; and European patent publications EP 778277 and EP 773023. CRF antagonists are also disclosed in the following patent publications: EP 576350; EP 659747; EP 812831; WO 95/10506; WO 96/35689; WO 96/39400; WO 97/00868; WO 97/14684; WO 97/29109; WO 97/29110; WO 97/35539; WO 97/35580; WO 97/35846; WO 97/44038; WO 97/45421; WO98/03510; WO 98/08821; WO 98/11075; WO 98/15543; WO 98/21200; WO 98/27066; WO 98/29397; WO 98/29413; WO 98/42699; WO 98/35967; WO 98/42706; WO 98/45295; WO 98/47874; WO 98/47903; WO 98/51312; WO 99/01454; WO 99/01439; WO 99/10350; WO 99/12908; WO 99/00373; WO 99/38868; WO 99/51597; WO 99/51599; WO 99/40089; WO 99/51598; and WO 99/51600. They are also disclosed in U.S. Pat. Nos. 5,109,111; 5,132,111; 5,245,009; 5,464,847; 5,493,006; 5,510,458; 5,644,057; 5,663,292; 5,668,145; 5,705,646; 5,712,303; and 5,723,608. An overview of the patent literature on CRF antagonists is provided in T. E. Christos and A. Arvanitis, Exp. Opin. Ther. Patents (1998) 8(2):143–152.

The importance of CRF antagonists is set out in the literature, e.g., P. Black, Scientific American: "Science & Medicine," 1995, 2:16–25; T. Lovenberg, et al., Current Pharmaceutical Design, 1995, 1: 305–316; D. T. Chalmers et al., Trends in Pharmacological Sciences, April 1996, pages 166–172; and U.S. Pat. No. 5,063,245. An outline of the activities possessed by CRF antagonists is found in M. J. Owens et al., 1991, Pharm. Rev., 43:425–473. CRF antagonists are described in the art as being effective in the treatment of stress-related illnesses, mood disorders such as depression, major depressive disorder, single episode depression, recurrent depression, child abuse induced depression, postpartum depression, dysthemia, bipolar disorders, and cyclothymia; chronic fatigue syndrome; eating disorders such as anorexia and bulimia nervosa; generalized anxiety disorder; panic disorder; phobias; obsessive-compulsive disorder; post-traumatic stress disorder; pain perception such as fibromyalgia; headache; gastrointestinal diseases; hemorrhagic stress; ulcers; stress-induced psychotic episodes; fever; diarrhea; post-operative ileus; colonic hypersensitivity; irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimer's disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiuretic hormone; obesity; chemical dependencies and addictions; drug and alcohol withdrawal symptoms; infertility; cancer; muscular spasms; urinary incontinence; hypoglycemia and immune dysfunctions including stress induced immune dysfunctions, immune suppression and human immunodeficiency virus infections; and stress-induced infections in humans and animals.

GR antagonists are disclosed in the following references: International patent application PCT/IB00/00366, filed Mar. 27, 2000, and assigned to the assignee hereof, which published as International patent publication WO 00/66522; International patent publications WO 99/41256 and WO 99/41257; U.S. Pat. No. 5,696,127; European patent publication 188396; European patent publication 683172; International patent publication WO 98/26783; International patent publication WO 98/27986; International patent publication WO 98/31702; European patent publication 903146; and International patent publications WO 99/41256 and WO 99/41257.

GR modulators (e.g., agonists, partial agonists, antagonists and partial antagonists) can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty.

All of the hereinabove and below cited U.S. patents, U.S. patent applications, published European patent applications and published PCT international patent applications are incorporated herein by reference in their entirety.

SUMMARY OF THE INVENTION

The present invention provides methods of treating or preventing Syndrome X in an animal which comprises administering to said animal an amount of a corticotropin releasing factor antagonist. More particularly, the present invention provides these methods wherein a therapeutically effective amount of a corticotropin releasing factor antagonist is administered. More particularly, the present invention provides these methods wherein the corticotropin releasing factor antagonist is a compound of a particular generic formula as described below.

Also, the present invention provides methods of treating or preventing Syndrome X in an animal which comprises administering to said animal an amount of a corticotropin releasing factor antagonist and an amount of a glucocorticoid receptor antagonist; wherein the amount of the corticotropin releasing factor antagonist and the amount of the glucocorticoid receptor antagonist result in a therapeutic effect. More particularly, the present invention provides these methods wherein the corticotrophin releasing factor antagonist is a compound of a particular generic formula as described below. More particularly, the present invention provides these methods wherein the glucocorticoid receptor antagonist is a compound of formula IA wherein the variables are as defined below.

Also, the present invention provides pharmaceutical compositions for treating or preventing Syndrome X which comprises an amount of a corticotropin releasing factor antagonist and a pharmaceutically acceptable vehicle, carrier or diluent. More particularly, the present invention provides these compositions which comprise a therapeutically effective amount of a corticotropin releasing factor antagonist. More particularly, the present invention provides these compositions wherein the corticotropin releasing factor is a compound of a particular generic formula as described below.

Also, the present invention provides pharmaceutical compositions for treating or preventing Syndrome X which comprises an amount of a corticotropin releasing factor antagonist, an amount of a glucocorticoid receptor antagonist and a pharmaceutically acceptable vehicle, carrier or diluent; wherein the amount of the corticotropin releasing factor antagonist and the amount of the glucocorticoid receptor antagonist result in a therapeutic effect. More particularly, the present invention provides these compositions wherein the corticotrophin releasing factor antagonist is a compound of a particular generic formula as described below. More particularly, the present invention provides these compositions wherein the glucocorticoid receptor antagonist is a compound of formula IA wherein the variables are as defined below.

Also, the present invention provides kits which comprise an amount of a corticotropin releasing factor antagonist and a pharmaceutically acceptable vehicle, carrier or diluent in a first unit dosage form; an amount of a glucocorticoid receptor antagonist and a pharmaceutically acceptable vehicle, carrier or diluent in a second unit dosage form; and a container for containing said first and second dosage forms; wherein the amount of the corticotropin releasing factor antagonist and the amount of the glucocorticoid receptor antagonist result in a therapeutic effect. More particularly, the present invention provides these kits wherein the corticotrophin releasing factor antagonist is a compound of a particular generic formula as described below. More particularly, the present invention provides these kits wherein the glucocorticoid receptor antagonist is a compound of formula IA wherein the variables are as defined below.

The present invention relates to compositions and methods useful in achieving therapeutic effects, such as the treatment or prevention of Syndrome X, which compositions preferably comprise a corticotropin releasing factor (CRF) antagonist alone or in combination with a glucocorticoid receptor (GR) antagonist, and a pharmaceutically acceptable carrier, vehicle or diluent, and which methods preferably comprise administering to an animal, preferably a mammal including a human subject or a companion mammal in need of such treatment, a CRF antagonist and a GR antagonist.

The terms "treating" and "treatment," as used herein, unless otherwise indicated, include, inter alia, palliative and curative treatment of any disorder enumerated within the methods of the present invention.

The terms "preventing," "prevention" and "prophylaxis," as used herein, unless otherwise indicated, include the inhibition or preclusion of the development of any disorder enumerated within the methods of the present invention.

DETAILED DESCRIPTION OF THE INVENTION

Syndrome X is the syndrome characterized by an initial insulin resistant state, generating hyperinsulinaemia, dyslipidaemia and impaired glucose tolerance, which can progress to non-insulin dependent diabetes mellitus (Type II diabetes), characterized by hyperglycaemia and which then further progresses to diabetic complications.

CRF antagonists alone or together with GR antagonists are effective for the treatment and/or prophylaxis of Syndrome X and the resulting complications thereof. These compounds are therefore considered to be useful for the treatment and/or prophylaxis of any combination of the following list of disorders associated with Syndrome X and the resulting complications thereof, including, for example, insulin resistance, diabetes, more particularly non-insulin dependent diabetes mellitus (Type II diabetes), and the complications associated with diabetes, dyslipidaemia, hyperinsulinaemia, hyperglycaemia, atherosclerosis, hypertension, cardiovascular disease and obesity. This list is for purposes of illustration only and is not intended to limit the scope of the present invention.

The complications associated with diabetes include, for example, cardiovascular disease, especially atherosclerosis, retinopathy, neuropathy and renal disease including diabetic nephropathy, glomerulonephritis, glomerular sclerosis, nephrotic syndrome, hypertensive nephrosclerosis and end stage renal disease.

The term corticotropin releasing factor (CRF) antagonist refers to a compound having the ability to inhibit or reverse the deleterious effects of the presence of CRF. It is well known that CRF profoundly stimulates the pituitary-adrenalcortical axis and, in dysfunctional states, initiates behavioral, physiological and endocrine responses that are essentially identical to those observed when animals, including humans and companion animals, are subjected to a stressful environment. Therefore, CRF antagonists are known to have utility, inter alia, in the amelioration of certain stress-induced conditions including memory loss, mood alteration, depression, hypertension and the like.

Any CRF antagonist can be used to practice the present invention, including those that are described in U.S. Pat. Nos. 4,605,642 and 5,063,245; International patent publications WO 95/33750; WO 95/34563; WO 94/13661; WO 94/13644; WO 94/13643; WO 94/13676; WO94/13677; WO 95/33727; WO 98/05661; WO 98/08847; and WO 98/08846; and European patent publications EP 778277; and EP 773023. They also include those of the following patent publications: EP 576350; EP 659747; EP 812831; WO 95/10506; WO 96/35689; WO 96/39400; WO 97/00868; WO 97/14684; WO 97/29109; WO 97/29110; WO 97/35539; WO 97/35580; WO 97/35846; WO 97/44038; WO 97/45421; WO 98/03510; WO 98/08821; WO 98/11075; WO 98/15543; WO 98/21200; WO 98/27066; WO 98/29397; WO 98/29413; WO 98/42699; WO 98/35967; WO 98/42706; WO 98/45295; WO 98/47874; WO 98/47903; WO 98/51312; WO 99/01454; WO99/01439; WO99/10350; WO99/12908; WO99/00373; WO 99/38868; WO 99/51597; WO 99/51599; WO 99/40089; WO 99/51598; and WO 99/51600. They are also disclosed in U.S. Pat. Nos. 5,109,111; 5,132,111; 5,245,009; 5,464,847; 5,493,006; 5,510,458; 5,644,057; 5,663,292; 5,668,145; 5,705,646; 5,712,303; and 5,723,608. Additional information relating to preparing certain of these compounds is provided in WO 96/39388, which describes the production of certain intermediates. As noted above, the texts of all of these publications are incorporated by reference herein in their entireties.

Following are listed particular examples of CRF antagonists that may be used in practicing the invention. It is understood that in the generic formulae employed below, the variables employed, e.g., "A", "B", "$R_1$", "$R_2$", etc. have the meanings attributed to them only in the particular Roman numeral section in which they are found. Thus, the meaning attributed, for example, to "$R^1$" is different for the structures in section I and the structures of the other sections.

I. For example, the CRF antagonist may be of the following formula, described in WO 94/13677:

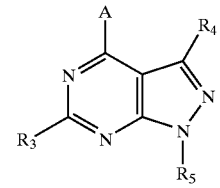

and the pharmaceutically acceptable acid addition salts thereof, wherein

A is $NR_1R_2$, $CR_1R_2R_{11}$, or $C(=CR_1R_{12})R_2$, $NHCR_1R_2R_{11}$, $OCR_1R_2R_{11}$, $SCR_1R_2R_{11}$, $NHNR_1R_2$, $CR_2R_{11}NHR_1$, $CR_2R_{11}OR_1$, $CR_2R_{11}SR_1$ or $C(O)R_2$;

$R_1$ is hydrogen, or $C_1-C_6$ alkyl which may be substituted by one or two substituents $R_6$ independently selected from the group consisting of hydroxy, fluoro, chloro, bromo, iodo, $C_1-C_6$ alkoxy, O—C(O)—($C_1-C_6$ alkyl), O—C(O)—N($C_1-C_4$ alkyl)($C_1-C_2$ alkyl); amino, NH($C_1-C_4$ alkyl), S($C_1-C_6$ alkyl), OC(O)NH ($C_1-C_4$alkyl), N($C_1-C_2$ alkyl)C(O)($C_1-C_4$ alkyl), NHC(O)($C_1-C_4$ alkyl), COOH, CO($C_1-C_4$ alkyl), C(O)NH($C_1-C_4$ alkyl, C(O)N($C_1-C_4$ alkyl)($C_1-C_2$ alkyl), SH, CN, $NO_2$, SO($C_1-C_4$ alkyl); $SO_2$($C_1-C_4$ alkyl), $SO_2NH$($C_1-C_4$ alkyl), $SO_2N$($C_1-C_4$ alkyl) ($C_1-C_2$ alkyl), and said $C_1-C_6$ alkyl may have one or two double or triple bonds;

$R_2$ is $C_1-C_{12}$ alkyl, aryl or ($C_1-C_{10}$ alkylene)aryl wherein said aryl is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, oxazolyl, or benzoxazolyl; 3- to 8-membered cycloalkyl or ($C_1-C_6$ alkylene) cycloalkyl, wherein said cycloalkyl may have one or two of O, S or N—Z, wherein Z is hydrogen, substituted, independently, for one or two carbons of said cycloalkyl, $C_1-C_4$ alkyl, benzyl or $C_1-C_4$ alkanoyl, wherein $R^2$ may be substituted independently by from one to three of chloro, fluoro, or $C_1-C_4$ alkyl, or one of hydroxy, bromo, iodo, $C_1-C_6$ alkoxy, OC(O)($C_1-C_6$ alkyl), O—C—N($C_1-C_4$ alkyl)($C_1-C_2$ alkyl), S($C_1-C_6$ alkyl), $NH_2$, NH($C_1-C_2$ alkyl), N($C_1-C_4$ alkyl) C(O) ($C_1-C_4$ alkyl), NHC(O)($C_1-C_4$ alkyl), COOH, C(O)O ($C_1-C_4$ alkyl), C(O)NH($C_1-C_4$ alkyl), C(O)N($C_1-C_4$ alkyl)($C_1-C_2$ alkyl), SH, CN, $NO_2$, SO($C_1-C_4$ alkyl), $SO_2$($C_1-C_4$ alkyl), $SO_2NH$($C_1-C_4$ alkyl), $SO_2N$($C_1-C_2$ alkyl), and wherein said $C_1-C_{12}$ alkyl or $C_1-C_{10}$ alkylene may have one to three double or triple bonds; or $NR_1R_2$ or $CR_1R_2R_{11}$ may form a 4- to 8-membered ring optionally having one or two double bonds or one or two of O, S or N—Z wherein Z is hydrogen, $C_1-C_4$ alkyl, benzyl, or $C_1-C_4$ alkanoyl;

$R_3$ is hydrogen, $C_1$–$C_6$ alkyl, fluoro, chloro, bromo, iodo, hydroxy, amino, O($C_1$–$C_6$ alkyl), NH($C_1$–$C_6$ alkyl), N($C_1$–$C_4$ alkyl)($C_1$–$C_2$ alkyl), SH, S($C_1$–$C_4$ alkyl), SO($C_1$–$C_4$ alkyl), or $SO_2$($C_1$–$C_4$ alkyl), wherein said $C_1$–$C_4$ alkyl and $C_1$–$C_6$ alkyl may have one or two double or triple bonds and may be substituted by from 1 to 3 $R_7$ substituents independently selected from the group consisting of hydroxy, amino, $C_1$–$C_3$ alkoxy, dimethylamino, diethylamino, methylamino, ethylamino, NHC(O)$CH_3$, fluoro, chloro or $C_1$–$C_3$ thioalkyl;

$R_4$ is hydrogen, $C_1$–$C_6$ alkyl, fluoro, chloro, bromo, iodo, $C_1$–$C_6$ alkoxy, amino, NH($C_1$–$C_6$ alkyl), N($C_1$–$C_6$ alkyl) ($C_1$–$C_2$ alkyl), $SO_n$($C_1$–$C_6$ alkyl), wherein n is 0, 1 or 2, cyano, hydroxy, carboxy, or amido, wherein said $C_1$–$C_6$ alkyls may be substituted by one to three of hydroxy, amino, carboxy, amido, NHC(O)($C_1$–$C_4$ alkyl), NH($C_1$–$C_4$ alkyl), N($C_1$–$C_4$ alkyl)($C_1$–$C_2$ alkyl), C(O)O($C_1$–$C_4$ alkyl), $C_1$–$C_3$ alkoxy, $C_1$–$C_3$ thioalkyl, fluoro, bromo, chloro, iodo, cyano or nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, pyrrolopyridyl benzoxazolyl, oxazolyl, pyrrolidinyl, thiazolidinyl, piperazinyl, piperidinyl, or tetrazolyl, wherein each one of the above groups may be substituted independently by from one to three of fluoro, chloro, bromo, formyl, $C_1$–$C_6$ alkyl, $C_1$–$C_6$ alkoxy or trifluoromethyl, or one of hydroxy, iodo, cyano, nitro, amino, cyclopropyl, NH($C_1$–$C_4$ alkyl), N($C_1$–$C_4$ alkyl)($C_1$–$C_2$ alkyl), COO ($C_1$–$C_4$ alkyl), CO($C_1$–$C_4$ alkyl), $SO_2$NH($C_1$–$C_4$ alkyl), $SO_2$N($C_1$–$C_4$ alkyl)($C_1$–$C_2$ alkyl), $SO_2NH_2$, $NHSO_2$($C_1$–$C_4$ alkyl), S($C_1$–$C_6$ alkyl), $SO_2$($C_1$–$C_6$ alkyl), wherein said $C_1$–$C_4$ alkyl and $C_1$–$C_6$ alkyl may have one double or triple bond and may be substituted by one or two of fluoro, chloro, hydroxy, amino, methylamino, dimethylamino or acetyl; with the proviso that $R_5$ is not unsubstituted phenyl;

$R_{11}$ is hydrogen, hydroxy, fluoro, chloro, COO($C_1$–$C_2$ alkyl), cyano, or CO($C_1$–$C_2$ alkyl); and $R_{12}$ is hydrogen or $C_1$–$C_4$ alkyl;

(a) A is not straight chain $C_1$–$C_{12}$ alkyl;

(b) when $R_3$ is hydrogen, A is benzyl or phenethyl, and $R_4$ is fluoro, chloro, bromo or iodo, then $R_5$ is not 5'-deoxy-ribofuranosyl or 5'-amino-5'-deoxy-ribofuranosyl; and (c) when $R^5$ is phenyl, said phenyl is substituted by two or three substituents.

II. The invention also relates to use of a CRF antagonist of the following formula, described in WO 94/13676:

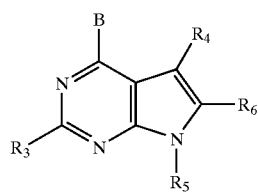

and the pharmaceutically acceptable acid addition salts thereof, wherein

B is $NR_1R_2$, $CR_1R_2R_{11}$, C(=$CR_2R_{12}$)$R_1$, $NHR_1R_2R_{11}$, $OCR_1R_2R_{11}$, $SCR_1R_2R_{11}$, $NHNR_1R_2$, $CR_2R_{11}NHR_1$, $CR_2R_{11}OR_1$, $CR_2R_{11}SR_1$, or C(O)$R_2$;

$R_1$ is hydrogen, or $C_1$–$C_6$ alkyl which may be substituted by one or two substituents $R_7$ independently selected from the group consisting of hydroxy, fluoro, chloro, bromo, iodo, $C_1$–$C_8$ alkoxy, O—C(=O)—($C_1$–$C_6$ alkyl), O—C(=O)NH($C_1$–$C_4$ alkyl), O—C(=O)—N ($C_1$–$C_4$ alkyl)($C_1$–$C_2$ alkyl), amino, NH($C_1$–$C_4$ alkyl), N($C_1$–$C_2$ alkyl)($C_1$–$C_4$ alkyl), S($C_1$–$C_6$ alkyl), N($C_1$–$C_4$alkyl)C(=O)($C_1$–$C_4$ alkyl), NH($C_1$–$C_4$ alkyl), COOH, C(=O)O($C_1$–$C_4$ alkyl), C(=O)NH ($C_1$–$C_4$ alkyl), C(=O)N($C_1$–$C_4$ alkyl)($C_1$–$C_2$ alkyl), SH, CN, $NO_2$, SO($C_1$–$C_4$ alkyl), $SO_2$($C_1$–$C_4$ alkyl), $SO_2$NH($C_1$–$C_4$ alkyl), $SO_2$N($C_1$–$C_4$ alkyl) $C_1$–$C_2$ alkyl) and said $C_1$–$C_6$ alkyl may contain one or two double or triple bonds;

$R_2$ is $C_1$–$C_{12}$ alkyl, aryl or ($C_1$–$C_{10}$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl or ($C_1$–$C_6$ alkylene) cycloalkyl, wherein said cycloalkyl may contain one or two of O, S or N—Z wherein Z is hydrogen, $C_1$–$C_4$ alkyl, benzyl or $C_1$–$C_4$ alkanoyl, wherein $R_2$ may be substituted independently by from one to three of chloro, fluoro, or $C_1$–$C_4$ alkyl, or one of hydroxy, bromo, iodo, $C_1$–$C_6$ alkoxy, O—C(=O)—($C_1$–$C_6$ alkyl), O—C—N($C_1$–$C_4$ alkyl)($C_1$–$C_2$ alkyl), S($C_1$–$C_6$ alkyl), $NH_2$, NH($C_1$–$C_2$ alkyl), N($C_1$–$C_2$ alkyl) ($C_1$–$C_4$ alkyl), N($C_1$–$C_4$)—C(=O)($C_1$–$C_4$ alkyl), NHC(=O) ($C_1$–$C_4$), COOH, C(=O)O($C_1$–$C_4$ alkyl), C(=O)NH ($C_1$–$C_4$ alkyl), C(=O)N($C_1$–$C_4$ alkyl)($C_1$–$C_2$ alkyl), SH, CN, $NO_2$, SO($C_1$–$C_4$ alkyl), $SO_2$($C_1$–$C_4$ alkyl), $SO_2$NH($C_1$–$C_4$ alkyl), $SO_2$N($C_1$–$C_4$ alkyl)($C_1$–$C_4$ alkyl), and wherein said $C_1$–$C_{12}$ alkyl or $C_1$–$C_{10}$ alkylene may contain one to three double or triple bonds; or $NR_1R_2$ or $CR_1R_2R_{11}$ may form a saturated 3- to 8 membered carbocyclic ring of which the 5- to 8-membered ring contain one or two double bonds or one or two of O, S or N—Z wherein Z is hydrogen, $C_1$–$C_4$ alkyl, benzyl or $C_1$–$C_4$ alkanoyl;

$R_3$ is hydrogen, $C_1$–$C_6$ alkyl, fluoro, chloro, bromo, iodo, hydroxy, amino, O($C_1$–$C_6$ alkyl), NH($C_1$–$C_6$ alkyl), N($C_1$–$C_4$ alkyl) ($C_1$–$C_2$ alkyl), SH, S($C_1$–$C_4$ alkyl), SO($C_1$–$C_4$ alkyl), or $SO_2$($C_1$–$C_4$ alkyl), wherein said $C_1$–$C_4$ alkyl and $C_1$–$C_6$ alkyl may contain from one or two double or triple bonds and may be substituted by from 1 to 3 substituents $R_8$ independently selected from the group consisting of hydroxy, amino, $C_1$–$C_3$ alkoxy, dimethylamino, diethylamino, methylamino, ethylamino, $NHCH_3$, fluoro, chloro or $C_1$–$C_3$ thioalkyl;

$R_4$ and $R_6$ are each independently hydrogen, $C_1$–$C_6$ alkyl, fluoro, chloro, bromo, iodo, $C_1$–$C_6$ alkoxy, amino, NH($C_1$–$C_6$ alkyl), N($C_1$–$C_6$ alkyl)($C_1$–$C_2$ alkyl), $SO_n$ ($C_1$–$C_6$ alkyl), wherein n is 0, 1 or 2, cyano, hydroxy, carboxy, or amido, wherein said $C_1$–$C_6$ alkyls may be substituted by one to three of hydroxy, amino, carboxy, amido, NHC(=O)($C_1$–$C_4$ alkyl), NH($C_1$–$C_4$ alkyl), N($C_1$–$C_4$ alkyl)($C_1$–$C_2$ alkyl), C(=O)O($C_1$–$C_4$ alkyl), $C_1$–$C_3$ alkoxy, $C_1$–$C_3$ thioalkyl, fluoro, bromo, chloro, iodo, cyano or nitro;

$R_5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, piperidinyl, piperazinyl, tetrazolyl, or 3- to 8-membered cycloalkyl or 9- to 12-membered bicycloalkyl, optionally containing one to three of O, S or N—Z wherein Z is hydrogen, $C_1$–$C_4$ alkyl, $C_1$–$C_4$ alkanoyl, phenyl or phenylmethyl, wherein each one of the above groups may be substituted independently by from one to four of fluoro, chloro, $C_1$–$C_6$ alkyl, $C_1$–$C_6$ alkoxy or trifluoromethyl, or one of bromo, iodo, cyano, nitro, amino, NH($C_1$–$C_4$ alkyl), N($C_1$–$C_4$)($C_1$–$C_2$ alkyl), COO($C_1$–$C_4$ alkyl), CO($C_1$–$C_4$ alkyl), $SO_2$NH($C_1$–$C_4$ alkyl), $SO_2$N($C_1$–$C_4$ alkyl)($C_1$–$C_2$ alkyl), $SO_2$$NH_2$, $NHSO_2$($C_1$–$C_4$ alkyl), S($C_1$–$C_6$ alkyl), $SO_2$($C_1$–$C_6$ alkyl), wherein said $C_1$–$C_4$ alkyl and $C_1$–$C_6$ alkyl may be substituted by one or two of fluoro, chloro, hydroxy, amino, methylamino, dimethylamino or acetyl; with the proviso that $R_5$ is not unsubstituted phenyl;

$R_{11}$ is hydrogen, hydroxy, fluoro, chloro, COO($C_1$–$C_2$ alkyl), cyano, or CO($C_1$–$C_2$ alkyl); and $R_{12}$ is hydrogen or $C_1$–$C_4$ alkyl; with the proviso that (1) when $R_5$ is 4-bromophenyl, $R_3$ is hydrogen, and $R_4$ and $R_6$ are methyl, then B is not methylamino or ethyl, and (2) when $R_5$ is 4-bromophenyl, and $R_3$, $R_4$ and $R_6$ are methyl, then B is not 2-hydroxyethylamino.

III. It is also possible to employ a CRF antagonist that has a structure selected from the group shown below, and pharmaceutically acceptable salts and esters thereof, as described in WO 95/33750:

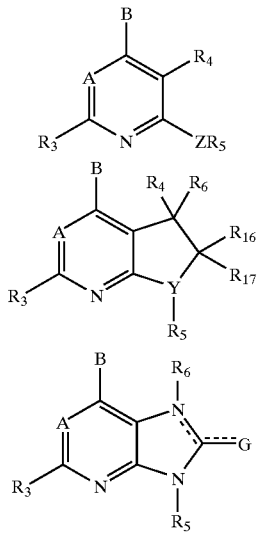

or a pharmaceutically acceptable salt thereof, wherein
the dashed lines represent optional double bonds;

A is $CR_7$ or N;

B is $NR_1R_2$, $CR_1R_2R_{11}$, C(=$CR_2R_{12}$)$R_1$, $NHCHR_1R_2$, $OCHR_1R_2$, $SCHR_1R_2$, $CHR_2OR_{12}$, $CHR_2SR_{12}$, C(S)$R_2$ or C(O)$R_2$;

G is oxygen, sulfur, NH, $NH_3$, hydrogen, methoxy, ethoxy, trifluoromethoxy, methyl, ethyl, thiomethoxy, $NH_2$, $NHCH_3$, $N(CH_3)_2$ or trifluromethyl;

Y is CH or N;

Z is NH, O, S, N ($C_1$–$C_2$ alkyl), or $CR_{13}R_{14}$, wherein $R_{13}$ and $R_{14}$ are each independently hydrogen, trifluoromethyl, or $C_1$–$C_4$ alkyl, or one of $R_{13}$ and $R_{14}$ may be cyano, chloro, bromo, iodo, fluoro, hydroxy, O($C_1$–$C_2$ alkyl), amino, NH($C_1$–$C_2$ alkyl), or $CR_{13}R_{14}$ may be C=O or cyclopropyl;

$R_1$ is $C_1$–$C_6$ alkyl which may be substituted by one or two substituents $R_8$ independently selected from the group consisting of hydroxy, fluoro, chloro, bromo, iodo, $C_1$–$C_4$ alkoxy, O—CO—($C_1$–$C_4$ alkyl), O—CO—NH ($C_1$–$C_4$ alkyl), O—CO—N($C_1$–$C_4$ alkyl)($C_1$–$C_2$ alkyl), NH($C_1$–$C_4$ alkyl), N($C_1$–$C_2$ alkyl)($C_1$–$C_4$ alkyl), S($C_1$–$C_4$ alkyl), N($C_1$–$C_4$alkyl)CO($C_1$–$C_4$ alkyl), NHCO($C_1$–$C_4$ alkyl), COO($C_1$–$C_4$ alkyl), CONH ($C_1$–$C_4$ alkyl), CON($C_1$–$C_4$ alkyl)($C_1$–$C_2$ alkyl), S($C_1$–$C_4$ alkyl), CN, $NO_2$, SO($C_1$–$C_4$ alkyl), $SO_2$ ($C_1$–$C_4$ alkyl), and said $C_1$–$C_6$ alkyl or $C_1$–$C_4$ alkyl may contain one double or triple bond;

$R_2$ is $C_1$–$C_{12}$ alkyl, aryl or ($C_1$–$C_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, or benzoxazolyl; 3- to 8-membered cycloalkyl or ($C_1$–$C_6$ alkylene)cycloalkyl, wherein said cycloalkyl may contain one or two of O, S or N—$R_9$ wherein $R_9$ is hydrogen, or $C_1$–$C_4$ alkyl, wherein the above defined $R_2$ may be substituted independently by from one to three of chloro, fluoro, or $C_1$–$C_4$ alkyl, or one of bromo, iodo, $C_1$–$C_6$ alkoxy, O—CO—($C_1$–$C_6$ alkyl), O—CO—N($C_1$–$C_4$ alkyl)($C_1$–$C_2$ alkyl), S($C_1$–$C_6$ alkyl), CN, $NO_2$, SO($C_1$–$C_4$ alkyl), or $SO_2$($C_1$–$C_4$ alkyl), and wherein said $C_1$–$C_{12}$ alkyl or $C_1$–$C_4$ alkylene may contain one double or triple bond; or $NR_1R_2$ or $CR_1R_2R_{11}$ may form a saturated 5- to 8-membered carbocyclic ring which may contain one or two double bonds or one or two of O or S;

$R_3$ is methyl, ethyl, fluoro, chloro, bromo, iodo, cyano, methoxy, $OCF_3$, methylthio, methylsulfonyl, $CH_2OH$ or $CH_2OCH_3$;

$R_4$ is hydrogen, $C_1$–$C_4$ alkyl, fluoro, chloro, bromo, iodo, $C_1$–$C_4$ alkoxy, amino, nitro, NH($C_1$–$C_4$ alkyl), N($C_1$–$C_4$ alkyl)($C_1$–$C_2$ alkyl), $SO_n$($C_1$–$C_4$ alkyl), wherein n is 0, 1 or 2, cyano, hydroxy, CO($C_1$–$C_4$ alkyl), CHO, or COO($C_1$–$C_4$ alkyl), wherein said $C_1$–$C_4$ alkyl may contain one or two double or triple bonds and may be substituted by one or two of hydroxy, amino, carboxy, $NHCOCH_3$, NH($C_1$–$C_2$ alkyl), N($C_1$–$C_2$ alkyl)$_2$, COO($C_1$–$C_4$ alkyl), CO($C_1$–$C_4$ alkyl), $C_1$–$C_3$ alkoxy, $C_1$–$C_3$ thioalkyl, fluoro, chloro, cyano or nitro;

$R_5$ is phenyl, naphthyl, thienyl, benzothienyl, pyridyl, quinolyl, pyrazinyl, pyrimidyl, furanyl, benzofuranyl, benzothiazolyl, or indolyl, wherein each one of the above groups $R_5$ is substituted independently by from one to three of fluoro, chloro, $C_1$–$C_6$ alkyl, or $C_1$–$C_6$ alkoxy, or one of hydroxy, iodo, bromo, formyl, cyano, nitro, trifluoromethyl, amino, NH($C_1$–$C_4$ alkyl), N($C_1$–$C_6$)($C_1$–$C_2$ alkyl), COOH, COO($C_1$–$C_4$ alkyl), CO($C_1$–$C_4$ alkyl), $SO_2$NH($C_1$–$C_4$ alkyl), $SO_2$N($C_1$–$C_4$ alkyl)($C_1$–$C_2$ alkyl), $SO_2$$NH_2$, $NHSO_2$($C_1$–$C_4$ alkyl), S($C_1$–$C_6$ alkyl), or $SO_2$($C_1$–$C_6$ alkyl), wherein said $C_1$–$C_4$ alkyl and $C_1$–$C_6$ alkyl may be substituted by one or two of fluoro, hydroxy, amino, methylamino, dimethylamino or acetyl;

$R_6$ is hydrogen, or $C_1$–$C_6$ alkyl, wherein said $C_1$–$C_6$ alkyl may be substituted by one hydroxy, methoxy, ethoxy or fluoro;

$R_7$ is hydrogen, $C_1$–$C_4$ alkyl, fluoro, chloro, bromo, iodo, cyano, hydroxy, O($C_1$–$C_4$ alkyl), C(O)($C_1$–$C_4$ alkyl), or C(O)O($C_1$–$C_4$ alkyl), wherein the $C_1$–$C_4$ alkyl groups may be substituted with one hydroxy, chloro or bromo, or one to three fluoro;

$R_{11}$ is hydrogen, hydroxy, fluoro, or methoxy;

$R_{12}$ is hydrogen or $C_1$–$C_4$ alkyl; and $R_{16}$ and $R_{17}$ are each independently hydrogen, hydroxy, methyl, ethyl, methoxy, or ethoxy, except that they are not both methoxy or ethoxy, and $CR_4R_6$ and $CR_{16}R_{17}$ each independently may be C=O.

IV. It also possible to employ a CRF antagonist of the following formula, disclosed in WO 95/34563:

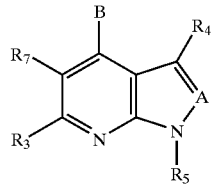

and the pharmaceutically acceptable acid addition salts thereof, wherein

A is N or —$CR_6$;

B is —$NR_1R_2$, —$CR_1R_2R_{11}$, —C(=$CR_2R_{12}$)$R_1$, —$NHCHR_1R_2$, —$OCHR_1R_2$, —$SCHR_1R_2$, —$CHR_2OR_{12}$, —$CHR_2SR_{12}$, —C(S)$R_1$, or —C(O)$R_1$;

$R_1$ is $C_1$–$C_6$ alkyl which may optionally be substituted with one or two substituents independently selected from the group consisting of hydroxy, fluoro, chloro, bromo, iodo, $C_1$–$C_4$ alkoxy, —O—CO—($C_1$–$C_4$ alkyl), —O—CO—NH($C_1$–$C_4$ alkyl), —O—CO—N($C_1$–$C_4$ alkyl)($C_1$–$C_2$ alkyl), —NH($C_1$–$C_4$ alkyl) ($C_1$–$C_2$ alkyl), —S($C_1$–$C_4$ alkyl), —N($C_1$–$C_4$alkyl)CO ($C_1$–$C_4$ alkyl), —NHCO($C_1$–$C_4$ alkyl), —COO($C_1$–$C_4$ alkyl), —CONH($C_1$–$C_4$ alkyl), —CON($C_1$–$C_4$ alkyl) ($C_1$–$C_2$ alkyl), CN, $NO_2$, —SO($C_1$–$C_4$ alkyl), —$SO_2$ ($C_1$–$C_4$ alkyl), and wherein any of the foregoing $C_1$–$C_4$ alkyl and $C_1$–$C_6$ alkyl groups may optionally contain one carbon-carbon double or triple bond;

$R_2$ is $C_1$–$C_{12}$ alkyl, aryl, —($C_1$–$C_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, oxazolyl, or benzoxazolyl; or 3- to 8-membered cycloalkyl or —($C_1$–$C_6$ alkylene)cycloalkyl, wherein one or two of the ring carbons of said cycloalkyl having at least 4 ring members and the cycloalkyl moiety of said —($C_1$–$C_6$ alkylene)cycloalkyl having at least 4 ring members may optionally be replaced by an oxygen or sulfur atom or by N—Z wherein Z is hydrogen; or $C_1$–$C_4$ alkyl, and wherein each of said groups $R_2$ may optionally be substituted with from one to three substituents independently selected from chloro, fluoro, and $C_1$–$C_4$ alkyl, or by one substituent selected from bromo, iodo, $C_1$–$C_6$ alkoxy, —O—CO—($C_1$–$C_6$ alkyl), —S($C_1$–$C_6$ alkyl), —COO($C_1$–$C_4$ alkyl), CN, $NO_2$, —SO($C_1$–$C_4$ alkyl), and —$SO_2$($C_1$–$C_4$ alkyl), and wherein said $C_1$–$C_{12}$ alkyl and the $C_1$–$C_4$ alkylene moiety of said —($C_1$–$C_4$ alkylene)aryl may optionally contain one carbon-carbon double or triple bond;

or —$NR_1R_2$ may form a saturated 5- to 8-membered heterocyclic ring, or —$CHR_1R_2$ may form a saturated 5- to 8-membered carbocyclic ring, wherein each of these rings may optionally contain one or two carbon-carbon double bonds and wherein one or two of the carbon atoms of each of these rings may optionally be replaced with a sulfur or oxygen atom;

$R_3$ is $C_1$–$C_4$ alkyl, fluoro, chloro, bromo, iodo, —$CH_2OH$, —$CH_2OCH_3$, —O($C_1$–$C_3$ alkyl), —S($C_1$–$C_3$ alkyl), or —$SO_2$($C_1$–$C_3$ alkyl), wherein said $C_1$–$C_3$ alkyl may optionally contain one carbon-carbon double or triple bond;

$R_4$ is hydrogen, $C_1$–$C_6$ alkyl, fluoro, chloro, bromo, iodo, $C_1$–$C_4$ alkoxy, amino, —$NHCH_3$, —$N(CH_3)_2$, —$CH_2OH$, —$CH_2OCH_3$, or —$SO_n$($C_1$–$C_4$ alkyl), wherein n is 0, 1 or 2, cyano, hydroxy, —CO($C_1$–$C_4$ alkyl), —CHO, or —COO($C_1$–$C_4$ alkyl) wherein the $C_1$–$C_4$ alkyl moieties in the foregoing $R_4$ groups may optionally contain one carbon-carbon double or triple bond;

$R_5$ is phenyl, naphthyl, thienyl, benzothienyl, pyridyl, pyrimidyl, benzofuranyl, pyrazinyl or benzothiazolyl, wherein each one of said groups $R_5$ may optionally be substituted with from one to three substituents independently selected from fluoro, chloro, $C_1$–$C_6$ alkyl and $C_1$–$C_6$ alkoxy, or by one substituent selected from iodo, hydroxy, bromo, formyl, cyano, nitro, amino, trifluoromethyl, —NH($C_1$–$C_4$ alkyl), —N($C_1$–$C_6$) ($C_1$–$C_2$ alkyl), —COO($C_1$–$C_4$ alkyl), —CO($C_1$–$C_4$ alkyl), —COOH, —$SO_2$($C_1$–$C_4$alkyl), —$SO_2N(C_1$–$C_4$ alkyl)($C_1$–$C_2$ alkyl), —$SO_2NH_2$, —$NHSO_2$($C_1$–$C_4$ alkyl), —S($C_1$–$C_6$ alkyl) and —$SO_2$($C_1$–$C_6$ alkyl), wherein each of said $C_1$–$C_4$ alkyl and $C_1$–$C_6$ alkyl moieties in the foregoing $R^5$ groups may optionally be substituted with one to three fluorine atoms;

$R_6$ is hydrogen, $C_1$–$C_4$ alkyl, fluoro, chloro, bromo, iodo, —$CH_2OH$, —$CH_2OCH_3$, or $C_1$–$C_4$ alkoxy;

$R_7$ is hydrogen, $C_1$–$C_4$ alkyl, fluoro, chloro, bromo, iodo, —O($C_1$–$C_4$ alkyl), cyano, —$CH_2OH$, —$CH_2O$($C_1$–$C_2$ alkyl), —CO($C_1$–$C_2$ alkyl), or —COO($C_1$–$C_2$ alkyl);

$R_{11}$ is hydrogen, hydroxy, fluoro, or methoxy; and $R_{12}$ is hydrogen or $C_1$–$C_4$ alkyl;

with the proviso that when A is N, then: (a) B is not unsubstituted alkyl; (b) $R_5$ is not unsubstituted phenyl or monosubstituted phenyl; and (c) $R_3$ is not unsubstituted alkyl;

or a pharmaceutically acceptable salt of such compound.

V. In another embodiment, the CRF antagonist is of the following formula, disclosed in EP 778277:

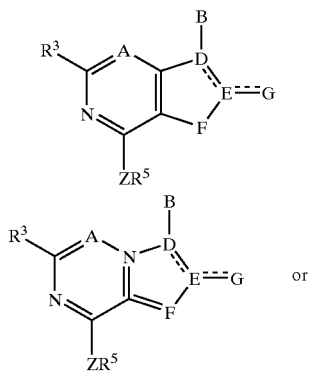

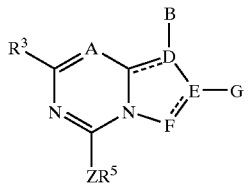

or a pharmaceutically acceptable salt thereof, wherein the dashed lines represent optional double bonds;

A is nitrogen or $CR^7$;

B is $-NR^1R^2$, $-CR^1R^2R^{10}$, $-C(=CR^2R^{11})R^1$, $-NHCR^1R^2R^{10}$, $-OCR^1R^2R^{10}$, $-SCR^1R^2R^{10}$, $-CR^2R^{10}NHR^1$, $-CR^2R^{10}OR^1$, $-CR^2R^{10}SR^1$ or $-COR^2$,

D is nitrogen and is single bonded to all atoms to which it is attached, or D is carbon and is either double bonded to E in formulas I and II or double bonded to the adjacent carbon atom common to both fused rings in formula III, or D is CH and is single bonded to E in formulas I and II;

E is nitrogen, CH or carbon;

F is oxygen, sulfur, $CHR^4$ or $NR^4$ when it is single bonded to E and F is nitrogen or $CR^4$ when it is double bonded to E;

G, when single bonded to E, is hydrogen, $C_1$–$C_4$ alkyl, $-S(C_1$–$C_4$ alkyl), $-O(C_1$–$C_4$ alkyl), $NH_2$, $-NH(C_1$–$C_4$ alkyl) or $-N(C_1$–$C_2$ alkyl)($C_1$–$C_4$ alkyl), wherein each of the $C_1$–$C_4$ alkyl groups of G may optionally be substituted with one hydroxy, $-O(C_1$–$C_2$ alkyl) or fluoro group; G, when double bonded to E, is oxygen, sulfur or NH; and G, when E is nitrogen and double bonded to D or F, is absent;

$R^1$ is hydrogen, $C_1$–$C_6$ alkyl optionally substituted with one or two substituents $R^8$ independently selected from hydroxy, fluoro, chloro, bromo, iodo, $C_1$–$C_4$ alkoxy, $CF_3$, $-C(=O)O-(C_1$–$C_4)$alkyl, $-OC(=O)(C_1$–$C_4$ alkyl), $-OC(=O)N(C_1$–$C_4$ alkyl)($C_1$–$C_2$ alkyl), $-NHCO(C_1$–$C_4$ alkyl), $-COOH$, $-COO(C_1$–$C_4$ alkyl), $-CONH(C_1$–$C_4$ alkyl), $-CON(C_1$–$C_4$ alkyl)($C_1$–$C_2$ alkyl), $-S(C_1$–$C_4$ alkyl), $-CN$, $-NO_2$, $-SO(C_1$–$C_4$ alkyl), $-SO_2(C_1$–$C_4$ alkyl), $-SO_2NH(C_1$–$C_4$ alkyl) and $-SO_2N(C_1$–$C_4$ alkyl)($C_1$–$C_2$ alkyl), wherein each of the $C_1$–$C_4$ alkyl groups in the foregoing $R^1$ groups may optionally contain one or two double or triple bonds;

$R^2$ is $C_1$–$C_{12}$ alkyl which may optionally contain from one to three double or triple bonds, aryl or ($C_1$–$C_4$ alkylene)aryl, wherein said aryl and the aryl moiety of said ($C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3$–$C_8$ cycloalkyl or ($C_1$–$C_6$ alkylene)($C_3$–$C_8$ cycloalkyl), wherein one or two of the carbon atoms of said cycloalkyl and the 5 to 8 membered cycloalkyl moieties of said ($C_1$–$C_6$ alkylene)($C_3$–$C_8$ cycloalkyl) may optionally and independently be replaced by an oxygen or sulfur atom or by $NZ^2$ wherein $Z^2$ is selected from hydrogen, $C_1$–$C_4$ alkyl, benzyl and $C_1$–$C_4$ alkanoyl, and wherein each of the foregoing $R^2$ groups may optionally be substituted with from one to three substituents independently selected from chloro, fluoro, hydroxy and $C_1$–$C_4$ alkyl, or with one substituent selected from bromo, iodo, $C_1$–$C_6$ alkoxy, $-OC(=O)(C_1$–$C_6$ alkyl), $-OC(=O)N(C_1$–$C_4$ alkyl)($C_1$–$C_2$ alkyl), $-S(C_1$–$C_6$ alkyl), amino, $-NH(C_1$–$C_2$ alkyl), $N(C_1$–$C_2$ alkyl), ($C_1$–$C_4$ alkyl),$-N(C_1$–$C_4$ alkyl)—$CO-(C_1$–$C_4$ alkyl), $-NHCO(C_1$–$C_4$ alkyl), $-COOH$, $-COO(C_1$–$C_4$ alkyl), $-CONH(C_1$–$C_4$ alkyl), $-CON(C_1$–$C_4$ alkyl)($C_1$–$C_2$ alkyl), $-SH$, $-CN_1$——$NO_2$, $-SO(C_1$–$C_4$ alkyl), $-SO_2(C_1$–$C_4$ alkyl), $-SO_2NH(C_1$–$C_4$ alkyl) and $SO_2N(C_1$–$C_4$ alkyl)($C_1$–$C_2$ alkyl);

—$NR^1R^2$ or $CR^1R^2R^{10}$ may form a saturated 3 to 8 membered carbocyclic ring which may optionally contain from one to three double bonds and wherein one or two of the ring carbon atoms of such 5 to 8 membered rings may optionally and independently be replaced by an oxygen or sulfur atom or by $NZ^3$ wherein $Z^3$ is hydrogen, $C_1$–$C_4$ alkyl, benzyl or $C_1$–$C_4$ alkanoyl;

$R^3$ is hydrogen, $C_1$–$C_4$ alkyl, $-O(C_1$–$C_4$ alkyl), chloro, fluoro, bromo, iodo, $-CN$, $-S(C_1$–$C_4$ alkyl) or $-SO_2(C_1$–$C_4$ alkyl) wherein each of the ($C_1$–$C_4$ alkyl) moieties in the foregoing $R^3$ groups may optionally be substituted with one substituent $R^9$ selected from hydroxy, fluoro and ($C_1$–$C_2$ alkoxy);

each $R^4$ is, independently, hydrogen, ($C_1$–$C_6$ alkyl), fluoro, chloro, bromo, iodo, hydroxy, cyano, amino, nitro, $-O(C_1$–$C_4$ alkyl), $-N(C_1$–$C_4$ alkyl)($C_1$–$C_2$ alkyl), $-S(C_1$–$C_4$ alkyl), $-SO(C_1$–$C_4$ alkyl), $-SO_2(C_1$–$C_4)$alkyl, $-CO(C_1$–$C_4$ alkyl) $-C(=O)H$ or $-C(=O)O(C_1$–$C_4$alkyl), wherein each of the ($C_1$–$C_6$ alkyl) and ($C_1$–$C_4$ alkyl) moieties in the foregoing $R^4$ groups may optionally contain one or two double or triple bonds and may optionally be substituted with one or two substituents independently selected from hydroxy, amino, $C_1$–$C_3$ alkoxy, dimethylamino, methylamino, ethylamino, $-NHC(=O)CH_3$, fluoro, chloro, $C_1$–$C_3$ thioalkyl, $-CN$, $-COOH$, $-C(=O)O(C_1$–$C_4$ alkyl), $-C(=O)(C_1$–$C_4$ alkyl) and $-NO_2$;

$R^5$ is phenyl, naphthyl, thienyl, benzothienyl, pyridyl, quinolyl, pyrazinyl, furanyl, benzofuranyl, benzothiazolyl, benzisothiazolyl, benzisoxazolyl, benzimidazolyl, indolyl, benzoxazolyl or $C_3$–$C_8$ cycloalkyl wherein one or two of the carbon atoms of said cycloalkyl rings that contain at least 5 ring members may optionally and independently be replaced by an oxygen or sulfur atom or by $NZ^4$ wherein $Z^4$ is hydrogen, $C_1$–$C_4$ alkyl or benzyl; and wherein each of the foregoing $R^5$ groups is substituted with from one to four substituents $R^{12}$ wherein one to three of said substituents may be selected, independently, from chloro, $C_1$–$C_6$ alkyl and $-O(C_1$–$C_6$ alkyl) and one of said substituents may be selected from bromo, iodo, formyl, $-CN$, $-CF_3$, $-NO_2$, $-NH_2$, $-NH(C_1$–$C_4$ alkyl), $-N(C_1$–$C_2$ alkyl)($C_1$–$C_6$ alkyl), $-C(=O)(C_1$–$C_4$ alkyl), $-COOH$, $-SO_2NH(C_1$–$C_4$ alkyl), $-SO_2N(C_1$–$C_2$ alkyl)($C_1$–$C_4$ alkyl), $-SO_2NH_2$, $-NHSO_2(C_1$–$C_4$ alkyl), $-S(C_1$–$C_6$ alkyl) and $-SO_2(C_1$–$C_6$ alkyl), and wherein each of the $C_1$–$C_4$ alkyl and $C_1$–$C_6$ alkyl moieties in the foregoing $R^5$ groups may optionally be substituted with one or two substituents independently selected from fluoro, hydroxy, amino, methylamino, dimethylamino and acetyl;

$R^7$ is hydrogen, $C_1$–$C_4$ alkyl, halo, cyano, hydroxy, $-O(C_1$–$C_4$ alkyl) $-C(=O)(C_1$–$C_4$ alkyl), $-C(=O)O(C_1$–$C_4$alkyl), $-OCF_3$, $-CF_3$, $-CH_2OH$, $-CH_2O(C_1$–$C_4$ alkyl);

$R^{10}$ is hydrogen, hydroxy, methoxy or fluoro;

$R^{11}$ is hydrogen or $C_1$–$C_4$ alkyl; and

Z is NH, oxygen, sulfur, —N($C_1$–$C_4$ alkyl), —NC(=O)($C_1$–$C_2$ alkyl), NC(=O)O($C_1$–$C_2$alkyl) or $CR^{13}R^{14}$ wherein $R^{13}$ and $R^{14}$ are independently selected from hydrogen, trifluoromethyl and methyl with the exception that one of $R^{13}$ and $R^{14}$ can be cyano;

with the proviso that: (a) in the five membered rings of structures I, II and III, there can not be two double bonds adjacent to each other; and (b) when $R^4$ is attached to nitrogen, it is not halo, cyano or nitro;

or a pharmaceutically acceptable salt of such compound.

VI. The CRF antagonist can also be of the following formula, disclosed in WO 98/05661:

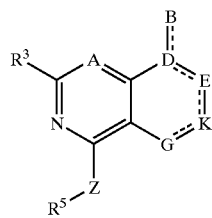

wherein the dashed lines represent optional double bonds;

A is nitrogen or $CR^7$;

B is —$NR^1R^2$, —$CR^1R^2R^{10}$, —C(=$CR^2R^{11}$)$R^1$, —$NHCR^1R^2R^{10}$, —$OCR^1R^2R^{10}$, —$SCR^1R^2R^{10}$, —$CR^2R^{10}NHR^1$, —$CR^2R^{10}OR^1$, —$CR^2R^{10}SR^1$ or —$COR^2$, and is single bonded to D; or B is —$CR^1R^2$, and is double bonded to D and D is carbon;

D is nitrogen or $CR^4$ and is single bonded to all atoms to which it is attached, or D is carbon and is double bonded to E or double bonded to B;

E is oxygen, nitrogen, sulfur, C=O, C=S, $CR^6R^{12}$, $NR^6$ or $CR^6$; or E is a two atom spacer, wherein one of the atoms is oxygen, nitrogen, sulfur, C=O, C=S, $CR^6R^{12}$, $NR^6$ or $CR^6$, and the other is $CR^6R^{12}$ or $CR^9$;

K and G are each, independently, C=O, C=S, sulfur, oxygen, $CHR^8$ or $NR^8$ when single bonded to both adjacent ring atoms, or nitrogen or $CR^8$ when it is double bonded to an adjacent ring atom;

the 6- or 7-membered ring that contains D, E, K and G may contain from one to three double bonds, from zero to two heteroatoms selected from oxygen, nitrogen and sulfur, and from zero to two C=O or C=S groups, wherein the carbon atoms of such groups are part of the ring and the oxygen and sulfur atoms are substituents on the ring;

$R^1$ is $C_1$–$C_6$ alkyl optionally substituted with from one or two substituents independently selected from hydroxy, fluoro, chloro, bromo, iodo, $C_1$–$C_4$ alkoxy, $CF_3$, —C(=O)($C_1$–$C_4$ alkyl), —C(=O)—O—($C_1$–$C_4$) alkyl, —OC(=O)($C_1$–$C_4$ alkyl), —OC(=O)N($C_1$–$C_4$ alkyl)($C_1$–$C_2$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —S($C_1$–$C_4$ alkyl), —CN, —$NO_2$, —SO($C_1$–$C_4$ alkyl), —$SO_2$($C_1$–$C_4$ alkyl), —$SO_2$NH($C_1$–$C_4$ alkyl) and —$SO_2$N($C_1$–$C_4$ alkyl)($C_1$–$C_2$ alkyl), wherein each of the $C_1$–$C_4$ alkyl groups in the foregoing $R^1$ groups may optionally contain one or two double or triple bonds;

$R^2$ is $C_1$–$C_{12}$ alkyl which may optionally contain from one to three double or triple bonds, aryl or ($C_1$–$C_4$ alkylene)aryl, wherein said aryl and the aryl moiety of said ($C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3$–$C_8$ cycloalkyl or ($C_1$–$C_6$ alkylene)($C_3$–$C_8$ cycloalkyl), wherein one or two of the carbon atoms of said cycloalkyl and the 5 to 8 membered cycloalkyl moieties of said ($C_1$–$C_6$ alkylene)($C_3$–$C_8$ cycloalkyl may optionally and independently be replaced by an oxygen or sulfur and wherein each of the foregoing $R^2$ groups may optionally be substituted with from one to three substituents independently selected from chloro, fluoro, hydroxy and $C_1$–$C_4$ alkyl, or with one substituent selected from $C_1$–$C_6$ alkoxy, —OC(=O)($C_1$–$C_6$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)—CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —$NO_2$, —SO($C_1$–$C_4$ alkyl), —$SO_2$($C_1$–$C_4$ alkyl), —$SO_2$NH($C_1$–$C_4$ alkyl) and —$SO_2$N($C_1$–$C_4$ alkyl)($C_1$–$C_2$ alkyl);

—$NR^1R^2$ or $CR^1R^2R^{10}$ may form a ring selected from saturated 3 to 8 membered rings, the 5 to 8 membered rings of which may optionally contain one or two double bonds, and wherein one or two of the ring carbon atoms of such 5 to 8 membered rings may optionally and independently be replaced by an oxygen or sulfur atom or by $NZ^3$ wherein $Z^3$ is hydrogen or $C_1$–$C_4$ alkyl;

$R^3$ is hydrogen, $C_1$–$C_4$ alkyl, —O($C_1$–$C_4$ alkyl), chloro, fluoro, bromo, iodo, —S($C_1$–$C_4$ alkyl) or —$SO_2$($C_1$–$C_4$ alkyl);

$R^4$ is hydrogen, $C_1$–$C_2$ alkyl, hydroxy or fluoro;

each $R^6$, $R^8$ and $R^9$ that is attached to a carbon atom is selected, independently, from hydrogen, $C_1$–$C_2$ alkyl, fluoro, chloro, bromo, iodo, hydroxy, hydroxymethyl, formyl, trifluoromethyl, cyano, amino, nitro, —O($C_1$–$C_2$ alkyl), —N($C_1$–$C_2$ alkyl)($C_1$–$C_2$ alkyl), —S($C_1$–$C_2$ alkyl), —CO($C_1$–$C_2$ alkyl), —C(=O)H or —C(=O)O($C_1$–$C_2$ alkyl), wherein each of the $C_1$–$C_2$ alkyl moieties in the foregoing $R^6$, $R^8$, and $R^9$ groups may optionally contain one double or triple bond; and each $R^6$, $R^8$, and $R^9$ that is attached to a nitrogen atom is selected, independently, from hydrogen and $C_1$–$C_4$ alkyl;

$R^5$ is substituted phenyl, naphthyl, pyridyl or pyrimidyl, wherein each of the foregoing $R^5$ groups is substituted with from two to four substituents $R^{15}$, wherein from one to three of said substituents may be selected, independently, from chloro, $C_1$–$C_6$ alkyl, —O($C_1$–$C_6$ alkyl) and —($C_1$–$C_6$alkylene)O($C_1$–$C_6$alkyl), and wherein one of said substituents may be selected, independently, from bromo, iodo, formyl, cyano, trifluoromethyl, nitro, amino, —NH($C_1$–$C_4$ alkyl), —N($C_1$–$C_2$ alkyl)($C_1$–$C_6$ alkyl), —C(=O)O($C_1$–$C_4$ alkyl), —C(=O)($C_1$–$C_4$ alkyl), —COOH, —$SO_2$NH ($C_1$–$C_4$ alkyl), —$SO_2$N($C_1$–$C_2$ alkyl)($C_1$–$C_4$ alkyl), —$SO_2NH_2$, —$NHSO_2$($C_1$–$C_4$ alkyl), —S($C_1$–$C_6$ alkyl) and —$SO_2$($C_1$–$C_6$ alkyl), and wherein each of the $C_1$–$C_4$ alkyl and $C_1$–$C_6$ alkyl moieties in the foregoing $R^5$ groups may optionally be substituted with one or two substituents independently selected from fluoro, hydroxy, amino, methylamino, dimethylamino and acetyl;

$R^7$ is hydrogen, methyl, halo (e.q., chloro, fluoro, iodo or bromo), hydroxy, methoxy, —C(=O)($C_1$–$C_2$ alkyl), —C(=O)O($C_1$–$C_2$ alkyl), trifluoromethoxy, hydroxymethyl, trifluoromethyl or formyl;

$R^{10}$ is hydrogen, hydroxy, methoxy or fluoro;

$R^{11}$ is hydrogen or $C_1$–$C_4$ alkyl;

$R^{12}$ is hydrogen or methyl; and

Z is NH, oxygen, sulfur, —N($C_1$–$C_4$ alkyl), or $CR^{13}R^{14}$ wherein $R^{13}$ and $R^{14}$ are independently selected from hydrogen, and methyl with the exception that one of $R^{13}$ and $R^{14}$ may optionally be cyano;

with the proviso that: (a) in the six or seven membered rings of structures in formula I, there can not be two double bonds adjacent to each other; and (b) when D is carbon and is double bonded to B, then B is $CR^1R^2$;

or a pharmaceutically acceptable salt of such compound.

VII. The CRF antagonist can also be of the following formula, disclosed in WO 98/08847:

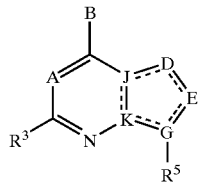

or a pharmaceutically acceptable salt thereof, wherein the dashed lines represent optional double bonds;

A is nitrogen or $CR^7$;

B is —$NR^1R^2$, —$CR^1R^2R^{10}$—C(=$CR^2R^{11}$)$R^1$, —$NHCR^1R^2R^{10}$, —$SCR^1R^2R^{10}$, —$CR^2R^{10}NHR^1$, —$CR^2R^{10}OR^1$, —$CR^2R^{10}SR^1$ or —$COR^2$;

J and K are each independently nitrogen or carbon and both J and K are not nitrogens;

D and E are each selected, independently, from nitrogen, $CR^4$, C=O, C=S, sulfur, oxygen, $CR^4R^6$ and $NR^8$;

G is nitrogen or carbon;

the ring containing D, E, G, K, and J in formula I may be a saturated or unsaturated 5-membered ring and may optionally contain one or two double bonds and may optionally contain from one to three heteroatoms in the ring and may optionally have one or two C=O or C=S groups;

$R^1$ is $C_1$–$C_6$ alkyl optionally substituted with one or two substituents independently selected from hydroxy, fluoro, chloro, bromo, iodo, —O—($C_1$–$C_4$ alkyl), $CF_3$, —C(=O)O—($C_1$–$C_4$alkyl), —OC(=O)($C_1$–$C_4$ alkyl), —OC(=O)N($C_1$–$C_4$ alkyl)($C_1$–$C_2$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —S($C_1$–$C_4$ alkyl), —CN, —$NO_2$, —SO($C_1$–$C_4$ alkyl), —$SO_2$($C_1$–$C_4$ alkyl), —$SO_2$NH($C_1$–$C_4$ alkyl) and —$SO_2$N($C_1$–$C_4$ alkyl)($C_1$–$C_2$ alkyl), wherein each of the $C_1$–$C_4$ alkyl groups in the foregoing $R^1$ groups may optionally contain one or two double or triple bonds;

$R^2$ is $C_1$–$C_{12}$ alkyl which may optionally contain from one to three double or triple bonds, aryl or ($C_1$–$C_4$ alkylene)aryl, wherein said aryl and the aryl moiety of said ($C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3$–$C_8$ cycloalkyl or ($C_1$–$C_6$ alkylene)($C_3$–$C_8$ cycloalkyl), wherein one or two of the carbon atoms of said cycloalkyl and the 5 to 8 membered cycloalkyl moieties of said ($C_1$–$C_6$ alkylene)($C_3$–$C_8$ cycloalkyl) may optionally and independently be replaced by an oxygen or sulfur atom or by $NZ^2$ wherein $Z^2$ is selected from hydrogen, $C_1$–$C_4$ alkyl, benzyl and $C_1$–$C_4$ alkanoyl, and wherein each of the foregoing $R^2$ groups may optionally be substituted with from one to three substituents independently selected from chloro, fluoro, hydroxy and $C_1$–$C_4$ alkyl, or with one substituent selected from bromo, iodo, $C_1$–$C_6$ alkoxy, —OC(=O)($C_1$–$C_6$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)-CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —$NO_2$, —SO($C_1$–$C_4$ alkyl), —$SO_2$($C_1$–$C_4$ alkyl), —$SO_2$NH($C_1$–$C_4$ alkyl) and —$SO_2$N($C_1$–$C_4$ alkyl)($C_1$–$C_2$ alkyl);

—$NR^1R^2$ or $CR^1R^2R^{10}$ may form a saturated 3 to 8 membered carbocyclic ring which may optionally contain from one to three double bonds and wherein one or two of the ring carbon atoms of such 5 to 8 membered rings may optionally and independently be replaced by an oxygen or sulfur atom or by $NZ^3$ wherein $Z^3$ is hydrogen, $C_1$–$C_4$ alkyl, benzyl or $C_1$–$C_4$ alkanoyl;

$R^3$ is hydrogen, $C_1$–$C_4$ alkyl, —O($C_1$–$C_4$ alkyl), chloro, fluoro, bromo, iodo, ($C_1$–$C_2$ alkylene)-O—($C_1$–$C_2$ alkyl), ($C_1$–$C_2$ alkylene)-OH, or —S($C_1$–$C_4$ alkyl);

each $R^4$ is, independently, hydrogen, ($C_1$–$C_6$ alkyl), fluoro, chloro, bromo, iodo, hydroxy, cyano, amino, ($C_1$–$C_2$ alkylene)-OH, $CF_3$, $CH_2SCH_3$, nitro, —O($C_1$–$C_4$ alkyl), —N($C_1$–$C_4$ alkyl)($C_1$–$C_2$ alkyl), —S($C_1$–$C_4$ alkyl), —CO($C_1$–$C_4$ alkyl), —C(=O)H or —C(=O)O($C_1$–$C_4$alkyl);

$R^6$ is hydrogen, methyl or ethyl;

$R^8$ is hydrogen or $C_1$–$C_4$ alkyl;

$R^5$ is phenyl, pyridyl, pyrazinyl, pyrimidyl, pyridazinyl and wherein each of the foregoing $R^5$ groups is substituted with from one to four substituents $R^{13}$ wherein one to three of said substituents may be selected, independently, from fluoro, chloro, $C_1$–$C_6$ alkyl and —O($C_1$–$C_6$ alkyl) and one of said substituents may be selected from bromo, iodo, formyl, OH, ($C_1$–$C_4$ alkylene)-OH, ($C_1$–$C_4$alkylene)-O—($C_1$–$C_2$ alkyl), —CN, —$CF_3$, —$NO_2$, —$NH_2$, —NH($C_1$–$C_4$ alkyl), —N($C_1$–$C_2$ alkyl)($C_1$–$C_6$ alkyl), —OCO($C_1$–$C_4$ alkyl), ($C_1$–$C_4$ alkylene)-O—($C_1$–$C_4$ alkyl), —S($C_1$–$C_6$ alkyl), ($C_1$–$C_4$ alkylene)-S—($C_1$–$C_4$ alkyl), —C(=O) O($C_1$–$C_4$ alkyl), —C(=O)($C_1$–$C_4$ alkyl), —COOH, —$SO_2$NH($C_1$–$C_4$ alkyl), —$SO_2$N($C_1$–$C_2$ alkyl)($C_1$–$C_4$ alkyl), —$SO_2NH_2$, —$NHSO_2$($C_1$–$C_4$ alkyl), —S($C_1$–$C_6$ alkyl) and —$SO_2$($C_1$–$C_6$ alkyl), and wherein each of the $C_1$–$C_4$ alkyl and $C_1$–$C_6$ alkyl moieties in the foregoing $R^5$ groups may optionally have one or two double bonds;

$R^7$ is hydrogen, $C_1$–$C_4$ alkyl, halo (e.g., chloro, fluoro, iodo or bromo), hydroxy, —O($C_1$–$C_4$ alkyl), —C(=O)($C_1$–$C_4$ alkyl), —C(=O)O($C_1$–$C_4$ alkyl), —$OCF_3$, —$CF_3$, —$CH_2OH$ or —$CH_2O$($C_1$–$C_2$ alkyl);

$R^{10}$ is hydrogen, hydroxy, methoxy or fluoro;

$R^{11}$ is hydrogen or $C_1$–$C_4$ alkyl; and with the proviso that: a) when both J and K are carbons and D is $CR^4$ and E is nitrogen, then G can not be nitrogen; (b) when both J and K are carbons and D and G are nitrogens, then E can not be CR⁴ or C=O or C=S; (c) when both J and K are carbons and D and E are carbons, then G can not be nitrogen; (d) when G is carbon, it must be double banded to E; and (e) in the ring containing J, K, D, E and G, there can not be two double bonds adjacent to each other;

and the pharmaceutically acceptable salts of such compounds.

VII. Other useful CRF antagonists are of the following formula, disclosed in WO 98/08846:

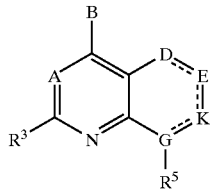

wherein the dashed lines represent optional double bonds;

A is nitrogen or CR⁷;

B is —NR¹R², —CR¹R²R¹⁰, —C(=CR ²R¹¹)R¹, —NHCR¹R²R¹⁰, —OCR¹R²R¹⁰, —SCR¹R²R¹⁰, —CR²R¹⁰NHR¹, —CR²R¹⁰OR¹, —CR²R¹⁰SR¹ or —COR²;

G is nitrogen or CR⁴ and is single bonded to all atoms to which it is attached, or G is carbon and is double bonded to K;

K is nitrogen or CR⁶ when double bonded to G or E, or K is oxygen, sulfur, C=O, C=S, CR⁶R¹²or NR⁸ when single bonded to both adjacent ring atoms, or K is a two atom spacer, wherein one of the two ring atoms of the spacer is oxygen, nitrogen, sulfur, C=O, C=S, CR⁶R¹², NR⁶ or CR⁶, and the other is CR⁶R¹² or CR⁹;

D and E are each, independently, C=O, C=S, sulfur, oxygen, CR⁴R⁶ or NR⁸ when single bonded to both adjacent ring atoms, or nitrogen or CR⁴ when it is double bonded to an adjacent ring atom;

the 6- or 7-membered ring that contains D, E, K and G may contain from one to three double bonds, from zero to two heteroatoms selected from oxygen, nitrogen and sulfur, and from zero to two C=O or C=S groups, wherein the carbon atoms of such groups are part of the ring and the oxygen and sulfur atoms are substituents on the ring;

R¹ is C₁–C₆ alkyl optionally substituted with from one or two substituents independently selected from hydroxy, fluoro, chloro, bromo, iodo, C₁–C₄ alkoxy, CF₃, —C(=O)(C₁–C₄ alkyl), —C(=O)—O—(C₁–C₄) alkyl, —OC(=O)(C₁–C₄ alkyl), —OC(=O)N(C₁–C₄ alkyl)(C₁–C₂ alkyl), —NHCO(C₁–C₄ alkyl), —COOH, —COO(C₁–C₄ alkyl), —CONH(C₁–C₄ alkyl), —CON(C₁–C₄ alkyl)(C₁–C₂ alkyl), —S(C₁–C₄ alkyl), —CN, —NO₂, —SO(C₁–Calkyl), —SO₂ (C₁–C₄ alkyl), —SO₂NH(C₁–C₄ alkyl) and —SO₂N (C₁–C₄ alkyl)(C₁C₂ alkyl), wherein each of the C₁–C₄ alkyl groups in the foregoing R¹ groups may optionally contain one or two double or triple bonds;

R² is C₁–C₂ alkyl which may optionally contain from one to three double or triple bonds, aryl or (C₁–C₄ alkylene) aryl, wherein said aryl and the aryl moiety of said (C₁–C₄ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; C₃–C₈ cycloalkyl or (C₁–C₆ alkylene)(C₃–C₈ cycloalkyl), wherein one or two of the carbon atoms of said cycloalkyl and the 5 to 8 membered cycloalkyl moieties of said (C₁–C₆ alkylene)(C₃–C₈ cycloalkyl may optionally and independently be replaced by an oxygen or sulfur atom or by NZ wherein Z is hydrogen, C₁–C₄ alkyl or benzyl, and wherein each of the foregoing R² groups may optionally be substituted with from one to three substituents independently selected from chloro, fluoro, hydroxy and C₁–C₄ alkyl, or with one substituent selected from C₁–C₆ alkoxy, —OC (=O)(C₁–C₆ alkyl), —OC(=O)N(C₁–C₄ alkyl) (C₁–C₂ alkyl), —S(C₁–C₆ alkyl), —NH(C₁–C₂ alkyl), —N(C₁–C₂ alkyl)(C₁–C₄ alkyl), —N(C₁–C₄ alkyl)-CO—(C₁–C₄ alkyl), —NHCO(C₁–C₄ alkyl), —COOH, —COO(C₁–C₄ alkyl), —CONH(C₁–C₄ alkyl), —CON(C₁–C₄ alkyl)(C₁–C₂ alkyl), —SH, —CN, —NO₂, —SO(C₁–C₄ alkyl), —SO₂(C₁–C₄ alkyl) —SO₂NH(C₁–C₄ alkyl) and —SO₂N(C₁–C₄ alkyl)(C₁–C₂ alkyl);

—NR¹R² or CR¹R²R¹⁰ may form a ring selected from saturated 3 to 8 membered rings, the 5 to 8 membered rings of which may optionally contain one or two double bonds, and wherein one or two of the ring carbon atoms of such 5 to 8 membered rings may optionally and independently be replaced by an oxygen or sulfur atom or by NZ² wherein Z² is hydrogen, benzyl or C₁–C₄ alkyl;

R³ is hydrogen, C₁–C₄ alkyl, —O(C₁–C₄ alkyl), chloro, fluoro, bromo, iodo, —S(C₁–C₄ alkyl) or —SO₂(C₁–C₄ alkyl);

each R⁸, R⁹ and R¹² is selected, independently, from. hydrogen and C₁–C₂ alkyl;

each R⁴ and R⁶ that is attached to a carbon atom is selected, independently, from hydrogen and C₁–C₆ alkyl, fluoro, chloro, bromo, iodo, hydroxy, hydroxy (C₁–C₂ alkyl), trifluoromethyl, cyano, amino, nitro, —O(C₁–C₄ alkyl), —N(C₁–C₄ alkyl)(C₁–C₂ alkyl), —CH₂SCH₃, —S(C₁–C₄ alkyl), —CO(C₁–C₄ alkyl), —C(=O)H or —C(=O)O(C₁–C₄ alkyl), wherein each of the C₁–C₂ alkyl moieties in the foregoing R⁴ and R⁶ groups may optionally contain one double or triple bond; and R⁶, when attached to a nitrogen atom, is selected from hydrogen and C₁–C₄ alkyl;

R⁵ is substituted phenyl, naphthyl, pyridyl or pyrimidyl, wherein each of the foregoing R⁵ groups is substituted with from two to four substituents R¹³, wherein up to three of said substituents may be selected, independently, from chloro, C₁–C₆ alkyl, —O(C₁–C₆ alkyl) and —(C₁–C₆ alkylene)O(C₁–C₆alkyl), and wherein one of said substituents may be selected, independently, from bromo, iodo, formyl, cyano, trifluoromethyl, nitro, amino, —NH(C₁–C₄ alkyl), —N(C₁–C₂ alkyl)(C₁–C₆ alkyl), —C(=O)O(C₁–C₄ alkyl), —C(=O)(C₁–C₄ alkyl), —COOH, —SO₂NH (C₁–C₄ alkyl), —SO₂N(C₁–C₂ alkyl)(C₁–C₄ alkyl), —SO₂NH₂, —NHSO₂(C₁–C₄ alkyl), —(C₀–C₁alkylene)-S—(C₁–C₂alkyl), —(C₀–C₁ alkylene)-SO—(C₁–C₂alkyl), —(C₀–C₁alkylene)-SO—(C₁–C₂alkyl), and —(C₁–C₄alkylene)-OH, and wherein each of the C₁–C₄ alkyl and C₁–C₆ alkyl moieties in the foregoing R⁵ groups may optionally be substituted with one or two substituents independently selected from fluoro, hydroxy, amino, methylamino, dimethylamino and acetyl;

R$^7$ is hydrogen, methyl, halo (e.g., chloro, fluoro, iodo or bromo), hydroxy, methoxy, —C(=O)(C$_1$-C$_2$ alkyl), —C(=O)O(C$_1$-C$_2$ alkyl), hydroxymethyl, trifluoromethyl or formyl;

R$^{10}$ is hydrogen, hydroxy, methoxy or fluoro; and

R$^{11}$ is hydrogen or C$_1$-C$_4$ alkyl;

with the proviso that in the ring containing D, E, K and G of formula I, there can not be two double bonds adjacent to each other;

and the pharmaceutically acceptable salt of such compound.

IX. The CRF antagonist may also be of the following formula, disclosed in WO 95/10506:

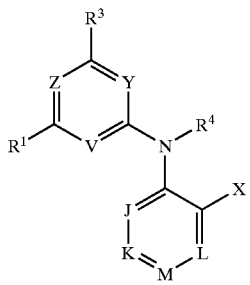

or a pharmaceutically, acceptable salt or prodrug thereof, wherein Y is CR$^{3a}$, N, or CR$^{29}$;

when Y is CR$^{3a}$ or N:

R$^1$ is independently selected at each occurrence from the group consisting of C$_1$-C$_4$ alkyl, C$_2$-C$_4$ alkenyl, C$_2$-C$_4$ alkynyl, halogen, C$_1$-C$_2$ haloalkyl, NR$^6$R$^7$, OR$^8$, and S(O)$_n$R$^8$;

R$^3$ is C$_1$-C$_4$ alkyl, aryl, C$_3$-C$_6$ cycloalkyl, C$_1$-C$_2$ haloalkyl, halogen, nitro, NR$^6$R$^7$, OR$^8$, S(O)$_n$R$^8$ C(=O)R$^9$, C(=O)NR$^6$R$^7$, C(=S)NR$^6$R$^7$, —(CHR$^{16}$)$_k$NR$^6$R$^7$, (CH$_2$)$_k$OR$^8$, C(=O)NR$^{10}$CH(R$^{11}$)CO$_2$R$^{12}$, —C(OH)(R$^{25}$)(R$^{25a}$), —(CH$_2$)$_p$S(O)$_n$-alkyl, —(CHR$^{16}$)R$^{25}$, —C(CN)(R$^{25}$)(R$^{16}$) provided that R$^{25}$ is not —NH— containing rings, —C(=O)R$^{25}$, —CH(CO$_2$R$^{16}$)$_2$, NR$^{10}$C(=O)CH(R$^{11}$)NR$^{10}$R$^{12}$, NR$^{10}$CH(R$^{11}$)CO$_2$R$^{12}$, substituted C$_1$-C$_4$ alkyl, substituted C$_2$-C$_4$ alkenyl, substituted C$_2$-C$_4$ alkynyl, substituted C$_1$-C$_4$ alkoxy, aryl-(substituted C$_1$-C$_4$) alkyl, aryl-(substituted C$_1$-C$_4$) alkoxy, substituted C$_3$-C$_6$ cycloalkyl, amino-(substituted C$_1$-C$_4$)alkyl, substituted C$_1$-C$_4$ alkylamino, where substitution by R$^{27}$ can occur on any carbon containing substituent; 2-pyridinyl, imidazolyl, 3-pyridinyl, 4-pyridinyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, azetidinyl, phenyl, 1H-indazolyl, 2-pyrrolidonyl, 2H,6H-1,5,2-dithiazinyl, 2H-pyrrolyl, 3H-indolyl, 4-piperidonyl, 4aH-carbazolyl, 4H-quinolizinyl, 6H-1,2,5-thiadiazinyl, acridinyl, azocinyl, azepinyl, benzofuranyl, benzothiophenyl, carbazolyl, chromanyl, chromenyl, cinnolinyl, decahydroquinolinyl, furazanyl, imidazolidinyl, indolinyl, indolizinyl, indolyl, isobenzofuranyl, isochromanyl, isoindolinyl, isoindolyl, isoquinolinyl, benzimidazolyl, isothiazolyl, isoxazolyl, morpholinyl, naphthyridinyl, octahydroisoquinolinyl, oxazolidinyl, oxazolyl, phenanthridinyl, phenanthrolinyl, phenazinyl, phenoxathiinyl, phenoxazinyl, phthalazinyl, piperazinyl, piperidinyl, pteridinyl, purinyl, pyranyl, pyrazolidinyl, pyrazolinyl, pyrazolyl, pyridazinyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrahydroisoquinolinyl, tetrahydroquinolinyl, tetrazolyl, thianthrenyl, thiazolyl, thiophenyl, triazinyl, xanthenyl; or 1-tetrahydroquinolinyl or 2-tetrahydroisoquinolinyl either of which can be substituted with 0–3 groups chosen from keto and C$_1$-C$_4$ alkyl;

J, K, and L are independently selected at each occurrence from the group of N, CH, and CX';

M is CR$^5$ or N;

V is CR$^{1a}$ or N;

Z is CR$^2$ or N;

R$^{1a}$, R$^2$, and R$^{3a}$ are independently selected at each occurrence from the group consisting of hydrogen, halo, halomethyl, C$_1$-C$_3$ alkyl, and cyano;

R$^4$ is (CH$_2$)$_m$OR$^{16}$, C$_1$-C$_4$ alkyl, allyl, propargyl, (CH$_2$)$_m$R$^{13}$, or —(CH$_2$)$_m$OC(O)R$^{16}$;

X is halogen, aryl, heteroaryl, S(O)$_z$R$^8$, SR$^8$, halomethyl, —(CH$_2$)$_p$OR$^8$, cyano, —(CHR$^{16}$)$_p$NR$^{14}$R$^{15}$, —C(=O)R$^8$, C$_1$-C$_6$ alkyl, C$_4$-C$_{10}$ cycloalkylalkyl, C$_1$-C$_{10}$alkenyl, C$_2$-C$_{10}$alkynyl, C$_2$-C$_{10}$alkoxy, aryl-(C$_2$-C$_{10}$)-alkyl, C$_3$-C$_6$cycloalkyl, aryl-(C$_1$-C$_{10}$)-alkoxy, nitro, thio-(C$_1$-C$_{10}$)-alkyl, —C(=NOR$^{16}$)-C$_1$-C$_4$—alkyl, —C(=NOR$^{16}$)H, and —C(=O)NR$^{14}$R$^{15}$, where substitution by R$^{18}$ can occur on any carbon containing substituents;

X' is independently selected at each occurrence from the group consisting of hydrogen, halogen, aryl, heteroaryl, S(O)$_n$R$^8$, halomethyl, —(CHR$^6$)$_p$OR$^8$, cyano, —(CHR$^{16}$)$_p$NR$^{14}$R$^{15}$, C(=O)R$^8$, C$_1$-C$_6$ alkyl, C$_2$-C$_{10}$alkenyl, C$_2$-C$_{10}$alkoxy, aryl-(C$_1$-C$_{10}$)-alkyl, C$_3$-C$_6$cycloalkyl, aryl-(C$_1$-C$_{10}$)-alkoxy, nitro, thio-(C$_1$-C$_{10}$)-alkyl, —C(=NOR$^{16}$)-C$_1$-C$_4$-alkyl, —C(=NOR$^{16}$)H, and —C(=O)NR$^{14}$R$^{15}$, where substitution by R$^{16}$ can occur on any carbon containing substituents;

R$^5$ is halo, —C(=NOR$^{16}$)-C$_1$-C$_4$-alkyl, C$_1$-C$_4$alkyl, C$_1$-C$_3$ haloalkyl, —(CHR$^{16}$)$_p$OR$^8$, —(CHR$^{16}$)$_p$S(O)$_n$R$^8$, —(CHR$^6$)$_p$NR$^{14}$R$^{15}$, C$_3$-C$_6$ cycloalkyl, C$_2$-C$_{10}$alkenyl, C$_2$-C$_{10}$alkynyl, aryl-(C$_2$-C$_{10}$)-akyl, aryl-(C$_1$-C$_{10}$)-alkoxy, cyano, C$_3$-C$_6$ cycloalkoxy, nitro, amino-(C$_2$-C$_{10}$)-alkyl, thio-(C$_2$-C$_{10}$)-alkyl, SO$_n$(R$^8$), C(=O)R$^8$—C(=NOR$^{16}$)H, or —C(=O)NR$^{14}$R$^{15}$, where substitution by R$^{18}$ can occur on any carbon containing substituents;

R$^6$ and R$^7$ are independently selected at each occurrence from the group consisting of hydrogen, C$_1$-C$_6$ alkyl, C$_3$-C$_{10}$ cycloalkyl, C$_1$-C$_6$ alkoxy, (C$_4$-C$_{12}$)-cycloalkylalkyl, —(CH$_2$)$_k$R$^{13}$, (CHR$^{16}$)$_p$OR$^8$, —(C$_1$-C$_6$alkyl)-aryl, heteroaryl, —S(O)$_z$-aryl or —(C$_1$-C$_6$alkyl)-heteroaryl or aryl, wherein the aryl or heteroaryl groups are optionally substituted with 1–3 groups selected from the group consisting of hydrogen, halogen, C$_1$-C$_6$alkyl, C$_1$-C$_6$ alkoxy, amino, NHC(=O)(C$_1$-C$_6$ alkyl), NH(C$_1$-C$_6$ alkyl), N(C$_1$-C$_6$ alkyl)$_2$, nitro, carboxy, CO$_2$(C$_1$-C$_6$ alkyl), cyano, and S(O)$_2$—(C$_1$-C$_6$-alkyl); or can be taken together to form —(CH$_2$)$_p$A(CH$_2$)$_r$—, optionally substituted with 0–3 R$^{17}$; or, when considered with the commonly attached nitrogen, can be taken together to form a heterocycle, said heterocycle being substituted on carbon with 1–3 groups consisting of hydrogen, C$_1$-C$_6$ alkyl, hydroxy, or C$_1$-C$_6$ alkoxy;

A is $CH_2$, O, $NR^{25}$, C(=O), $S(O)_n$, $N(C(=O)R^{17})$, $N(R^{19})$, $C(H)(NR^{14}R^{15})$, $C(H)(OR^{20})$, $C(H)(C(=O)R^{21})$, or $N(S(O)_n, R^{21})$;

$R^8$ is independently selected at each occurrence from the group consisting of hydrogen; $C_1$–$C_6$ alkyl; -($C_4$–$C_{12}$) cycloalkylalkyl; $(CH_2)_r R^{22}$; $C_3$–$C_{10}$ cycloalkyl; —$NR^6R^7$; aryl; heteroaryl; —$NR^{16}(CH_2)_n R^6R^7$; —$(CH_2)_k R^{25}$; and $(CH_2)_t$ heteroaryl or $(CH_2)_t$ aryl, either of which can optionally be substituted with 1–3 groups selected from the group consisting of hydrogen, halogen, $C_1$–$C_6$ alkyl, $C_1$–$C_6$ alkoxy, amino, NHC(=O)($C_1$–$C_6$ alkyl), NH($C_1$–$C_6$ alkyl), N($C_1$–$C_6$ alkyl)$_2$, nitro, carboxy, $CO_2$($C_1$–$C_6$ alkyl), cyano, and $S(O)_2$($C_1$–$C_6$-alkyl);

$R^9$ is independently selected at each occurrence from $R^{10}$, hydroxy, $C_1$–$C_4$ alkoxy, $C_3$–$C_6$ cycloalkyl, $C_2$–$C_4$ alkenyl, aryl substituted with 0–3 $R^{18}$, and —($C_1$–$C_6$ alkyl)-aryl substituted with 0–3 $R^{18}$;

$R^{10}$, $R^{16}$, $R^{23}$, and $R^{24}$ are independently selected at each occurrence from hydrogen or $C_1$–$C_4$ alkyl;

$R^{11}$ is $C_1$–$C_4$ alkyl substituted with 0–3 groups chosen from the following: keto, amino, sulfhydryl, hydroxyl, guanidinyl, p-hydroxyphenyl, imidazolyl, phenyl, indolyl, and indolinyl, or, when taken together with an adjacent $R^{10}$, are $(CH_2)_r$;

$R^{12}$ is hydrogen or an appropriate amine protecting group for nitrogen or an appropriate carboxylic acid protecting group for carboxyl;

$R^{13}$ is independently selected at each occurrence from the group consisting of CN, $OR^{19}$, $SR^{19}$, and $C_3$–$C_6$ cycloalkyl;

$R^{14}$ and $R^{15}$ are independently selected at each occurrence from the group consisting of hydrogen, $C_4$–$C_{10}$, cycloalkyl-alkyl, and $R_{19}$;

$R^{17}$ is independently selected at each occurrence from the group consisting of $R^{10}$, $C_1$–$C_4$ alkoxy, halo, $OR^{23}$, $SR^{23}$, $NR^{23}R^{24}$, and ($C_1$–$C_6$) alkyl ($C_1$–$C_4$) alkoxy;

$R^{18}$ is independently selected at each occurrence from the group consisting of $R^{10}$, hydroxy, halogen, $C_1$–$C_2$ haloalkyl, $C_1$–$C_4$ alkoxy, $C(=O)R^{24}$, and cyano;

$R^{19}$ is independently selected at each occurrence from the group consisting of $C_1$–$C_6$ alkyl, $C_3$–$C_6$ cycloalkyl, $(CH_2)_w R^{22}$, and aryl substituted with 0–3 $R^{18}$;

$R^{20}$ is independently selected at each occurrence from the group consisting of $R^{10}$, $C(=O)R^{31}$, and $C_2$–$C_4$ alkenyl;

$R^{21}$ is independently selected at each occurrence from the group consisting of $R^{10}$, $C_1$–$C_4$ alkoxy, $NR^{23}R^{24}$, and hydroxyl;

$R^{22}$ is independently selected at each occurrence from the group consisting of cyano, $OR^{24}$, $SR^{24}$, $NR^{23}R^{24}$, $C_1$–$C_6$ alkyl, $C_3$–$C_6$ cycloalkyl, —$S(O)_n R^{31}$, and —$C(=O)R^{25}$;

$R^{25}$, which can be optionally substituted with 0–3 R17, is independently selected at each occurrence from the group consisting of phenyl, pyrazolyl, imidazolyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, azetidinyl, 1H-indazolyl, 2-pyrrolidonyl, 2H,6H-1,5,2-dithiazinyl, 2H-pyrrolyl, 3H-indolyl, 4-piperidonyl, 4aH-carbazolyl, 4H-quinolizinyl, 6H-1,2,5-thiadiazinyl, acridinyl, azocinyl, azepinyl, benzofuranyl, benzothiophenyl, carbazolyl, chromanyl, chromenyl, cinnolinyl, decahydroquinolinyl, furazanyl, indolinyl, indolizinyl, indolyl, isobenzofuranyl, isochromanyl, isoindolinyl, isoindolyl, isoquinolinyl benzimidazolyl, isothiazolyl, isoxazolyl, morpholinyl, naphthyridinyl, octahydroisoquinolinyl, oxazolidinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazolidinyl, pyridazinyl, pyridyl, pyrimidinyl, pyrrolidinyl, pyrrolinyl, pyrrolyl, quinazolinyl, quinolinyl, quinoxalinyl, quinuclidinyl, B-carbolinyl, tetrahydrofuranyl, tetrazolyl, thianthrenyl, thiazolyl, thiophenyl, triazinyl, xanthenyl; and 1-tetrahydroquinolinyl or 2-tetrahydroisoquinolinyl either of which can be substituted with 0–3 groups chosen from keto and $C_1$–$C_4$ alkyl;

$R^{25a}$, which can be optionally substituted with 0–3 $R^{17}$, is independently selected at each occurrence from the group consisting of H and $R^{25}$;

$R^{27}$ is independently selected at each occurrence from the group consisting of $C_1$–$C_3$ alkyl, $C_2$–$C_4$ alkenyl, $C_2$–$C_4$ alkynyl, $C_2$–$C_4$ alkoxy, aryl, nitro, cyano, halogen aryloxy, and heterocycle optionally linked through 0;

$R^{31}$ is independently selected at each occurrence from the group consisting of $C_1$–$C_4$ alkyl, $C_3$–$C_7$ cycloalkyl $C_4$–$C_{10}$ cycloalkyl-alkyl, and aryl-($C_1$–$C_4$) alkyl;

k, m, and r are independently selected at each occurrence from 1–4;

n is independently, selected at each occurrence from 0–2, p, q, and z are independently selected at each occurrence from 0–3;

t and w are independently selected at each occurrence from 1–6, provided that when J is CX' and K and L are both CH, and M is $CR^5$, then (A) when V and Y are N and Z is CH and $R^1$ and $R^3$ are methyl,
  (1) and $R^4$ is methyl, then
    (a) $R^5$ can not be methyl when X is OH and X' is H;
    (b) $R^5$ can not be —$NHCH_3$, or —$N(CH_3)_2$ when X and X' are —$OCH_3$; and
    (c) $R^5$ can not be —$N(CH_3)_2$ when X and X' are —$OCH_2CH_3$;
  (2) and $R^4$ is ethyl, then
    (a) $R^5$ can not be methylamine when X and X' are —$OCH_3$;
    (b) $R^5$ can not be OH when X is Br and X' is OH; and
    (c) $R^5$ can not be —$CH_2OH$ or —$CH_2N(CH_3)_2$ when X is —$SCH_3$ and X' is H;

(B) when V and Y are N, Z is CH, $R^4$ is ethyl, $R^5$ is iso-propyl, X is Br, X' is H, and
  (1) $R^1$ is $CH_3$, then
    (a) $R^3$ can not be OH, piperazin-1-yl, —$CH_2$,-piperidin-1-yl, —$CH_2$—(N-4-methylpiperazin-1-yl), —C(O)NH-phenyl, —$CO_2H$, —$CH_2O$-(4-pyridyl), —$C(O)NH_2$, 2-indolyl, —$CH_2O$-(4-carboxyphenyl), —$N(CH_2CH_3)$ (2-bromo-4-isopropylphenyl);
  (2) $R^2$ is —$CH_2CH_2CH_3$ then $R^3$ can not be —$CH_2CH_2CH_3$ (C) when V, Y and Z are N, $R^4$ is ethyl, and
  (1) $R^5$ is iso-propyl, X is bromo, and X' is H, then
    (a) $R^3$ can not be OH or —$OCH_2CN$ when $R^1$ is $CH_3$ and
    (b) $R^3$ can not be —$N(CH_3)_2$ when $R^1$ is —$N(CH_3)_2$;

(2) $R^5$ is —$OCH_3$, X is —$OCH_3$, and X' is H, then $R^3$ and $R^1$ can not both be chloro;

further provided that when J, K, and L are all CH and M is $CR^5$, then (D) at least one of V, Y, and Z must be N;
(E) when V is $CR^{1a}$, Z and Y can not both be N;
(F) when Y is $CR^{3a}$, Z and V can not both be N;
(G) when Z is $CR^2$, V and Y must both be N;
(H) Z can be N only when both V and Y are N or when V is $CR^{1a}$ and Y is $CR^{3a}$;
(I) when V and Y are N, Z is $CR^2$, and $R^2$ is H or $C_1$–$C_3$ alkyl, and $R^4$ is $C_1$–$C_3$ alkyl, $R^3$ can not be 2-pyridinyl, indolyl, indolinyl, imidazolyl, 3-pyridinyl, 4-pyridinyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-phenothiazinyl, or 4-pyrazinyl;
(J) when V and Y are N; Z is $CR^2$; $R^2$ is H or $C_1$–$C_3$ alkyl; $R^4$ is $C_1$–$C_4$ alkyl, $R^5$, X, and/or X' are OH, halo, $CF_3$, $C_1$–$C_4$ alkyl, $C_1$–$C_4$ alkoxy, $C_1$–$C_4$ alkylthio, cyano, amino, carbamoyl, or $C_1$–$C_4$ alkanoyl; and $R^1$ is $C_1$–$C_4$ alkyl, then $R^4$ can not be —NH(substituted phenyl) or —N($C_1$–$C_4$ alkyl) (substituted phenyl);

and wherein, when Y is $CR^{29}$:

J, K, L, M, Z, A, k, m, n, p, q, r, t, w, $R^3$, $R^{10}$, $R^{11}$, $R^{12}$, $R^{13}$, $R^{16}$, $R^{18}$, $R^{19}$, $R^{21}$, $R^{23}$, $R^{24}$, $R^{25}$, and $R^{27}$ are as defined above and $R^{25a}$, in addition to being as defined above, can also be $C_1$–$C_4$ alkyl, but V is N;

$R^1$ is $C_1$–$C_2$ alkyl, $C_2$–$C_4$ alkenyl, $C_2$–$C_4$ alkynyl, $C_2$–$C_4$ alkoxy, halogen, amino, methylamino, dimethylamino, aminomethyl, or N-methylaminomethyl;

$R^2$ is independently selected at each occurrence from the group consisting of hydrogen, halo, $C_1$–$C_3$ alkyl, nitro, amino, and —$CO_2R^{10}$;

$R_4$ is taken together with $R^{29}$ to form a 5-membered ring and is —$C(R^{26})$= or —N= when $R^{29}$ is —$C(R^{30})$= or —N=, or —$CH(R^{26})$— when $R^{29}$ is —$CH(R^{30})$—;

X is Cl, Br, I, $S(O)nR^8$, $OR^8$, halomethyl, —$(CHR^{16})_pOR^8$, cyano, —$(CHR^{16})_pNR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$ alkoxy, aryl-($C_1$–$C_{10}$)-alkyl, $C_3$–$C_6$ cycloalkyl, aryl-($C_1$–$C_{10}$)-alkoxy, nitro, thio-($C_1$–$C_{10}$)-alkyl, —$C(=NOR^{16})$—$C_1$–$C_4$-alkyl, —$C(=NOR^{16})$H, or $C(=O)NR^{14}R^{15}$ where substitution by $R^{18}$ can occur on any carbon containing substituents;

X' is hydrogen, Cl, Br, I, $S(O)_nR^8$, —$(CHR^{16})_pOR^8$, halomethyl, cyano, —$(CHR^{16})_pNR^{14}R^{15}$, $C(=O)R^8$, $C_1$–$C_6$ alkyl, $C_2$–$C_{10}$alkenyl, $C_2$–$C_{10}$, alkynyl, $C_1$–$C_{10}$ alkoxy, aryl-($C_1$–$C_{10}$)-alkyl, $C_3$–$C_6$ cycloalkyl, aryl-($C_2$–$C_{10}$)-alkoxy, nitro, thio-($C_2$–$C_{10}$)-alkyl, —$C(=NOR^{16})$—$C_1$–$C_4$-alkyl, —$C(=NOR^{16})$H, or $C(=O)N R^8R^{15}$ where substitution by $R^{18}$ can occur on any carbon containing substituents;

$R^5$ is halo, —$C(=NOR^{16})$-$C_1$–$C_4$-alkyl, $C_1$–$C_6$ alkyl, $C_1$–$C_3$ haloalkyl, $C_1$–$C_6$ alkoxy, $(CHR^{16})_pOR^5$, $(CHR^{16})_pS(O)R^8$, $(CHR^{16})_pNR^{14}R^{15}$, $C_3$–$C_6$ cycloalkyl, $C_2$–$C_{10}$ alkenyl, $C_2$–$C_{10}$ alkynyl, aryl-($C_2$–$C_{10}$)-alkyl, aryl-($C_1$–$C_{10}$)-alkoxy, cyano, $C_3$–$C_6$ cycloalkoxy, nitro, amino-($C_1$–$C_{10}$)-alkyl, thio-($C_1$–$C_{10}$)-alkyl, $SO_n(R^8)$, $C(=O)R^8$, —$C(=NOR^{16})$H, or $C(=O)NR^8R^{15}$ where substitution by $R^{18}$ can occur on any carbon containing substituents;

$R^6$ and $R^7$ are independently selected at each occurrence from the group consisting of hydrogen, $C_1$–$C_6$ alkyl, $C_3$–$C_{10}$ cycloalkyl, —$(CH_2)_kR^{13}$, $(C_4$–$C_{12})$-cycloalkylalkyl, $C_1$–$C_6$ alkoxy, —$(C_1$–$C_6$ alkyl)-aryl, heteroaryl, aryl, —$S(O)_z$-aryl or —$(C_1$–$C_6$ alkyl)-heteroaryl or aryl wherein the aryl or heteroaryl groups are optionally substituted with 1–3 groups selected from hydrogen, halogen, $C_1$–$C_6$ alkyl, $C_1$–$C_6$ alkoxy, amino, NHC(=O)($C_1$–$C_6$ alkyl), NH($C_1$–$C_6$ alkyl), N($C_1$–$C_6$ alkyl)$_2$, nitro carboxy, $CO_2(C_1$–$C_6$ alkyl), and cyano; or can be taken together to form —$(CH_2)qA(CH_2)_r$—, optionally substituted with 0–3 $R^{17}$; or, when considered with the commonly attached nitrogen, can be taken together to form a heterocycle, said heterocycle being substituted on carbon with 1–3 groups consisting of hydrogen, $C_1$–$C_6$ alkyl, hydroxy, or $C_1$–$C_6$ alkoxy;

$R^8$ is independently selected at each occurrence from the group consisting of hydrogen, $C_1$–$C_6$ alkyl, —$(C_4$–$C_{12})$ cycloalkylalkyl, $(CH_2)_tR^{22}$, $C_3$–$C_{10}$ cycloalkyl, —$(C_1$–$C_6$ alkyl)-aryl, heteroaryl, —$NR^{16}$, —$N(CH_2)_n NR^6R^7$; —$(CH_2)_kR^{25}$, —$(C_1$–$C_6$ alkyl)-heteroaryl or aryl optionally substituted with 1–3 groups selected from hydrogen, halogen, $C_1$–$C_6$ alkyl, $C_1$–$C_6$ alkoxy, amino, NHC(=O)($C_1$–$C_6$ alkyl), NH($C_1$–$C_6$ alkyl), N($C_1$–$C_6$alkyl)$_2$, nitro, carboxy, $CO_2(C_1$–$C_6$ alkyl), and cyano;

$R^9$ is independently selected at each occurrence from $R^{10}$, hydroxy, $C_1$–$C_4$ alkoxy, $C_3$–$C_6$ cycloalkyl, $C_2$–$C_4$ alkenyl, and aryl substituted with 0–3 $R^{18}$;

$R^{14}$ and $R^{15}$ are independently selected at each occurrence from the group consisting of hydrogen, $C_1$–$C_6$ alkyl, $C_3$–$C_6$ cycloalkyl, $(CH_2)_tR^{22}$, and aryl substituted with 0–3 $R^{18}$;

$R^{17}$ is independently selected at each occurrence from the group consisting of $R^{10}$, $C_1$–$C_4$ alkoxy, halo, $OR^{23}$, $SR^{23}$, and $NR^{23}R^{24}$;

$R^{20}$ is independently selected at each occurrence from the group consisting of $R^{10}$ and $C(=O)R^{31}$;

$R^{22}$ is independently selected at each occurrence from the group consisting of cyano, $OR^{24}$, $SR^{24}$, $NR^{23}R^{24}$, $C_3$–$C_6$ cycloalkyl, —$S(O)_nR^{31}$, and —$C(=O)R^{25}$;

$R^{26}$ is hydrogen or halogen;

$R^{28}$ is $C_1$–$C_2$, alkyl, $C_2$–$C_4$ alkenyl, $C_2$–$C_4$ alkynyl, hydrogen, $C_1$–$C_2$ alkoxy, halogen, or $C_2$–$C_4$ alkylamino;

$R^{29}$ is taken together with $R^4$ to form a five membered ring and is: —$CH(R^{30})$— when $R^4$ is —$CH(R^{28})$-$C(R^{30})$= or —N= when $R^4$ is —$C(R^{28})$= or —N=;

$R^{30}$ is hydrogen, cyano, $C_1$–$C_2$ alkyl, $C_1$–$C_2$ alkoxy, halogen, $C_1$–$C_2$ alkenyl, nitro, amido, carboxy, or amino;

$R^{31}$ is $C_1$–$C_4$ alkyl, $C_3$–$C_7$ cycloalkyl, or aryl-($C_1$–$C_4$) alkyl; provided that when J, K, and L are all CH, M is $CR^5$, Z is CH, $R^3$ is $CH_3$, $R^{28}$ is H, $R^5$ is isopropyl, X is Br, X' is H, and $R^1$ is $CH_3$, then $R^{30}$ can not be H, —$CO_2H$, or —$CH_2NH_2$; and further provided that when J, K and L are all CH; M is $CR^5$; Z is N; and (A) $R^{29}$ is —$C(R^{30})$=; then one of $R^{28}$ or $R^{30}$ is hydrogen;
(B) $R^{29}$ is N; then $R^3$ is not halo, $NH_2$, $NO_2$, $CF_3$, $CO_2H$, $CO_2$-alkyl, alkyl, acyl, alkoxy, OH, or —$(CH_2)_m$Oalkyl;
(C) $R^{29}$ is N; then $R^{28}$ is not methyl if X or X' are bromo or methyl and $R^5$ is nitro; or
(D) $R^{29}$ is N; and $R^1$ is $CH_3$; and $R^3$is amino; then $R^5$ is not halogen or methyl.

Preferred compounds of this group include those wherein:

i) V is N, $R^1$ is methyl; and $R^3$ is aryl, $NR^6R^7$, or $OR^8$;

ii) V is N, $R^1$ is methyl; $R^3$ is aryl, $NR^6R^7$, or $OR^8$; and $R^4$ is methyl or ethyl;

iii) V is N, $R^1$ is methyl; $R^3$ is aryl, $NR^6R^7$, or $OR^8$; $R^4$ is methyl or ethyl; and X is $O(C_1-C_4$ alkyl), Br, or $C_1-C_4$ alkyl;

iv) V is N, $R^1$ is methyl; $R^3$ is aryl, $NR^6R^7$, or $OR^8$; $R^4$ is methyl, ethyl; X is OMe, Br, or ($C_1-C_4$ alkyl), M is $C_1-C_4$ alkyl, Br, Cl, or O ($C_1-C_4$ alkyl); and v) V is N, $R^1$ is methyl; $R^3$ is aryl, $NR^6R^7$, $OR^8$; or $R^4$ is methyl, ethyl; X is OMe, Br, or $C_1-C_4$ alkyl, M is $C_1-C_4$ alkyl, Br, Cl, or O ($C_1-C_4$ alkyl); and L is CH, or N.

X. The invention also encompasses use of aminothiazole derivatives of the following formula, disclosed in WO 97/00868:

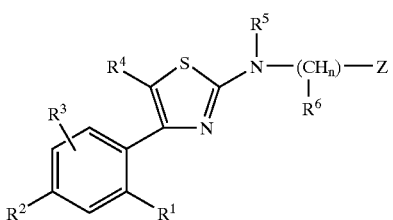

wherein each of $R^1$ and $R^2$ is independently a halogen atom; a $C_1-C_5$ hydroxyalkyl radical; $C_1-C_5$ alkyl; $C_7-C_{10}$ aralkyl; $C_1-C_5$ alkoxy; trifluoromethyl; nitro; nitrile; a group —SR where R is hydrogen, a $C_1-C_5$ alkyl radical or a $C_7-C_{10}$ aralkyl radical; a group S—CO—R where R is a $C_1-C_5$ alkyl radical or aralkyl in which the aryl portion is $C_6-C_8$ and the alkyl portion is $C_1-C_4$; a group —COOR' where R' is hydrogen or $C_1-C_5$ alkyl; a group —CONR'R" where R' and R" are as defined above for R'; a group —NR'R" where R' and R" are as previously defined for R'; a group —CONRaRb or NRaRb, where Ra and Rb, taken together with the nitrogen atom to which they are attached, form a 5- to 7-membered heterocyclic ring; or a group —NHCO—NR'R", where R' and R" are as defined above for R';$R^3$ is hydrogen or as defined for $R^1$ and $R^2$ is a hydrogen atom; $C_{1-5}$ alkyl; halogen; a hydroxymethyl group; or a formyl group; $R^5$ is $C_1-C_5$ alkyl; a $C_3-C_7$ cycloalkyl group; a cycloalkylalkyl group in which the cycloalkyl portion is $C_3-C_7$ and the alkyl portion is $C_1-C_5$; or $C_5-C_6$ alkenyl; n is 0 or 1; $R^6$ is $C_{1-5}$ alkyl; alkoxyalkyl in which the alkyl portions are $C_1-C_5$; $C_3-C_7$ cycloalkyl; a cycloalkylalkyl group in which the cycloalkyl portion is $C_3-C_7$ and the alkyl portion is $C_1-C_5$; a cycloalkyloxyalkyl radical in which the cycloalkyl is $C_3-C_7$ and the alkyl is $C_1-C_4$; a hydroxyalkyloxyalkyl radical in which the alkyls are $C_2-C_{10}$; or an alkoxyalkyloxyalkyl radical in which the alkyls are $C_3-C_{12}$; and Z is an optionally substituted bi- or tricyclic aromatic or heteroaromatic group; and stereoisomers and/or addition salts thereof.

XI. CRF antagonists of the following formula, disclosed in WO 97/29109, may also be employed:

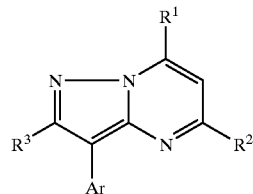

including the stereoisomers and the pharmaceutically acceptable acid addition salt forms thereof, wherein $R^1$ is $NR^4R^5$ or $OR^5$;

$R^2$ is $C_1-C_6$alkyl, $C_1-C_6$alkyloxy or $C_1-C_6$alkylthio, $R^3$ is hydrogen, $C_1-C_6$alkyl, $C_1-C_6$alkylsulfonyl, $C_1-C_6$alkylsulfoxy or $C_1-C_6$alkylthio;

$R^4$ is hydrogen, $C_1-C_6$alkyl, mono- or di($C_3-C_6$cyloalkylmethyl, $C_3-C_6$cyloalkyl, $C_3-C_6$alkenyl, hydroxy$C_1-C_6$alkyl, $C_1-C_6$akylcarbonyloxy$C_1-C_6$alkyl or $C_1-C_6$alkyloxy$C_1-C_6$alkyl;

$R^5$ is $C_1-C_8$alkyl, mono- or di($C_3-C_6$cycloalkyl)methyl, $Ar^1CH_2$, $C_3-C_6$alkenyl, $C_1-C_6$alkyloxy$C_1-C_6$alkyl, hydroxy$C_1-C_6$alkyl, thienylmethyl, furanylmethyl, $C_1-C_6$alkylthio$C_1-C_6$alkyl, morpholinyl, mono- or di($C_1-C_6$alkyl)amino$C_{1-6}$alkyl, di($C_1-C_6$alkyl)amino, $C_1-C_6$alkylcarbonyl$C_1-C_6$alkyl, $C_1-C_6$alkyl substituted with imidazolyl; or a radical of formula —Alk—O—CO—$Ar^1$;

or $R^4$ and $R^5$ taken together with the nitrogen atom to which they are attached may form a pyrrolidinyl, piperidinyl, homopiperidinyl or morpholinyl group, optionally substituted with $C_1-C_6$alkyl or $C_1-C_6$alkyloxy$C_1-C_6$alkyl; and Ar is phenyl; phenyl substituted with 1, 2 or 3 substituents independently selected from halo, $C_1-C_6$alkyl, trifluoromethyl, hydroxy, cyano, $C_1-C_6$alkyloxy, benzyloxy, $C_1-C_6$alkylthio, nitro, amino and mono- or di($C_1-C_6$alkyl)amino; pyridinyl; pyridinyl substituted with 1~2 or 3 substituents independently selected from halo, $C_1-C_6$alkyl, trifluoromethyl, hydroxy, cyano, $C_1-C_6$alkyloxy, benzyloxy, $C_1-C_6$alkylthio, nitro, amino, mono- or di($C_1-C_6$alkyl)amino and piperidinyl; and wherein said substituted phenyl may optionally be further substituted with one or more halogens;

$Ar^1$ is phenyl; phenyl substituted with 1, 2 or 3 substituents each independently selected from halo, $C_1-C_6$alkyl, $C_1-C_6$alkyloxy, di($C_1-C_6$alkyl)amino$C_1-C_6$alkly, trifluoromethyl and $C_1-C_6$alkyl substituted with morpholinyl; or pyridinyl; and Alk is $C_1-C_6$alkanediyl; with the proviso that 5-methyl-3-phenyl-7-(phenylmethoxy)-pyrazolo[1,5-a]-pyrimidine and 2,5-dimethyl-7-(methylamino)-3-phenyl-pyrazolo[1,5-a]pyrimidine are not included.

Preferred compounds of this formula are those wherein $R^2$ is methyl; $R^3$ is hydrogen, or $C_1-C_6$ alkyl; and Ar is substituted phenyl or 3-pyridyl.

XII. CRF antagonists of the following formula, disclosed in WO 97/29110, may also be employed:

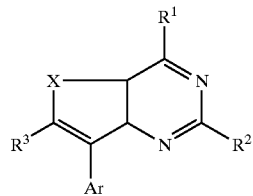

including the stereoisomers and the pharmaceutically acceptable acid addition salt forms thereof, wherein X is S, SO or $SO_2$;

$R^1$ is $NR^4R^5$ or $OR^5$;

$R^2$ is $C_1$–$C_6$alkyl, $C_1$–$C_6$alkyloxy or $C_1$–$C_6$alkylthio;

$R^3$ is hydrogen, $C_1$–$C_6$alkyl, $C_1$–$C_6$alkylsulfonyl, $C_1$–$C_6$alkylsulfoxy or $C_1$–$C_6$alkylthio;

$R^4$ is hydrogen, $C_{1-6}$alkyl, mono- or di($C_3$–$C_6$cycloalkyl)methyl, $C_3$–$C_6$cycloalkyl, $C_3$–$C_6$alkenyl, hydroxy$C_1$–$C_6$alkyl, $C_1$–$C_6$alkylcarbonyloxy$C_1$–$C_6$alkyl or $C_1$–$C_6$alkyloxy$C_1$–$C_6$alkyl;

$R^5$ is $C_1$–$C_8$alkyl, mono- or di($C_3$–$C_6$cycloalkyl)methyl, $Ar^1CH_2$, $C_3$–$C_6$alkenyl, $C_1$–$C_6$alkyloxy$C_1$–$C_6$alkyl, hydroxy$C_1$–$C_6$alkyl, thienylmethyl, furanylmethyl, $C_1$–$C_6$alkylthio$C_1$–$C_6$alkyl, morpholinyl, mono- or di($C_1$–$C_6$alkyl)amino$C_1$–$C_6$alkyl, di($C_1$–$C_6$alkyl)amino, $C_1$–$C_6$alkylcarbonyl$C_1$–$C_6$alkyl, $C_1$–$C_6$alkyl substituted with imidazolyl; or a radical of formula —Alk—O—CO—Ar I;

or $R^4$ and $R^5$ taken together with the nitrogen atom to which they are attached may form a pyrrolidinyl, piperidinyl, homopiperidinyl or morpholinyl group, optionally substituted with $C_1$–$C_6$alkyl or $C_1$–$C_6$alkyloxy$C_1$–$C_6$alkyl;

Ar is phenyl; phenyl substituted with 1, 2 or 3 substituents independently selected from halo, $C_1$–$C_6$alkyl, trifluoromethyl, hydroxy, cyano, $C_1$–$C_6$alkyloxy, benzyloxy, $C_1$–$C_6$alkylthio, nitro, amino and mono- or di($C_1$–$C_6$alkyl)amino; pyridinyl; pyridinyl substituted with 1, 2 or 3 substituents independently selected from halo, $C_1$–$C_6$alkyl, trifluoromethyl, hydroxy, cyano, $C_1$–$C_6$alkyloxy, benzyloxy, $C_1$–$C_6$alkylthio, nitro, amino, mono- or di($C_1$–$C_6$alkyl)amino and piperidinyl; and wherein said substituted phenyl may optionally be further substituted with one or more halogens;

$Ar^1$ is phenyl; phenyl substituted with 1, 2 or 3 substituents each independently selected from halo, $C_1$–$C_6$alkyl, $C_1$–$C_6$alkyloxy, di($C_1$–$C_6$alkyl)amino$C_1$–$C_6$alkyl trifluoromethyl, and $C_1$–$C_6$alkyl substituted with morpholinyl; or pyridinyl; and Alk is $C_1$–$C_6$alkanediyl.

Preferred compounds of this group include those wherein:

i) $R^2$ is methyl;

ii) $R^2$ is methyl; and Ar is substituted phenyl or 3-pyridyl;

iii) $R^2$ is methyl; $R^3$ is methyl; and Ar is substituted phenyl or 3-pyridyl XIII. CRF antagonists of the following formula, disclosed in EP 0773023, may also be employed:

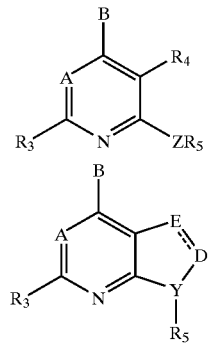

or a pharmaceutically acceptable salt thereof, wherein the dashed line represents an optional double bond;

A is —$CR_7$ or N;

B is —$NR_1R_2$, —$CR_1R_2R_{11}$, —$C(=CR_1R_{12})R_2$, —$NHCR_{11}R_1R_2$, —$OCR_{11}R_1R_2$, —$SCR_{11}R_1R_2$, —$CR_{11}R_2OR_1$, —$CR_{11}R_2SR_1$, —$C(S)R_2$, —$NHNR_1R_2$, —$CR_2R_{11}NHR_1$ or —$C(O)R_2$;

D is N or —$CR_{10}$ when a double bond connects E and D and E is —$CR_4$; —$CR_{10}$ when a double bond connects E and D and E is N; or —$CR_8R_9$, —$CHR_{10}$, —C=O, —C=S, —C=NH, or —C=$NCH_3$ when a single bond connects E and D;

E is —$CR_4$ or N when a double bond connects E and D, and E is —$CR_4R_6$ or —$NR_6$ when a single bond connects E and D;

Y is N or —CH;

Z is NH, O, S, —N($C_1$–$C_2$ alkyl), or —$CR_{12}R_{13}$, wherein $R_{12}$ and $R_{13}$ are each, independently, hydrogen, trifluoromethyl, or methyl, or one of $R_{12}$ and $R_{13}$ is cyano and the other is hydrogen or methyl;

$R_1$ is hydrogen or $C_1$–$C_6$ alkyl which is optionally substituted with up to two substituents independently selected from hydroxy, cyano, nitro, fluoro, chloro, bromo, iodo, $CF_3$, $C_1$–$C_4$ alkoxy, —O—CO—($C_1$–$C_4$ alkyl), —O—CO—NH($C_1$–$C_4$ alkyl), —O—CO—N($C_1$–$C_4$ alkyl)($C_1$–$C_2$ alkyl), —NH($C_1$–$C_4$ alkyl), —N($C_1$–$C_2$ alkyl)($C_1$–$C_4$ alkyl), —S($C_1$–$C_4$ alkyl), —N($C_1$–$C_4$alkyl)CO($C_1$–$C_4$ alkyl), —NHCO($C_1$–$C_4$ alkyl), —$CO_2$($C_1$–$C_4$ alkyl), —CONH($C_1$–$C_4$ alkyl), —CON($C_1$–$C_4$ alkyl)($C_1$–$C_2$ alkyl), ($C_1$–$C_4$ alkyl)sulfinyl, ($C_1$–$C_4$ alkyl)sulfonyl, and ($C_1$–$C_4$ alkyl)sulfanyl, and wherein said $C_1$–$C_6$ alkyl, $C_1$–$C_4$ alkoxy, and $C_1$–$C_4$ alkyl moieties in the foregoing $R_1$ groups optionally contain one double or triple bond;

$R_2$ is $C_1$–$C_6$ alkyl, heteroaryl, aryl, heteroaryl ($C_1$–$C_4$ alkyl), or aryl ($C_1$–$C_4$ alkyl), wherein said aryl and the aryl moiety of said (aryl)$C_1$–$C_4$ alkyl are selected from the group consisting of phenyl and naphthyl, and said heteroaryl and the heteroaryl moiety of said (heteroaryl)$C_1$–$C_4$ alkyl is selected from the group consisting of thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl; or $R^2$ is $C_3$–$C_8$ cycloalkyl or ($C_3$–$C_8$ cycloalkyl)$C_1$–$C_6$ alkyl, wherein one or two of the ring carbons of said cycloalkyl having at least 4 ring members and the cycloalkyl moiety of said ($C_3$–$C_8$ cycloalkyl)$C_1$–$C_6$ alkyl having at least 4 ring members is optionally replaced by an oxygen or sulfur atom or by —$NR_{14}$ wherein $R_{14}$ is hydrogen or $C_1$–$C_4$ alkyl; and wherein each of the foregoing $R_2$ groups is optionally substituted by up to three substituents independently selected from chloro, fluoro, and $C_1$–$C_4$ alkyl, or by one substituent selected from bromo, iodo, cyano, nitro, $C_1$–$C_6$ alkoxy, —O—CO—($C_1$–$C_4$ alkyl), —CO—N($C_1$–$C_4$ alkyl)($C_1$–$C_2$ alkyl), —$CO_2$($C_1$–$C_4$ alkyl), ($C_1$–$C_4$ alkyl)sulfanyl, ($C_1$–$C_4$ alkyl)sulfinyl, and ($C_1$–$C_4$ alkyl)sulfanyl, and wherein said $C_1$–$C_4$ alkyl and $C_1$–$C_6$ alkyl moieties of the foregoing $R_2$ groups optionally contain one carbon-carbon double or triple bond;

or $R^1$ and $R^2$ of said —$NR_1R_2$ and said —$CR_1R_2R_{11}$ are taken together to form a saturated or partially saturated 5- to 8-membered ring, wherein said ring optionally contains one or two carbon-carbon double bonds, and wherein one or two of the ring carbons is optionally replaced by a heteroatom selected from O, S, and N;

$R_3$ is hydrogen, $C_1$–$C_6$ alkyl, fluoro, chloro, bromo, iodo, hydroxy, amino, SH, —NH($C_1$–$C_4$ alkyl), —N($C_1$–$C_4$ alkyl)($C_1$–$C_2$ alkyl), —$CH_2OH$, —$CH_2OCH_3$, —($C_1$–$C_4$ alkyl), ($C_1$–$C_4$ alkyl)sulfanyl, ($C_1$–$C_4$ alkyl)sulfonyl, or ($C_1$–$C_4$ alkyl)sulfinyl, wherein said $C_1$–$C_6$ alkyl and $C_1$–$C_4$ alkyl moieties of the foregoing $R_3$ groups optionally contain one double or triple bond and are optionally substituted by from one to three substituents independently selected from hydroxy, amino, $C_1$–$C_3$ alkoxy, —NH($C_1$–$C_2$ alkyl), —N($C_1$–$C_2$ alkyl)$_2$, —$NHCOCH_3$, fluoro, chloro, and $C_1$–$C_3$ thioalkyl;

$R_4$ is hydrogen, $C_1$–$C_6$ alkyl, fluoro, chloro, bromo, iodo, $C_1$–$C_6$ alkoxy, formyl, trifluoromethoxy, —$CH_2OCH_3$, —$CH_2OCH_2CH_3$, —$CH_2CH_2OCH_3$, —$CH_2CF_3$, amino, nitro, —NH($C_1$–$C_4$ alkyl), —N($CH_3$)$_2$, —$NHCOCH_3$, —$NHCONHCH_3$, ($C_1$–$C_4$ alkyl)sulfanyl, ($C_1$–$C_4$ alkyl)sulfinyl, ($C_1$–$C_4$ alkyl)sulfonyl, cyano, hydroxy, —CO($C_1$–$C_4$ alkyl), —CHO, or —$CO_2$($C_1$–$C_4$ alkyl), wherein said $C_1$–$C_6$ alkyl, $C_1$–$C_6$ alkoxy, and $C_1$–$C_4$ alkyl moieties of the foregoing $R_4$ groups optionally contain one double or triple bond and are optionally substituted with one substituent selected from hydroxy, amino, —$NHCOCH_3$, —NH($C_1$–$C_2$ alkyl), —N($C_1$–$C_2$ alkyl)$_2$, —$O_2$($C_1$–$C_4$ alkyl), —CO($C_1$–$C_4$ alkyl), $C_1$–$C_3$ alkoxy, ($C_1$–$C_3$ alkyl)sulfanyl, fluoro, chloro, cyano, and nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or a 3- to 8-membered cycloalkyl ring or a 9- to 12-membered bicycloalkyl ring system, wherein said cycloalkyl ring and said bicycloalkyl ring system optionally contain one or two of O, S, or —N—G wherein G is hydrogen, $C_1$–$C_4$ alkyl, $C_1$–$C_4$ alkanoyl, phenyl, or benzyl, wherein each of the above $R_5$ groups is optionally substituted by up to three substituents independently selected from fluoro, chloro, $C_1$–$C_6$ alkyl, $C_1$–$C_6$ alkoxy, and trifluoromethyl, or one substituent selected from bromo, iodo, cyano, nitro, amino, —NH($C_1$–$C_4$ alkyl), —N($C_1$–$C_4$ alkyl)($C_1$–$C_2$ alkyl), —$CO_2$($C_1$–$C_4$ alkyl), —CO($C_1$–$C_4$ alkyl), —$SO_2NH$($C_1$–$C_4$ alkyl), —$SO_2N$($C_1$–$C_4$ alkyl)($C_1$–$C_2$ alkyl), —$SO_2NH_2$, —$NHSO_2$($C_1$–$C_4$ alkyl), —S($C_1$–$C_4$ alkyl), and —$SO_2$($C_1$–$C_4$ alkyl), wherein said $C_1$–$C_4$ alkyl and $C_1$–$C_6$ alkyl moieties of the foregoing $R_5$ groups optionally contain one double or triple bond and are optionally substituted by one or two substituents independently selected from fluoro, chloro, hydroxy, amino, methylamino, dimethylamino, and acetyl;

$R_6$ is hydrogen or $C_1$–$C_6$ alkyl, wherein said $C_1$–$C_6$ alkyl is optionally substituted by a single hydroxy, methoxy, ethoxy, or fluoro group;

$R_7$ is hydrogen, $C_1$–$C_4$ alkyl, fluoro, chloro, bromo, iodo, cyano, hydroxy, $C_1$–$C_4$ alkoxy, —CO($C_1$–$C_4$ alkyl), —$CO_2$($C_1$–$C_4$ alkyl), —$OCF_3$, $CF_3$, —$CH_2OH$, —$CH_2OCH_3$, or —$CH_2OCH_2CH_3$;

$R_8$ and $R_9$ are each, independently, hydrogen, hydroxy, methyl, ethyl, methoxy, or ethoxy;

or $R_8$ and $R_9$ together form an oxo (=O) group;

$R_{10}$ is hydrogen, $C_1$–$C_6$ alkyl, fluoro, chloro, bromo, iodo, $C_1$–$C_6$ alkoxy, formyl, amino, —NH($C_1$–$C_4$ alkyl), —N($C_1$–$C_4$ alkyl)($C_1$–$C_2$ alkyl), cyano, carboxy, amido, or —$SO_n$($C_1$–$C_4$ alkyl) wherein n is 0, 1, or 2, wherein said $C_1$–$C_6$ alkyl and $C_1$–$C_4$ alkyl moieties of the foregoing $R_{10}$ groups are optionally substituted by one of hydroxy, trifluoromethyl, amino, carboxy, amido, —NHCO($C_1$–$C_4$ alkyl), —NH($C_1$–$C_4$ alkyl), —N($C_1$–$C_4$ alkyl)($C_1$–$C_2$ alkyl), —$CO_2$($C_1$–$C_4$ alkyl), $C_1$–$C_3$ alkoxy, $C_1$–$C_3$ thioalkyl, fluoro, bromo, chloro, iodo, cyano, or nitro; and $R_{11}$ is hydrogen, hydroxy, fluoro, or methoxy.

Specific CRF antagonists useful in the practice of the present invention, include, without limitation, the following compounds:

4-(1-ethyl-propoxy)-3,6-dimethyl-2-(2,4,6-trimethylphenoxy)-pyridine;

butyl-[2,5-dimethyl-7-(2,4,6-trimethylphenyl)-6,7-dihydro-5H-pyrrolo[2,3-d]pyrimidin-4-yl]-ethyl-amine;

4-(butyl-ethylamino)-2,5-dimethyl-7-(2,4,6-trimethylphenyl)-5,7-dihydro-pyrrolo[2,3-d]pyrimidin-6-one;

4-(1-ethylpropoxy)-2,5-dimethyl-6-(2,4,6-trimethylphenoxy)-pyrimidine;

N-butyl-N-ethyl-2,5-dimethyl-NN-(2,4,6-trimethylphenyl)-pyrimidine-4,6-diamine;

[4-(1-ethyl-propoxy)-3,6-dimethyl-pyridin-2-yl]-(2,4,6-trimethylphenyl)-amine;

6-(ethyl-propyl-amino)-2,7-dimethyl-9-(2,4,6-trimethylphenyl)-7,9-dihydro-purin-8-one;

3-{(4-methyl-benzyl)-[3,6-dimethyl-1-(2,4,6-trimethylphenyl)-1H-pyrazolo[3,4-d]pyrimidin-4-yl]-amino}-propan-1-ol;

diethyl-[6-methyl-3-methylsulfanyl-1-(2,4,6-trichlorophenyl)-1H-pyrazolo[3,4-d]pyrimidin-4-yl]-amine;

2-{butyl-[6-methyl-3-methylsulfanyl-1-(2,4,6-trichlorophenyl)-1H-pyrazolo[3,4-d]pyrimidin-4-yl]-amino}-ethanol;

dibutyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfonyl-1-(2,4,6-trichlorophenyl)-1H-pyrazolo[3,4-d]pyrimidin-4-yl]-amine;

butyl-cyclopropylmethyl-[6-methyl-3-methylsulfanyl-1-(2,4,6-trichlorophenyl)-1H-pyrazolo[3,4-d]pyrimidin-4-yl]-amine;

di-1-propyl-[6-methyl-3-methylsulfanyl-1-(2,4,6-trichlorophenyl)-1H-pyrazolo[3,4-d]pyrimidin-4-yl]-amine;

diallyl-[6-methyl-3-methylsulfanyl-1-(2,4,6-trichlorophenyl)-1H-pyrazolo[3,4-d]pyrimidin-4-yl]-amine;

butyl-ethyl-[6-chloro-3-methylsulfanyl-1-(2,4,6-trichlorophenyl)-1H-pyrazolo[3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl]-amine;

propyl-ethyl-[3,6-dimethyl-1-(2,4,6-trimethylphenyl)-1H-pyrazolo[3,4-d]pyrimidin-4-yl]-amine;

4-(1-ethyl-propyl)-6-methyl-3-methylsulfanyl-1-(2,4,6-trimethylphenyl)-1H-pyrazolo[3,4-d]pyrimidine;

n-butyl-ethyl-[2,5-dimethyl-7-(2,4,6-trimethylphenyl)-7H-pyrrolo[2,3-d]pyrimidin-4-yl]amine;

di-n-propyl-[2,5-dimethyl-7-(2,4,6-trimethylphenyl)-7H-pyrrolo[2,3-d]pyrimidin-4-yl]amine;

ethyl-n-propyl-[2,5-dimethyl-7-(2,4,6-trimethylphenyl)-7H-pyrrolo[2,3-d]pyrimidin-4-yl]amine;

diethyl-2,5-dimethyl-7-(2,4,6-trimethylphenyl)-7H-pyrrolo[2,3-d]pyrimidin-4-yl]amine;

n-butyl-ethyl-[2,5,6-trimethyl-7-(2,4,6-trimethylphenyl)-7H-pyrrolo[2,3-d]pyrimidin-4-yl]amine;

2-{N-n-butyl-N-[2,5-dimethyl-7-(2,4,6-trimethylphenyl)-7H-pyrrolo[2,3-d]pyrimidin-4-yl]amino}-ethanol;

4-(1-ethyl-propyl)-2,5,6-trimethyl-7-(2,4,6-trimethylphenyl)-7H-pyrrolo[2,3-d]pyrimidine;

n-butyl-ethyl-[2,5-dimethyl-7-(2,4-dimethylphenyl)-7H-pyrrolo[2,3-d]pyrimidin-4-yl]amine;

2,5-dimethyl-7-(2,4,6-trimethylphenyl)-7H-pyrrolo[2,3-d]pyrimidyl-4-yl]-(1-ethyl-propyl)amine;

butyl-[3,6-dimethyl-1-(2,4,6-trimethylphenyl)-1H-pyrazolo[3,4-b]pyridin-4-yl]-ethylamine;

[3,6-dimethyl-1-(2,4,6-trimethylphenyl)-1H-pyrazolo[3,4-b]pyridin-4-yl]-(1-methoxymethylpropyl)-amine;

4-(1-methoxymethylpropoxy)-3,6-dimethyl-1-(2,4,6-trimethylphenyl)-1H-pyrazolo[3,4-b]pyridine;

(1-ethylpropyl)-[3,5,6-trimethyl-1-(2,4,6-trimethylphenyl)-1H-pyrazolo[3,4-b]pyridin-4-yl]-amine;

4-(1-ethylpropoxy)-2,5-dimethyl-7-(2,4,6-trimethylphenyl)-7H-pyrrolo[2,3-b]pyridine;

4-(1-ethylpropoxy)-2,5,6-trimethyl-7-(2,4,6-trimethylphenyl)-7H-pyrrolo[2,3-b]pyridine;

4-(1-ethylpropoxy)-2,5-dimethyl-7-(2,6-dimethyl-4-bromophenyl)-7H-pyrrolo[2,3-b]pyridine;

2,5,6-trimethyl-7-(1-propylbutyl)-4-(2,4,6-trimethylphenoxy)-7H-pyrrolo[2,3-d]pyrimidine;

1-(1-ethylpropyl)-6-methyl-4-(2,4,6-trimethylphenylamino)-1,3-dihydro-imidazo[4,5-c]pyridin-2-one;

9-(1-ethylpropyl)-2-methyl-6-(2,4,6-trimethylphenylamino)-7,9-dihydro-purin-8-one;

1-(1-ethylpropyl)-6-methyl-4-(2,4,6-trimethylphenoxy)-1,3-dihydro-imidazo[4,5-c]pyridin-2-one;

1-(1-ethylpropyl)-6-methyl-4-(2,4,6-trimethylphenoxy)-1H-imidazo[4,5-c]pyridine;

1-(1-ethylpropyl)-3,6-dimethyl-4-(2,4,6-trimethylphenoxy)-1,3-dihydro-imidazo[4,5-c]pyridin-2-one;

1-(1-ethylpropyl)-3,6-dimethyl-4-(2,4,6-trimethylphenylamino)-1,3-dihydro-imidazo[4,5-c]pyridin-2-one;

1-(1-ethyl-propyl)-4,7-dimethyl-5-(2,4,6-trimethyl-phenoxy)-1,4-dihydro-2H-pyrido[3,4-b]pyrazin-3-one;

1-(1-ethyl-propyl)-4,7-dimethyl-5-(2,4,6-trimethyl-phenoxy)-1,2,3,4-tetrahydro-pyrido[3,4-b]pyrazine;

1-(1-ethyl-propyl)-7-methyl-5-(2,4,6-trimethyl-phenoxy)-1,2,3,4-tetrahydro-pyrido[3,4-b]pyrazine;

1-(1-ethyl-propyl)-7-methyl-2-oxo-5-(2,4,6-trimethyl-phenoxy)-1,2,3,4-tetra-hydro-[1,6]naphthyridine-3-carboxylic acid methyl ester;

1-(1-ethyl-propyl)-7-methyl-2-oxo-5-(2,4,6-trimethyl-phenoxy)-1,2,3,4-tetra-hydro-[1,6]naphthyridine-3-carboxylic acid isopropyl ester;

1-(1-ethyl-propyl)-7-methyl-5-(2,4,6-trimethyl-phenoxy)-3,4-dihydro-1H-[1,6]naphthyridin-2-one;

1-(1-ethyl-propyl)-7-methyl-5-(2,4,6-trimethyl-phenoxy)-1,2,3,4-tetrahydro-[1,6]naphthyridine;

1-(1-ethyl-propyl)-7-methyl-5-(2,4,6-trimethyl-phenoxy)-1,4-dihydro-2H-3-oxa-1,6-diaza-naphthalene;

1-(1-ethyl-propyl)-4,7-dimethyl-5-(2,4,6-trimethyl-phenoxy)-1,4-dihydro-2H-3-oxa-1,6-diaza-naphthalene;

1-(1-ethyl-propyl)-3,7-dimethyl-5-(2,4,6-trimethyl-phenoxy)-3,4-dihydro-1H-3-oxa-[1,6]-naphthyridin-2-one;

1-(1-ethyl-propyl)-3,3,6-trimethyl-4-(2,4,6-trimethyl-phenoxy)-2,3-dihydro-1H-pyrrolo[3,2-c]pyridine 7-(1-ethyl-propoxy)-5-methyl-3-(2,4,6-trimethyl-phenyl)-pyrazolo[1,5-a]pyrimidine;

[2,5-dimethyl-3-(2,4,6-trimethyl-phenyl)-pyrazolo[1,5-a]pyrimidin-7-yl]-(1-ethyl-propyl)-amine;

(1-ethyl-propyl)-[5-methyl-3-(2,4,6-trimethyl-phenyl)-pyrazolo[1,5-a]pyrimidin-7-yl]-amine;

7-(1-ethyl-propoxy)-2,5-dimethyl-3-(2,4,6-trimethyl-phenyl)-pyrazolo[1,5-a]pyrimidine;

[2,5-dimethyl-3-(2,4,6-trimethyl-phenyl)-pyrazolo[1,5-a]pyrimidin-7-yl]-ethyl-propyl-amine;

[6-bromo-5-bromomethyl-3-(2,4,6-trimethyl-phenyl)-3H-[1,2,3]triazolo[4,5-b]pyridin-7-yl]-(1-ethyl-propyl)-amine;

(1-ethyl-propyl)-[5-methyl-3-(2,4,6-trimethyl-phenyl)-3H-[1,2,3]triazolo[4,5-b]pyridin-7-yl]-amine;

[6-bromo-5-methyl-3-(2,4,6-trimethyl-phenyl)-3H-[1,2,3]triazolo[4,5-b]pyridin-7-yl]-(1-ethyl-propyl)-methyl-amine;

7-(1-ethyl-propoxy)-5-methyl-3-(2,4,6-trimethyl-phenyl)-3H-[1,2,3]triazolo[4,5-b]pyridine;

4-(1-ethyl-propoxy)-2,5-dimethyl-7-(2,4,6-trimethyl-phenyl)-5H-pyrrolo[3,2-d]pyrimidine;

(±)-2,5-dimethyl-4-(tetrahydro-furan-3-yloxy)-7-(2,4,6-trimethyl-phenyl)-5H-pyrrolo-[3,2-d]pyrimidine;

2,5-dimethyl-4-(S)-(tetrahydro-furan-3-yloxy)-7-(2,4,6-trimethyl-phenyl)-5H-pyrrolo[3,2-d]pyrimidine;

2,5-dimethyl-4-(1-propyl-butoxy)-7-(2,4,6-trimethyl-phenyl)-5H-pyrrolo[3,2-d]pyrimidine;

4-sec-butylsulfanyl-2,5-dimethyl-7-(2,4,6-trimethyl-phenyl)-5H-pyrrolo[3,2-d]pyrimidine;

4-(butyl-ethyl-amino)-2,6-dimethyl-8-(2,4,6-trimethyl-phenyl)-5,8-dihydro-6H-pyrido[2,3-d]pyrimidin-7-one;

8-(1-ethyl-propoxy)-6-methyl-4-(2,4,6-trimethyl-phenyl)-3,4-dihydro-1H-pyrido[2,3-b]pyrazin-2-one;

8-(1-ethyl-propoxy)-6-methyl-4-(2,4,6-trimethyl-phenyl)-1,2,3,4-tetrahydro-pyrido[2,3-b]pyrazine;

4-(1-ethyl-propoxy)-2-methyl-8-(2,4,6-trimethyl-phenyl)-quinoline;

5-(1-ethyl-propoxy)-7-methyl-1-(2,4,6-trimethyl-phenyl)-1,4-dihydro-2H-3-oxa-1,8-diaza-naphthalene;

5-(1-ethyl-propoxy)-7-methyl-1-(2,4,6-trimethyl-phenyl)-1,2-dihydro-3-oxa-1,8-diaza-naphthalen-4-one;

8-(1-ethyl-propoxy)-1,6-dimethyl-4-(2,4,6-trimethyl-phenyl)-1,2,3,4-tetrahydro-pyrido[2,3-b]pyrazine;

(1-ethyl-propyl)-[2-methyl-8-(2,4,6-trimethyl-phenyl)-quinolin-4-yl]-amine;

4-(butyl-ethyl-amino)-2,6-dimethyl-8-(2,6-dimethyl-4-bromo-phenyl)-5,8-dihydro-6H-pyrido[2,3-d]pyrimidin-7-one;

4-(butyl-ethyl-amino)-2-methyl-8-(2,6-dimethyl-4-bromo-phenyl)-5,8-dihydro-6H-pyrido[2,3-d]pyrimidin-7-one;

4-(1-ethyl-propoxy)-2-methyl-8-(2,6-dimethyl-4-bromo-phenyl)-5,8-dihydro-6H-pyrido[2,3-d]pyrimidin-7-one;

(butyl-ethyl)-[2-methyl-8-(2,6-dimethyl-4-bromo-phenyl)-5,6,7,8-tetrahydro-pyrido[2,3-d]pyrimidin-4-yl]-amine;

(propyl-ethyl)-[2-methyl-8-(2,6-dimethyl-4-bromo-phenyl)-5,6,7,8-tetrahydro-pyrido[2,3-d]pyrimidin-4-yl]-amine;

(diethyl)-[2-methyl-8-(2,6-dimethyl-4-bromo-phenyl)-5,6,7,8-tetrahydro-pyrido[2,3-d]pyrimidin-4-yl]-amine;

(1-ethyl-propyl)-[2-methyl-8-(2,6-dimethyl-4-bromo-phenyl)-5,6,7,8-tetrahydro-pyrido[2,3-d]pyrimidin-4-yl]-amine;

(1-ethyl-propoxy)-2-methyl-8-(2,6-dimethyl-4-bromo-phenyl)-5,6,7,8-tetrahydro-pyrido[2,3-d]pyrimidine;

4-(butyl-ethyl-amino)-2-methyl-8-(2,4,6-trimethyl-phenyl)-5,8-dihydro-6H-pyrido[2,3-d]pyrimidin-7-one;

4-(1-ethyl-propoxy)-2-methyl-8-(2,4,6-trimethyl-phenyl)-5,8-dihydro-6H-pyrido[2,3-d]pyrimidin-7-one;

(butyl-ethyl)-[2-methyl-8-(2,4,6-trimethyl-phenyl)-5,6,7,8-tetrahydro-pyrido[2,3-d]pyrimidin-4-yl]-amine;

(propyl-ethyl)-[2-methyl-8-(2,4,6-trimethyl-phenyl)-5,6,7,8-tetrahydro-pyrido-[2,3-d]pyrimidin-4-yl]-amine;

(diethyl)-[2-methyl-8-(2,4,6-trimethyl-phenyl)-5,6,7,8-tetrahydro-pyrido[2,3-d]pyrimidin-4-yl]-amine;

(1-ethyl-propyl)-[2-methyl-8-(2,4,6-trimethyl-phenyl)-5,6,7,8-tetrahydro-pyrido[2,3-d]pyrimidin-4-yl]-amine;

(1-ethyl-propoxy)-2-methyl-8-(2,4,6-trimethyl-phenyl)-5,6,7,8-tetrahydro-pyrido[2,3-d]pyrimidine;

8-(1-ethyl-propoxy)-6-methyl-4-(2,6-dimethyl-4-bromo-phenyl)-3,4-dihydro-1H-pyrido[2,3-b]pyrazin-2-one;

8-(1-ethyl-propoxy)-6-methyl-4-(2,6-dimethyl-4-bromo-phenyl)-1,2,3,4-tetrahydro-pyrido[2,3-b]pyrazine;

4-(1-ethyl-propoxy)-2-methyl-8-(2,6-dimethyl-4-bromo-phenyl)-quinoline;

5-(1-ethyl-propoxy)-7-methyl-1-(2,6-dimethyl-4-bromo-phenyl)-1,4-dihydro-2H-3-oxa-1,8-diaza-naphthalene;

5-(1-ethyl-propoxy)-7-methyl-1-(2,6-dimethyl-4-bromo-phenyl)-1,2-dihydro-3-oxa-1,8-diaza-naphthalen-4-one;

8-(1-ethyl-propoxy)-1,6-dimethyl-4-(2,6-dimethyl-4-bromo-phenyl)-1,2,3,4-tetrahydro-pyrido[2,3-b]pyrazine;

(1-ethyl-propyl)-[2-methyl-8-(2,6-dimethyl-4-bromo-phenyl)-quinolin-4-yl]-amine;

4-(butyl-ethyl-amino)-2,6-dimethyl-8-(2,6-dimethyl-4-chloro-phenyl)-5,8-dihydro-6H-pyrido[2,3-d]pyrimidin-7-one;

8-(1-ethyl-propoxy)-6-methyl-4-(2,6-dimethyl-4-chloro-phenyl)-3,4-dihydro-1H-pyrido[2,3-b]pyrazin-2-one;

8-(1-ethyl-propoxy)-6-methyl-4-(2,6-dimethyl-4-chloro-phenyl)-1,2,3,4-tetrahydro-pyrido[2,3-b]pyrazin;

4-(1-ethyl-propoxy)-2-methyl-8-(2,6-dimethyl-4-chloro-phenyl)-quinoline;

5-(1-ethyl-propoxy)-7-methyl-1-(2,6-dimethyl-4-chloro-phenyl)-1,4-dihydro-2H-3-oxa-1,8-diaza-naphthalene;

5-(1-ethyl-propoxy)-7-methyl-1-(2,6-dimethyl-4-chloro-phenyl)-1,2-dihydro-3-oxa-1,8-diaza-naphthalen-4-one;

8-(1-ethyl-propoxy)-1,6-dimethyl-4-(2,6-dimethyl-4-chloro-phenyl)-1,2,3,4-tetrahydro-pyrido[2,3-b]pyrazine;

(1-ethyl-propyl)-[2-methyl-8-(2,6-dimethyl-4-chloro-phenyl)-quinolin-4-yl]-amine;

8-(1-hydroxymethyl-propoxy)-6-methyl-4-(2,4,6-trimethyl-phenyl)-3,4-dihydro-1H-pyrido[2,3-b]pyrazin-2-one;

8-(1-hydroxymethyl-propylamino)-6-methyl-4-(2,4,6-trimethyl-phenyl)-3,4-dihydro-1H-pyrido[2,3-b]pyrazin-2-one;

8-(1-ethyl-propylamino)-6-methyl-4-(2,4,6-trimethyl-phenyl)-3,4-dihydro-1H-pyrido[2,3-b]pyrazin-2-one;

8-diethylamino-6-methyl-4-(2,4,6-trimethyl-phenyl)-3,4-dihydro-1H-pyrido-[2,3-b]pyrazin-2-one;

8-(ethyl-propyl-amino)-6-methyl-4-(2,4,6-trimethyl-phenyl)-3,4-dihydro-1H-pyrido[2,3-b]pyrazin-2-one;

8-(butyl-ethyl-amino)-6-methyl-4-(2,4,6-trimethyl-phenyl)-3,4-dihydro-1H-pyrido[2,3-b]pyrazin-2-one;

8-(1-hydroxymethyl-propoxy)-6-methyl-4-(2,4,6-trimethyl-phenyl)-1,2,3,4-tetrahydro-pyrido[2,3-b]pyrazine;

8-(1-hydroxymethyl-propylamino)-6-methyl-4-(2,4,6-trimethyl-phenyl)-1,2,3,4-tetrahydro-pyrido[2,3-b]pyrazine;

8-(1-ethyl-propylamino)-6-methyl-4-(2,4,6-trimethyl-phenyl)-1,2,3,4-tetrahydro-pyrido[2,3-b]pyrazine;

8-diethylamino-6-methyl-4-(2,4,6-trimethyl-phenyl)-1,2,3,4-tetrahydro-pyrido[2,3-b]pyrazine;

8-(ethyl-propyl-amino)-6-methyl-4-(2,4,6-trimethyl-phenyl)-1,2,3,4-tetrahydro-pyrido[2,3-b]pyrazine;

8-(butyl-ethyl-amino)-6-methyl-4-(2,4,6-trimethyl-phenyl)-1,2,3,4-tetrahydro-pyrido[2,3-b]pyrazine;

4-(1-hydroxymethyl-propoxy)-2-methyl-8-(2,4,6-trimethyl-phenyl)-quinoline;

4-(1-hydroxymethyl-propylamino)-2-methyl-8-(2,4,6-trimethyl-phenyl)-quinoline;

4-(1-ethyl-propylamino)-2-methyl-8-(2,4,6-trimethyl-phenyl)-quinoline;

4-diethylamino-2-methyl-8-(2,4,6-trimethyl-phenyl)-quinoline;

4-(ethyl-propyl-amino)-2-methyl-8-(2,4,6-trimethyl-phenyl)-quinoline;

4-(butyl-ethyl-amino)-2-methyl-8-(2,4,6-trimethyl-phenyl)-quinoline;

5-(1-hydroxymethyl-propoxy)-7-methyl-1-(2,4,6-trimethyl-phenyl)-1,4-dihydro-2H-3-oxa-1,8-diaza-naphthalene;

5-(1-hydroxymethyl-propylamino)-7-methyl-1-(2,4,6-trimethyl-phenyl)-1,4-dihydro-2H-3-oxa-1,8-diaza-naphthalene;

5-(1-ethyl-propylamino)-7-methyl-1-(2,4,6-trimethyl-phenyl)-1,4-dihydro-2H-3-oxa-1,8-diaza-naphthalene;

5-diethylamino-5-methyl-1-(2,4,6-trimethyl-phenyl)-1,4-dihydro-2H-3-oxa-1,8-diaza-naphthalene;

5-(ethyl-propyl-amino)-7-methyl-1-(2,4,6-trimethyl-phenyl)-1,4-dihydro-2H-3-oxa-1,8-diaza-naphthalene;

8-(butyl-ethyl-amino)-6-methyl-4-(2,4,6-trimethyl-phenyl)-1,4-dihydro-2H-3-oxa-1,8-diaza-naphthalene;

4-(2,4-dichlorophenyl)-5-methyl-2-[N-(1-(methoxymethyl)-1-(naphth-2-yl) methyl)-N-propylamino]thiazole;

oxalate of 4-(2,4-dichlorophenyl)-5-methyl-2-[N-(6-methoxyisoquinol-5-yl)-N-propylamino]thiazole;

oxalate of 4-(2-chloro-4-methoxyphenyl)-5-methyl-2-[N-(6-methylisoquinol-5-yl)-N-propylamino]thiazole;

4-(2-chloro-4-methoxyphenyl)-5-methyl-2-[N-(1-methoxycarbonylmethylindol-5-yl)-N-propylamino]thiazole;

oxalate of 4-(2-chloro-4-methoxyphenyl)-5-methyl-2-[N-(6-methoxyisoquinol-5-yl)-N-propylamino]thiazole;

oxalate of 4-(2-chloro-4-methoxyphenyl)-5-methyl-2-[N-(6-chloroisoquinol-5-yl)-N-propylamino]thiazole;

oxalate of 4-(2-chloro-4-methoxyphenyl)-5-methyl-2-[N-(6-methoxyisoquinol-5-yl)-N-propylamino]thiazole;

4-(2-chloro-4-methoxyphenyl)-5-methyl-2-[N-1-methoxynaphth-2-yl)-N-propylamino]thiazole;

oxalate of 4-(2-chloro-4-trifluoromethylphenyl)-5-methyl-2-[N-6-methoxyisoquinol-5-yl)-N-propylamino]thiazole;

chlorhydrate of 4-(2-chloro-4-methoxyphenyl)-5-methyl-2-[N-(2-ethoxynaphth-1-yl)-N-propylamino]thiazole;

chlorhydrate of 4-(2-chloro-4-methoxyphenyl)-5-methyl-2[N-(2,3-dimethylnaphth-1-yl)-N-propylamino]thiazole;

chlorhydrate of 4-(2-chloro-4-methoxyphenyl)-5-methyl-2-[N-(6-bromo-2-methoxynaphth-1-yl)-N-propylamino]thiazole;

chlorhydrate of 4-(2-chloro-4-methoxyphenyl)-5-methyl-2-[N-(2,6-dimethylnaphth-1-yl)-N-propylamino]thiazole;

chlorhydrate of 4-(2-chloro-4-methoxyphenyl)-5-methyl-2-[N-(1-(methoxymethyl)-1-(naphth-2-yl)methyl)-N-propylamino]thiazole;

chlorhydrate of 4-(2-chloro-4-methoxyphenyl)-5-methyl-2-[N-(1-(cyclopropyl)-1-(naphth-2-yl)methyl)-N-propylamino]thiazole;

3-(2,4-dichlorophenyl)-5-methyl-7(N-propyl-N-cyclopropanemethylamino)-pyrazolo[2,3-a]pyrimidine;

3-(2,4-dichlorophenyl)-5-methyl-7-(N-allyl-N-cyclopropanemethylamino)-pyrazolo[2,3-a]pyrimidine;

2-methylthio-3-(2,4-dichlorophenyl)-5-methyl-7-(N,N-diallylamino)-pyrazolo[2,3-a]pyrimidine;

2-methylthio-3-(2,4-dichlorophenyl)-5-methyl-7-(N-butyl-N-cyclopropane-methyl-amino)pyrazolo[2,3-a]pyrimidine;

2-methylthio-3-(2,4-dichlorophenyl)-5-methyl-7-(N-propyl-N-cyclopropane-methyl-amino)pyrazolo[2,3-a]pyrimidine;

2-methyl-3-(4-chlorophenyl)-5-methyl-7-(N,N-dipropylamino)-pyrazolo[2,3-a]pyrimidine;

3-[6-(dimethylamino)-3-pyridinyl]-2,5-dimethyl-N,N-dipropylpyrazolo[2,3-a]pyrimidin-7-amine;

3-[6-(dimethylamino)-4-methyl-3-pyridinyl]-2,5-dimethyl-N,N-dipropyl-pyrazolo[2,3-a]pyrimidine-7-amine;

3-(2,4-dimethoxyphenyl)-2,5-dimethyl-7-(N-propyl-N-methyloxyethylamino)-pyrazolo(2,3-a)pyrimidine;

3-[6-(dimethylamino)-4-methyl-3-pyridinyl]-2,5-dimethyl-N-propyl-N-cyclopropylmethyl-pyrazolo[2,3-a]pyrimidine-7-amine;

3-[6-(dimethylamino)-4-methyl-3-pyridinyl]-2,5-dimethyl-N-ethyl-N-cyclopropylmethyl-pyrazolo[2,3-a]pyrimidine-7-amine;

7-(N-diethylamino)-2,5-dimethyl-3-(2-methyl-4-methoxyphenyl-[1,5-a]-pyrazolopyrimidine;

7-(N-(3-cyanopropyl)-N-propylamino-2,5,dimethyl-3-(2,4-dimethylphenyl)-[1,5-a]-pyrazolopyrimidine;

[3,6-dimethyl-2-(2,4,6-trimethyl-phenoxy)-pyridin-4-yl]-(1-ethyl-propyl)-amine;

[2-(4-chloro-2,6-dimethyl-phenoxy)-3,6-dimethyl-pyridin-4-yl]-(1-ethyl-propyl)-amine;

cyclopropylmethyl-[3-(2,4-dimethyl-phenyl)-2,5-dimethyl-pyrazolo[1,5-a]pyrimidin-7-yl]-propyl-amine;

cyclopropylmethyl-[3-(2-methyl-4-chloro-phenyl)-2,5-dimethyl-pyrazolo[1,5-a]pyrimidin-7-yl]-propyl-amine;

cyclopropylmethyl-[3-(2,4-di-chloro-phenyl)-2,5-dimethyl-pyrazolo[1,5-a]pyrimidin-7-yl]-propyl-amine;

[3-(2-methyl-4-chloro-phenyl)-2,5-dimethyl-pyrazolo[1,5-a]pyrimidin-7-yl]-di-propyl-amine;

[2,5-dimethyl-3-(2,4-dimethyl-phenyl)-pyrazolo[1,5-a]pyrimidin-7-yl]-(1-ethyl-propyl)-amine;

[2,5-dimethyl-3-(2,4-dichloro-phenyl)-pyrazolo[1,5-a]pyrimidin-7-yl]-(1-ethyl-propyl)-amine; and 4-(1-ethyl-propylamino)-6-methyl-2-(2,4,6-trimethyl-phenoxy)-nicotinic acid methyl ester.

Even more particularly, specific CRF antagonists useful in the practice of the present invention include, without limitation, the following compounds:

4-(1-ethyl-propoxy)-3,6-dimethyl-2-(2,4,6-trimethylphenoxy)-pyridine;

4-(1-ethylpropoxy)-2,5-dimethyl-6-(2,4,6-trimethylphenoxy)-pyrimidine;

[4-(1-ethyl-propoxy)-3,6-dimethyl-pyridin-2-yl]-(2,4,6-trimethylphenyl)-amine;

3-{(4-methyl-benzyl)-[3,6-dimethyl-1-(2,4,6-trimethylphenyl)-1H-pyrazolo[3,4-d]pyrimidin-4-yl]-amino}-propan-1-ol;

propyl-ethyl-[3,6-dimethyl-1-(2,4,6-trimethylphenyl)-1H-pyrazolo[3,4-d]pyrimidin-4-yl]-amine;

ethyl-n-propyl-[2,5-dimethyl-7-(2,4,6-trimethylphenyl)-7H-pyrrolo[2,3-d]pyrimidin-4-yl]amine;

2-{N-n-butyl-N-[2,5-dimethyl-7-(2,4,6-trimethylphenyl)-7H-pyrrolo[2,3-d]pyrimidin-4-yl]amino}-ethanol;

[3,6-dimethyl-1-(2,4,6-trimethylphenyl)-1H-pyrazolo[3,4,b]pyridin-4-yl]-(1-methoxymethylpropy;)-amine;

4-(1-ethylpropoxy)-2,5-dimethyl-7-(2,4,6-trimethylphenyl)-7H-pyrrolo[2,3-b]pyridine;

2,5,6-trimethyl-7-(1-propylbutyl)-4-(2,4,6-trimethylphenoxy)-7H-pyrrolo[2,3-d]pyrimidine;

1-(1-ethylpropyl)-6-methyl-4-(2,4,6-trimethylphenoxy)-1,3-dihydro-imidazo[4,5-c]pyridin-2-one;

1-(1-ethyl-propyl)-4,7-dimethyl-5-(2,4,6-trimethyl-phenoxy)-1,4-dihydro-2H-pyrido[3,4-b]pyridin-3-one;

1-(1-ethyl-propyl)-4,7-dimethyl-5-(2,4,6-trimethyl-phenoxy)-1,2,3,4-tetrahydro-pyrido[3,4-b]pyridine;

1-(1-ethyl-propyl)-7-methyl-2-oxo-5-(2,4,6-trimethyl-phenoxy)-1,2,3,4-tetra-hydro-[1,6]naphthyridine-3-carboxylic acid isopropyl ester;

1-(1-ethyl-propyl)-7-methyl-5-(2,4,6-trimethyl-phenoxy)-1,4-dihydro-2H-3-oxa-1,6-diaza-naphthalene;

(1-ethyl-propyl)-[5-methyl-3-(2,4,6-trimethyl-phenyl)-pyrazolo[1,5-a]pyrimidin-7-yl]-amine;

7-(1-ethyl-propoxy)-2,5-dimethyl-3-(2,4,6-trimethyl-phenyl)-pyrazolo[1,5-a]pyrimidine;

4-(1-ethyl-propoxy)-2,5-dimethyl-7-(2,4,6-trimethyl-phenyl)-5H-pyrrolo[3,2-d]pyrimidine;

4-(butyl-ethyl-amino)-2,6-dimethyl-8-(2,4,6-trimethyl-phenyl)-5,8-dihydro-6H-pyrido[2,3-d]pyridin-7-one;

8-(1-ethyl-propoxy)-6-methyl-4-(2,4,6-trimethyl-phenyl)-1,2,3,4-tetrahydro-pyrido[2,3-b]pyrazine;

4-(1-ethyl-propoxy)-2-methyl-8-(2,4,6-trimethyl-phenyl)-quinoline;

(1-ethyl-propyl)-[2-methyl-8-(2,4,6-trimethyl-phenyl)-quinolin-4-yl]-amine;

(propyl-ethyl)-[2-methyl-8-(2,4,6-trimethyl-phenyl)-5,6,7,8-tetrahydro-pyrido-[2,3-d]pyrimidin-4-yl]-amine;

(1-ethyl-propoxy)-2-methyl-8-(2,4,6-trimethyl-phenyl)-5,6,7,8-tetrahydro-pyrido[2,3-d]pyrimidine;

8-(1-hydroxymethyl-propylamino)-6-methyl-4-(2,4,6-trimethyl-phenyl)-3,4-dihydro-1H-pyrido[2,3-b]pyrazin-2-one;

4-(1-hydroxymethyl-propylamino)-2-methyl-8-(2,4,6-trimethyl-phenyl)-quinoline;

5-(1-hydroxymethyl-propylamino)-7-methyl-1-(2,4,6-trimethyl-phenyl)-1,4-dihydro-2H-3-oxa-1,8-diaza-naphthalene;

[3,6-dimethyl-2-(2,4,6-trimethyl-phenoxy)-pyridin-4-yl]-(1-ethyl-propyl)-amine;

cyclopropylmethyl-[3-(2,4-dimethyl-phenyl)-2,5-dimethyl-pyrazolo[1,5-a]pyrimidin-7-yl]-propyl-amine;

[2,5-dimethyl-3-(2,4-dimethyl-phenyl)-pyrazolo[1,5-a]pyrimidin-7-yl]-(1-ethyl-propyl)-amine;

3-[6-(dimethylamino)-3-pyridinyl-2,5-dimethyl-N,N-dipropylpyrazolo[2,3-a]pyrimidin-7-amine;

3-[6-(dimethylamino)-4-methyl-3-pyridinyl]-2,5-dimethyl-N,N-dipropyl-pyrazolo[2,3-a]pyrimidine-7-amine;

3-(2,4-dimethoxyphenyl)-2,5-dimethyl-7-(N-propyl-N-methyloxyethylamino)-pyrazolo(2,3-a)pyrimidine;

7-(N-diethylamino)-2,5-dimethyl-3-(2-methyl-4-methoxyphenyl-[1,5-a]-pyrazolopyrimidine;

7-(N-(3-cyanopropyl)-N-propylamino-2,5,dimethyl-3-(2,4-dimethylphenyl)-[1,5-a]-pyrazolopyrimidine.

Methods for making the CRF antagonists described above are disclosed in the above-listed patents and published patent applications incorporated by reference herein.

In one aspect of the present invention, a CRF antagonist may be used in combination with a GR antagonist. The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for the anti-inflammatory acrivity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. As defined above, a glucocorticoid receptor (GR) antagonist refers to a compound that binds to the receptor and prevents a glucocorticoid receptor agonist from binding and eliciting GR mediated events, including transcription. RU486 is an example of a non-selective glucocorticoid receptor antagonist.

Any GR antagonist can be used to practice the present invention, including those that are described in commonly assigned: International patent application PCT/IB00/00366, filed Mar. 27, 2000, which published as International patent publication WO 00/66522; U.S. Pat. No. 5,696,127; International patent publications WO 99/41256 and WO 99/41257; U.S. Pat. No. 5,696,127; European patent publication 188396; European patent publication 683172; International patent publication WO 98/26783; International patent publication WO 98/27986; International patent publication WO 98/31702; European patent publication 903146; and International patent publications WO 99/41256 and WO 99/41257. As noted above, the texts of all of these publications are incorporated by reference herein in their entireties.

Following are listed particular examples of GR antagonists that may be used in practicing the present invention. It is understood that the variables, e.g., "A", "B", "R$_1$", "R$_2$", etc., employed in the generic formula IA below have the meanings attributed to them only with respect to that particular formula.

For example, the GR antagonists may be of the following structural formula IA, including the pharmaceutically acceptable salts thereof, as described in commonly assigned International patent application PCT/IB00/00366, filed Mar. 27, 2000, which published as International patent publication WO 00/66522:

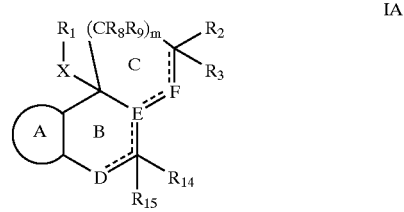

IA an isomer thereof, a prodrug of said compound or isomer, or a pharmaceutically acceptable salt of said compound, isomer or prodrug;

wherein m is 1 or 2;

- - - represents an optional bond;

A is selected from the group consisting of

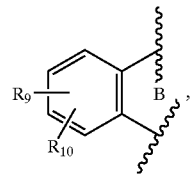
A-1

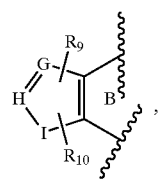
A-2

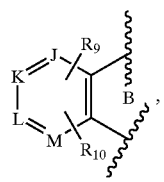
A-3

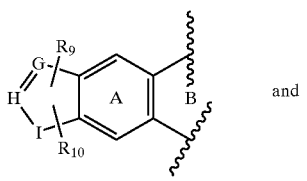
A-4 and

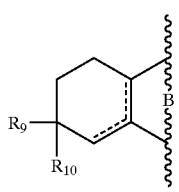
A-5

D is $CR_7$, $CR_7R_{16}$, N, $NR_7$ or O;

E is C, $CR_6$ or N;

F is $CR_4$, $CR_4R_5$ or O;

G, H and I together with 2 carbon atoms from the A-ring or 2 carbon atoms from the B-ring form a 5-membered heterocyclic ring comprising one or more N, O or S atoms; provided that there is at most one of O and S per ring; J, K, L and M together with 2 carbon atoms from the B-ring forms a 6-membered heterocyclic ring comprising 1 or more N atoms;

X is a) absent, b) —$CH_2$—, c) —CH(OH)— or d) —C(O)—;

$R_1$ is a) —H, b) —Z—$CF_3$, c) —($C_1$-$C_6$)alkyl, d) —($C_2$-$C_6$)alkenyl, e) —($C_2$-$C_6$)alkynyl, f) —CHO, g) —CH=N—$OR_{12}$, h) —Z—C(O)$OR_{12}$, i) —Z—C(O)—$NR_{12}R_{13}$, j) —Z—C(O)—$NR_{12}$—Z-het, k) —Z—$NR_{12}R_{13}$, l) —Z—$NR_{12}$het, m) —Z-het, n) —Z—O-het, o) —Z—O-aryl', p) —Z—O-aryl', q) —CHOH-aryl' or r) —C(O)-aryl' wherein aryl' in substituents o) to r) is substituted independently with 0, 1 or 2 of the following: —Z—OH, —Z—$NR_{12}R_{13}$, —Z—$NR_{12}$-het, —C(O)$NR_{12}R_{13}$, —C(O)O($C_1$-$C_6$)alkyl, —C(O)OH, —C(O)-het, —$NR_{12}$—C(O)—($C_1$-$C_6$)alkyl, —$NR_{12}$—C(O)—($C_2$-$C_6$)alkenyl, —$NR_{12}$—C(O)—($C_2$-$C_6$)alkynyl, —$NR_{12}$—C(O)—Z-het, —CN, —Z-het, —O—($C_1$-$C_3$)alkyl-C(O)—N$R_{12}R_{13}$, —O—($C_1$-$C_3$)alkyl-C(O)O($C_1$-$C_6$)alkyl, —$NR_{12}$—Z—C(O)O($C_1$-$C_6$)alkyl, —N(Z—C(O)O($C_1$-$C_6$)alkyl)$_2$, —$NR_{12}$—Z—C(O)—$NR_{12}R_{13}$, —Z—$NR_{12}$—$SO_2$—$R_{13}$, $NR_{12}$—$SO_2$-het, —C(O)H, —Z—$NR_{12}$—Z—O($C_1$-$C_6$)alkyl, —Z—$NR_{12}$—Z—$NR_{12}R_{13}$, —Z—$NR_{12}$—($C_1$-$C_6$)cycloalkyl, —Z—N(Z—O($C_1$-$C_6$)alkyl)$_2$, —$SO_2R_{12}$, —$SOR_{12}$, —$SR_{12}$, —$SO_2NR_{12}R_{13}$, —O—C(O)—($C_1$-$C_4$)alkyl, —O—$SO_2$—($C_1$-$C_4$)alkyl, -halo or —$CF_3$;

Z for each occurrence is independently a) —($C_0$-$C_6$)alkyl, b) —($C_2$-$C_6$)alkenyl or c) —($C_2$-$C_6$)alkynyl;

$R_2$ is a) —H, b) -halo, c) —OH, d) —($C_1$-$C_6$)alkyl substituted with 0 or 1—OH, e) —$NR_{12}R_{13}$, f) —Z—C(O)O($C_1$-$C_6$)alkyl, g) —Z—C(O)$NR_{12}R_{13}$, h) —O—($C_1$-$C_6$)alkyl, i) —Z—O—C(O)—($C_1$-$C_6$)alkyl, j) —Z—O—($C_1$-$C_3$)alkyl-C(O)—$NR_{12}R_{13}$, k) —Z—O—($C_1$-$C_3$)alkyl-C(O)—O($C_1$-$C_6$)alkyl, l) —O—($C_2$-$C_6$)alkenyl, m) —O—($C_2$-$C_6$)alkynyl, n) —O—Z-het, o) —COOH, p) —C(OH)$R_{12}R_{13}$ or q) —Z—CN;

$R_3$ is a) —H, b) —($C_1$-$C_{10}$)alkyl wherein 1 or 2 carbon atoms, other than the connecting carbon atom, may optionally be replaced with 1 or 2 heteroatoms independently selected from S, O and N and wherein each carbon atom is substituted with 0, 1 or 2 $R_y$, c) —($C_2$-$C_{10}$)alkenyl substituted with 0, 1 or 2 $R_y$, d) —($C_2$-$C_{10}$)alkynyl wherein 1 carbon atom, other than the connecting carbon atom, may optionally be replaced with 1 oxygen atom and wherein each carbon atom is substituted with 0, 1 or 2 $R_y$, e) —CH=C=$CH_2$, f) —CN, g) —($C_3$-$C_6$)cycloalkyl, h) —Z-aryl, i) —Z-het, j) —C(O)O($C_1$-$C_6$)alkyl, k) —O($C_1$-$C_6$)alkyl, l) —Z—S—$R_{12}$, m) —Z—S(O)—$R_{12}$, n) —Z—S(O)$_2$—$R_{12}$, o) —$CF_3$ p) —$NR_{12}$O—($C_1$-$C_6$)alkyl or q) —$CH_2OR_y$;

provided that one of $R_2$ and $R_3$ is absent when there is a double bond between $CR_2R_3$ (the 7 position) and the F moiety (the 8 position) of the C-ring;

$R_y$ for each occurrence is independently a) —OH, b) -halo, c) —Z—$CF_3$, d) —Z—CF($C_1$-$C_3$ alkyl)$_2$, e) —CN, f) —$NR_{12}R_{13}$, g) —($C_3$-$C_6$)cycloalkyl, h) —($C_3$-$C_6$)alkenyl, i) —(CO—$C_3$)alkyl-aryl, j) -het or k) —$N_3$;

or $R_2$ and $R_3$ are taken together to form a) =$CHR_{11}$, b) =$NOR_{11}$, c) =O, d) =N—$NR_{12}$, e) =N—$NR_{12}$—C(O)—$R_{12}$, f) oxiranyl or g) 1,3-dioxolan-4-yl;

$R_4$ and $R_5$ for each occurrence are independently a) —H, b) —CN, c) —($C_1$-$C_6$)alkyl substituted with 0 to 3 halo, d) —($C_2$-$C_6$)alkenyl substituted with 0 to 3 halo, e) —($C_2$-$C_6$)alkynyl substituted with 0 to 3 halo, f) —O—($C_1$-$C_6$)alkyl substituted with 0 to 3 halo, g) —O—($C_2$-$C_6$)alkenyl substituted with 0 to 3 halo, h) —O—($C_2$-$C_6$)alkynyl substituted with 0 to 3 halo, i) halo, j) —OH, k) ($C_3$-$C_6$)cycloalkyl or l) ($C_3$-$C_6$)cycloalkenyl;

or $R_4$ and $R_5$ are taken together to form =O;

$R_6$ is a) —H, b) —CN, c) —($C_1$-$C_6$)alkyl substituted with 0 to 3 halo, d) —($C_2$-$C_6$)alkenyl substituted with 0 to 3 halo, e) —($C_2$-$C_6$)alkynyl substituted with 0 to 3 halo or f) —OH;

$R_7$ and $R_{16}$ for each occurrence are independently a) —H, b) -halo, c) —CN, d) —($C_1$-$C_6$)alkyl substituted with 0 to 3 halo, e) —($C_2$-$C_6$)alkenyl substituted with 0 to 3 halo or f) —($C_2$-$C_6$)alkynyl substituted with 0 to 3 halo; provided that $R_7$ is other than —CN or -halo when D is $NR_7$;

or R$_7$ and R$_{16}$ are taken together to form =O;

R$_8$, R$_9$, R$_{14}$ and R$_{15}$ for each occurrence are independently a) —H, b) -halo, c) (C$_1$–C$_6$)alkyl substituted with 0 to 3 halo, d) —(C$_2$–C$_6$)alkenyl substituted with 0 to 3 halo, e) —(C$_2$–C$_6$)alkynyl substituted with 0 to 3 halo, f) —CN, g) —(C$_3$–C$_6$)cycloalkyl, h) —(C$_3$–C$_6$)cycloalkenyl, i) —OH, j) —O—(C$_1$–C$_6$)alkyl, k) —O—(C$_1$–C$_6$)alkenyl, l) —O—(C$_1$–C$_6$)alkynyl, m) —NR$_{12}$R$_{13}$, n) —C(O)OR$_{12}$ or o) —C(O)NR$_{12}$R$_{13}$;

or R$_8$ and R$_9$ are taken together on the C-ring to form =O; provided that when m is 2, only one set of R$_8$ and R$_9$ are taken together to form =O;

or R$_{14}$ and R$_{15}$ are taken together to form =O; provided that when R$_{14}$ and R$_{15}$ are taken together to form =O, D is other than CR$_7$ and E is other than C;

R$_{10}$ is a) —(C$_1$–C$_{10}$)alkyl substituted with 0 to 3 substituents independently selected from -halo, —OH and —N$_3$, b) —(C$_2$–C$_{10}$)alkenyl substituted with 0 to 3 substituents independently selected from -halo, —OH and —N$_3$, c) —(C$_2$–C$_{10}$)alkynyl substituted with 0 to 3 substituents independently selected from -halo, —OH and —N$_3$, d) -halo, e) —Z—CN, f) —OH, g) —Z-het, h) —Z—NR$_{12}$R$_{13}$, i) —Z—C(O)-het, j) —Z—C(O)—(C$_1$–C$_6$)alkyl, k) —Z—C(O)—NR$_{12}$R$_{13}$, l) —Z—C(O)—NR$_{12}$—Z—CN, m) —Z—C(O)—NR$_{12}$-Z-het, n) —Z—C(O)—NR$_{12}$—Z-aryl, o) —Z—C(O)—NR$_{12}$—Z—NR$_{12}$R$_{13}$, p) —Z—C(O)—NR$_{12}$—Z—O(C$_1$–C$_6$)alkyl, q) —(C$_1$–C$_6$)alkyl-C(O)OH, r) —Z—C(O)O(C$_1$–C$_6$)alkyl, s) —Z—O—(C$_0$–C$_6$)alkyl-het, t) —Z—O—(C$_0$–C$_6$)alkyl-aryl, u) —Z—O—(C$_1$–C$_6$)alkyl substituted with 0 to 2 R$_x$, v) —Z—O—(C$_1$–C$_6$)alkyl-CH(O), w) —Z—O—(C$_1$–C$_6$)alkyl-NR$_{12}$-het, x) —Z—O—Z-het-Z-het, y) —Z—O—Z-het-Z—NR$_{12}$R$_{33}$, z) —Z—O—Z-het-C(O)-het, a1) —Z—O—Z—C(O)-het, b1) —Z—O—Z—C(O)-het-het, c1) —Z—O—Z—C(O)—(C$_1$–C$_6$)alkyl, d1) —Z—O—Z—C(S)—NR$_{12}$R$_{13}$, e1) —Z—O—Z—C(O)—NR$_{12}$R$_{13}$, f1) —Z—O—Z—(C$_1$–C$_3$)alkyl-C(O)—NR$_{12}$R$_{13}$, g1) —Z—O—Z—C(O)—O(C$_1$–C$_6$)alkyl, h1) —Z—O—Z—C(O)—OH, i1) —Z—O—Z—C(O)—NR$_{12}$—O(C$_1$–C$_6$)alkyl, j1) —Z—O—Z—C(O)—NR$_{12}$—OH, k1) —Z—O—Z—C(O)—NR$_{12}$—Z—NR$_{12}$R$_{13}$, l1) —Z—O—Z—C(O)—NR$_{12}$—Z-het, m1) —Z—O—Z—C(O)—NR$_{12}$—SO$_2$—(C$_1$–C$_6$)alkyl, n1) —Z—O—Z—C(=NR$_{12}$)(NR$_{12}$R$_{13}$), o1) —Z—O—Z—C(=NOR$_{12}$)(NR$_{12}$R$_{13}$), p1) —Z—NR$_{12}$—C(O)—O—Z—NR$_{12}$R$_{13}$, q1) —Z—S—C(O)—NR$_{12}$R$_{13}$, r1) —Z—O—SO$_2$—(C$_1$–C$_6$)alkyl, s1) —Z—O—SO$_2$-aryl, t1) —Z—O—SO$_2$—NR$_{12}$R$_{13}$, u1) —Z—O—SO$_2$—CF$_3$, v1) —Z—NR$_{12}$C(O)OR$_{13}$ or w1) —Z—NR$_{12}$—C(O)R$_{13}$;

or R$_9$ and R$_{10}$ are taken together on the moiety of formula A-5 to form a) =O or b) =NOR$_{12}$;

R$_{11}$ is a) —H, b) —(C$_1$–C$_5$)alkyl, c) —(C$_3$–C$_6$)cycloalkyl or d) —(C$_0$–C$_3$)alkyl-aryl;

R$_{12}$ and R$_{13}$ for each occurrence are each independently a) —H, b) —(C$_1$–C$_6$)alkyl wherein 1 or 2 carbon atoms, other than the connecting carbon atom, may optionally be replaced with 1 or 2 heteroatoms independently selected from S, O and N and wherein each carbon atom is substituted with 0 to 6 halo, c) —(C$_2$–C$_6$)alkenyl substituted with 0 to 6 halo or d) —(C$_1$–C$_6$)alkynyl wherein 1 carbon atom, other than the connecting carbon atom, may optionally be replaced with 1 oxygen atom and wherein each carbon atom is substituted with 0 to 6 halo;

or R$_{12}$ and R$_{13}$ are taken together with N to form het;

or R$_6$ and R$_{14}$ or R$_{15}$ are taken together to form 1,3-dioxolanyl;

aryl is a) phenyl substituted with 0 to 3 R$_x$, b) naphthyl substituted with 0 to 3 R$_x$ or c) biphenyl substituted with 0 to 3 R$_x$;

het is a 5-, 6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle; and the nitrogen may be in the oxidized state giving the N-oxide form; and substituted with 0 to 3 R$_x$;

R$_x$ for each occurrence is independently a) -halo, b) —OH, c) —(C$_1$–C$_6$)alkyl, d) —(C$_2$–C$_6$)alkenyl, e) —(C$_2$–C$_6$)alkynyl, f) —O(C$_1$—C$_6$)alkyl, g) —O(C$_2$–C$_6$)alkenyl, h) —O(C$_2$–C$_6$)alkynyl, i) —(C$_0$–C$_6$)alkyl-NR$_{12}$R$_{13}$, j) —C(O)—NR$_{12}$R$_{13}$, k) —Z—SO$_2$R$_{12}$, l) —Z—SOR$_{12}$, m) —Z—SR$_{12}$, n) —NR$_{12}$—SO$_2$R$_{13}$, o) —NR$_{12}$—C(O)—R$_{13}$, p) —NR$_{12}$—OR$_{13}$, q) —SO$_2$—NR$_{12}$R$_{13}$, r) —CN, s) —CF$_3$, t) —C(O)(C$_1$–C$_6$)alkyl, u) =O, v) —Z—SO$_2$-phenyl or w) —Z—SO$_2$-het';

aryl' is phenyl, naphthyl or biphenyl;

het' is a 5-, 6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle;

provided that:

1) X—R$_1$ is other than hydrogen or methyl;
2) when R$_9$ and R$_{10}$ are substituents on the A-ring, they are other than mono- or di-methoxy;
3) when R$_2$ and R$_3$ are taken together to form =CHR$_{11}$ or =O wherein R$_{11}$ is —O(C$_1$–C$_6$)alkyl, then —X—R, is other than (C$_1$–C$_4$)alkyl;
4) when R$_2$ and R$_3$ taken together are C=O and R$_9$ is hydrogen on the A-ring; or when R$_2$ is hydroxy, R$_3$ hydrogen and R$_9$ is hydrogen on the A-ring, then R$_{10}$ is other than —O—(C$_1$–C$_6$)alkyl or —O—CH$_2$-phenyl at the 2-position of the A-ring;
5) when X—R$_1$ is (C$_1$–C$_4$)alkyl, (C$_2$–C$_4$)alkenyl or (C$_2$–C$_4$)alkynyl, R$_9$ and R$_{10}$ are other than monohydroxy or =O, including the diol form thereof, when taken together; and
6) when X is absent, R$_1$ is other than a moiety containing a heteroatom independently selected from N, O or S directly attached to the juncture of the B-ring and the C-ring.

The compounds of formula IA as described above, their pharmaceutically acceptable salts, and methods of preparing such compounds and salts are disclosed in commonly International patent application PCT/IB00/00366, filed Mar. 27, 2000. This application, referred to above, is incorporated herein by reference in its entirety.

Specific GR antagonists useful in the practice of the present invention include, without limitation, the following compounds:

2-phenanthrenecarboxamide, 4b,5,6,7,8,8a,9,10-octahydro-7-hydroxy-4b-(phenylmethyl)-7-(1-propynyl)-N-(4-pyridinylmethyl)-, [4bS-(4bα,7α,8aβ)]-;

2-phenanthrenecarboxamide, 4b,5,6,7,8,8a,9,10-octahydro-7-hydroxy-4b-(phenylmethyl)-7-(1-propynyl)-N-(2-pyridinyimethyl)-, [4bS-(4bα,7α,8αaβ)]-;

2-phenanthrenecarboxamide, 4b,5,6,7,8,8a,9,10-octahydro-7-hydroxy-4b-(phenylmethyl)-7-(1-propynyl)-N-(3-pyridinyimethyl)-, [4bS-(4bα,7α,8αaβ)]-;

carbamic acid, [2-(dimethylamino)ethyl]-, 4b,5,6,7,8,8a,9,10-octahydro-7-hydroxy-4b-(phenylmethyl)-7-(1-propynyl)-2-phenanthrenyl ester,[4bS-(4bα,7α,8αaβ)]-;

2-phenanthrenecarboxamide, 4b,5,6,7,8,8a,9,10-octahydro-7-hydroxy-4b-(phenylmethyl)-7-(1-propynyl)-N-(4-pyrazinyl-, [4bS-(4bα,7α,8αaβ)]-;

2-phenanthrenol, 1,2,3,4,4a,9,10,10a-octahydro-4a-(phenylmethyl)-2-(1-propynyl)-7-(1-propynyl)-N-(4-pyridinyimethyl)-, [2R-(2α4aα,10aβ)];

2-phenanthrenol, 1,2,3,4,4a,9,10,10a-octahydro-4a-(phenylmethyl)-2-(1-propynyl)-7-(4-pyridinyimethoxy)-, [2R-(2α4aα,10aβ)];

2-phenanthrenecarbonitrile, 4b,5,6,7,8,8a,9,10-octahydro-7-hydroxy-4b-(phenylmethyl)-7-(1-propynyl)-, [4bS-(4bα,7α,8αaβ)]-;

2-phenanthrenecarboxamide, 4b,5,6,7,8,8a,9,10-octahydro-7-hydroxy-N-[(2-methyl-3-pyridinyl)methyl]-4b-phenylmethyl)-7-(1-propynyl)-, [4bS-(4bα,7α,8αaβ)]-;

2-phenanthrenecarboxamide, 4b,5,6,7,8,8a,9,10-octahydro-7-hydroxy-N-[(2-methyl-3-pyridinyl)methyl]-4b-phenylmethyl)-7-(propyl)-, [4bS-(4bα,7α,8αaβ)]-;

2-phenanthrenecarboxamide, 4b,5,6,7,8,8a,9,10-octahydro-7-hydroxy-4b-(phenylmethyl)-7-phenylmethyl)-7-propyl-N-2-pyridinyl)methyl)-,[4bS-(4bα,7α,8αaβ)]-;

2-phenanthrenol, 1,2,3,4,4a,9,10,10a-octahydro-4a-(phenylmethyl)-7-(3-pyridinylmethoxy)-2-(3,3,3-trifluoropropyl)-, [2S-(2α,4aα,10aβ)]-;

2-phenanthrenol, 1,2,3,4,4a,9,10,10a-octahydro-7-[(2-methyl-3-pyridinyl)methoxy]-4a-(phenylmethyl)-2-(3,3,3-trifluoropropyl)-, [2S-(2α,4aα,10aβ)]-;

2-phenanthrenecarboxamide, 4b,5,6,7,8,8a,9,10-octahydro-7-hydroxy-N-[(2-methyl-3-pyridinyl)methyl]-4b-(phenylmethyl)-7-(3,3,3-trifluoropropyl)-, (4bS,7S,8aR);

2-phenanthrenecarboxamide, 4b,5,6,7,8,8a,9,10-octahydro-7-hydroxy-7-methyl-N-[(2-methyl-3-pyridinyl)methyl]-4b-(phenylmethyl)-, (4bS,7S,8aR);

2-phenanthrenecarboxamide, 4b,5,6,7,8,8a,9,10-octahydro-7-hydroxy-7-methyl-4b-(phenylmethyl)-N-3-pyridinyl-, (4bS,7S,8aR)-;

2-phenanthrenol, 1,2,3,4,4a,9, 10,10a-octahydro-7-[(2-methyl-3-pyridinyl)methoxy]-4a-(phenylmethyl)-2-(trifluoromethyl)-, (2R,4aS,10aR)-; and 2-phenanthrenecarboxamide, 4b, 5, 6, 7, 8, 8a, 9, 10-octahydro-7-hydroxy-N-[(2-methyl-3-pyridinyl)methyl]-4b-(phenylmethyl)-7-(trifluoromethyl)-, (4bS, 7R, 8aR)-.

Methods for making the GR antagonists described above are disclosed in the above listed patents, applications and published patent applications incorporated by reference herein.

Acid addition salts of the CRF antagonists and GR antagonists employed in the present invention can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The administration of the CRF antagonist and the GR antagonist, or pharmaceutically acceptable salts thereof, according to the present invention can be sequential in time or simultaneous, with the simultaneous method being generally preferred. For sequential administration, the CRF antagonist and the GR antagonist can be administered in any order. It is generally preferred that such administration be oral. It is even more preferred that the administration be oral and simultaneous. However, if the subject being treated is unable to swallow, or oral absorption is otherwise impaired or undesirable, another route of administration such as suppositories, parenteral (such as subcutaneous, intravenous, intramuscular, intrasternal and infusion techniques), or topical administration will be appropriate. When the CRF antagonist and the GR antagonist are administered sequentially, the administration of each can be by the same method or by different methods.

The pharmaceutical compositions of the present invention comprise amounts of a CRF antagonist alone or together with a GR antagonist. One aspect of the present invention provides compositions comprising amounts of a CRF antagonist and a GR antagonist which result in a therapeutic effect. Of such compositions, compositions comprising a CRF antagonist as disclosed in EP 0773023 (which is described above) or a pharmaceutically acceptable salt thereof, and a GR antagonist as disclosed in International patent application PCT/IB00/00366, filed Mar. 27, 2000 (which is described above) or a pharmaceutically acceptable salt thereof are preferred. It is further preferred that the compositions comprising the CRF antagonist and the GR antagonist be administered in the presence of a pharmaceutically acceptable vehicle, carrier or diluent, in either single or multiple doses.

Suitable pharmaceutical vehicles, carriers and diluents include inert solid diluents or fillers, sterile aqueous solutions, and various organic solvents. The pharmaceutical compositions formed by combining the active compound(s) and the pharmaceutically acceptable carriers are then readily administered in a variety of dosage forms such as tablets, powders, lozenges, syrups, injectable solutions, and the like. These pharmaceutical compositions can, if desired, contain additional ingredients such as flavorings, binders, excipients, and the like. Thus, for purposes of oral administration, tablets containing various excipients such as sodium citrate, calcium carbonate, and calcium phosphate may be employed along with various disintegrants such as starch, alginic acid, and certain complex silicates, together with binding agents such as polyvinylpyrrolidone, sucrose, gelatin, and acacia. Additionally, lubricating agents such as magnesium stearate, sodium lauryl sulfate, and talc are often useful for tabletting purposes. Solid compositions of a similar type can also be employed as fillers in soft and hard filled gelatin capsules. Preferred materials for this include lactose or milk sugar and high molecular weight polyethylene glycols. When aqueous suspensions or elixirs are desired for oral administration, the active ingredient(s) therein may be combined with various sweetening or flavoring agents, coloring matter or dyes and, if desired, emulsifying or suspending agents, together with diluents such as water, ethanol, propylene glycol, glycerin, and combinations thereof.

For parenteral administration, solutions of the active compound(s) in sesame or peanut oil, aqueous propylene glycol, or in sterile aqueous solution can be employed. Such aqueous solutions should be suitably buffered if necessary and the liquid diluent first rendered isotonic with sufficient saline or glucose. These particular aqueous solutions are especially suitable for intravenous, intramuscular, subcutaneous, and intraperitoneal administration. The sterile aqueous media employed are all readily available by standard techniques known to those skilled in the art.

For purposes of transdermal (e.g., topical) administration, dilute, sterile, aqueous or partially aqueous solutions (usually in about 0.1% to 5% concentration), otherwise similar to the above parenteral solutions, are employed.

Methods of preparing various pharmaceutical compositions with a certain amount of active ingredient(s) are known, or will be apparent in light of this disclosure, to those skilled in the art. For example, see Remington's Pharmaceutical Sciences, Mack Publishing Company, Easton, Pa., 19th Edition (1995).

A therapeutically effective amount of an active ingredient means an amount that ameliorates, attenuates, or eliminates one or more symptoms of a particular disease or condition or prevents or delays the onset of one of more symptoms of a particular disease or condition. Amount(s) of the CRF antagonist alone or in combination with the GR antagonist necessary to achieve the desired therapeutic effect according to the present invention are within the skill of those who practice in the art of having the benefit of the disclosure herein. Syndrome X-treating or preventing amount(s) of the CRF antagonist alone or in combination with the GR antagonist are preferred.

In general, the effective dosage for the CRF antagonist employed in the present invention will depend on the intended route of administration and factors such as the age and weight of the patient, as generally known to a physician. The dosage will also depend on the particular condition to be treated and will generally range from about 0.1 to about 300 mg/kg body weight of the patient per day, with administration carried out in single or divided dosages.

In general, the effective dosage for the GR antagonist employed in the present invention will range from about 0.1 $\mu$g/kg of body weight to about 500 mg/kg of body weight, more particularly from about 1 $\mu$g/kg to about 250 mg/kg, and most particularly from about 2 $\mu$g/kg to about 100 mg/kg. More preferably, the GR antagonist will be administered at an amount of about 0.1 mg/kg to about 500 mg/kg of body weight, and most preferably from about 0.1 mg/kg to about 50 mg/kg of body weight. As recognized by those skilled in the art, the particular quantity of the GR antagonist to be administered to a patient according to the present invention will depend upon a number of factors, including, without limitation, the biological activity desired, the condition of the patient, and tolerance for the drug.

The methods and compositions of the present invention have utility in the treatment or prevention of Syndrome X in animals, such as dogs, cats, cows, horses, sheep, and humans. Particularly preferred animals are mammals, including both males and females. As such, the methods and compositions of the present invention have utility in the treatment or prevention of Syndrome X in companion animals, such as dogs and cats. The administration of the compositions of this invention may be effected orally or parenterally. An amount of a composition of the invention is administered such that an effective dose is received, usually a daily dose.

Conveniently, the medicaments can be carried in the drinking water such that a therapeutic dosage of the agent(s) is ingested with the daily water supply. The agent(s) can be directly metered into drinking water, preferably in the form of a liquid, water-soluble concentrate, such as an aqeuous solution of a water-soluble salt.

Conveniently, the active ingredient(s) can also be added directly to the companion animal's feed, as such, or in the form of an animal feed supplement, also referred to as a premix or concentrate. A premix or concentrate of the therapeutic agent(s) in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and various mineral mixes. A particularly effective carrier is the respective animal feed itself, i.e., a small portion of such feed. The carrier facilitates uniform distribution of the active material(s) in the finished feed with which the premix is blended. It is important that the compound(s) be thoroughly blended into the premix and, subsequently, the feed. In this respect, the agent(s) may be dispersed or dissolved in a suitable oily vehicle such as soybean oil, corn oil, cottonseed oil, and the like, or in a volatile organic solvent and then blended with the carrier. It will be appreciated that the proportions of active material(s) in the concentrate are capable of wide variation since the amount of agent(s) in the finished feed may be adjusted by blending the appropriate proportion of premix with the feed to obtain a desired level of the therapeutic agent(s).

High potency concentrates may be blended by the feed manufacturer with a proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective amount of the compound(s) according to the present invention. The mixtures are thoroughly blended by standard procedures, such as in a twin shell blender, to insure homogeneity.

If the supplement is used as a top dressing for the feed, it likewise helps to insure uniformity of distribution of the active ingredient(s) across the top of the dressed feed.

For veterinary uses, both paste and pellet formulations may also be conveniently employed. Paste formulations can be prepared readily by dispersing the active compound(s) in a pharmaceutically acceptable oil such as peanut oil, sesame oil, corn oil, and the like. Similarly, pellets containing an effective amount of the compound(s) of the present invention can be prepared by admixing the compound(s) of the invention with a suitable diluent such as carbowax, carnuba wax, and the like, and a lubricant, such as magnesium or calcium stearate, can be employed to improve the pelleting process.

Since one aspect of the present invention relates to the treatment or prevention of Syndrome X with a combination of active ingredients which may be administered separately, the invention also relates to combining separate pharmaceutical compositions in kit form. A kit, according to this invention, comprises two separate pharmaceutical compositions: a first unit dosage form, comprising a therapeutically effective amount of a CRF antagonist and a pharmaceutically acceptable vehicle, carrier or diluent, and a second unit dosage form comprising a therapeutically effective amount of a GR antagonist and a pharmaceutically acceptable vehicle, carrier or diluent. The kit further comprises a container. The container is used to contain the separate compositions and may comprise, for example, a divided bottle or a divided foil packet; however, the separate compositions may also be contained within a single, undivided container. Normally, the kit will also include directions for the administration of the separate components. The kit form is particularly advantageous when the separate components are preferably administered in different dosage forms (e.g., oral and parenteral), are administered at different dosage levels, or when titration of the individual components of the combination is desired by the prescribing physician.

An example of such a kit is a so-called blister pack. Blister packs are well known in the packaging industry and are being used widely for the packaging of pharmaceutical unit dosage forms (tablets, capsules and the like). Blister packs generally consist of a sheet of relatively rigid material covered with a foil of a preferably transparent plastic material. During the packaging process recesses are formed in the plastic foil. The recesses generally conform to the size and shape of the tablets or capsules to be contained therein. Next, the tablets or capsules are placed in the recesses and the sheet of relatively rigid material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules may be removed from the blister pack by the application of manual pressure on the recesses whereby an opening is formed in the sheet at the place of the recess. The tablet or capsule can then be removed through the formed opening.

It is further desirable to provide a memory aid on the pack, e.g., in the form of numbers or similar indicia next to the tablets or capsules whereby the indicia correspond with the days of the regimen which the dosage form so specified is to be ingested. An additional example of such a memory aid is a calendar printed on the pack, e.g., as follows "First Week, Monday, Tuesday, . . . etc . . . Second Week, Monday, Tuesday, . . . " etc. Other variations will be readily apparent. A "daily dose" can be a single tablet or capsule or multiple tablets or capsules to be ingested on a given day. Also, a daily dose of a CRF antagonist can consist of one tablet or capsule while a daily dose of a GR antagonist can consist of multiple tablets or capsules, or vice versa. The memory aid should reflect this.

In another specific embodiment of the invention, a pack designed to dispense the daily doses one at a time in the order of their intended use is provided. Preferably, the pack is equipped with a memory aid, so as to further facilitate compliance with the dosage regimen. An example of such a memory aid is a mechanical counter which indicates the number of daily doses to be dispensed. Another example of such a memory aid is a battery-powered micro-chip memory coupled with a liquid crystal readout, or audible reminder signal which, for example, reads out the date that the last daily dose has been taken and/or reminds the patient when the next dose is to be taken.

The following references disclose animal models, such as the JCR: LA-corpulent (cp) rat or the obese Zucker rat, that may be used to determine the Syndrome X-treating activity of the compound(s) employed to practice the present invention: J. C. Russell et al., Metabolism, Vol. 48, No. 6 (June), 1999: pp 701–706; Diabetes 46:1958–1964, 1997.

Methods that may be used to determine CRF antagonist activity of the compounds employed to practice the present invention are as described in, e.g., Wynn et al., Endocrinology, 116:1653–1659 (1985), and Grigoriadis et al., Peptides, 10:179–188 (1989). Methods that can be used to determine the CRF binding protein inhibiting activity of compounds employed to practice the present invention are described in Brain Research, (1997), 745(1,2), 248–256. These methods determine the binding affinity of a test compound for a CRF receptor, which is highly related to its expected activity as a CRF antagonist.

Methods that may be used to determine GR antagonist activity of the compounds employed to practice the present invention are described below and in commonly assigned International patent application PCT/IB00/00366, filed Mar. 27, 2000, which is hereby incorporated by reference herein. These methods determine the binding affinity of a test compound for a GRA receptor, which is highly related to its expected activity as a GR antagonist.

The following is a description of an assay for the identification of glucocorticoid receptor antagonists/agonists: HeLa cells (American Type Culture Collection (ATCC), Rockville, Md.) containing endogenous human glucocorticoid receptors are transfected with a 3×pLuxF47-GRE-luciferase plasmid generated by standard procedures and a plasmid conferring neomycin resistance. pLuxF47-GRE was constructed by annealing oligonucleotides 23907-26A and 23907-26B and ligating into the Bg I II and Eag I sites of pLuxF47. Novel glucocorticoid responsive cell lines are generated and characterized. One such cell line designated HeLa-GRE9 is used for determining the activity of compounds at the glucocorticoid receptor. Cells are maintained in charcoal-stripped serum and transferred to 96-well microtiter plates one day prior to treatment with various concentrations ($10^{-12}$ to $10^{-5}$) of test compounds in the absence and presence of known glucocorticoid receptor agonists (i.e., dexamethasone, hydrocortisone) for up to 24 hours. Treatments are performed in triplicate. Cell lysates are prepared and luciferase activity is determined using a luminometer. Agonist activity is assessed by comparing the luciferase activity from cells treated with test compound to cells treated with the agonist dexamethasone. Antagonist activity is assessed by comparing the luciferase activity of an $EC_{50}$ concentration of dexamethasone in the absence and presence of test compound. The $EC_{50}$ (concentration that produced 50% of the maximal response) for dexamethasone is calculated from dose response curves.

The following is a description of an assay for determining the competitive inhibition binding of the Human Type II Glucocorticoid receptor expressed in Sf9 cells:

Binding protocol: Compounds are tested in a binding displacement assay using human glucocorticoid receptor expressed in Sf9 cells with $^3$H-dexamethasone as the ligand. Human glucorticoid receptor is expressed in Sf9 cells as described in Mol. Endocrinology 4: 209, 1990. Pellets containing Sf9 cells expressing the human GR receptor from 1 L vats are lysed with 40 ul of 20 mM AEBSF stock (Calbiochem, LaJolla, Calif.) containing 50 mg/ml leupeptin and 40 ml of homogenization buffer is added. The assay is carried out in 96-well polypropylene plates in a final volume of 130 ul containing 200 ug Sf9 lysate protein, 6.9 nM $^3$H-dexamethasone (Amersham, Arlington Heights, Ill.) in presence of test compounds, test compound vehicle (for total counts) or excess dexamethasone (7 uM non-radioactive, to determine non-specific binding) in an appropriate volume of assay buffer. tested at 6 concentrations in duplicate (concentration range 0.1–30 nM or 3–1000 nM). Test compounds are diluted from a 25 mM stock in 100% DMSO with 70% EtOH and added in a volume of 2 µl. Once all additions are made the plates are shaken, sealed with sealing tape and incubated at 4° C. overnight.

After the overnight incubation, unbound counts are removed with dextran coated charcoal as follows: 75 µl of dextran coated charcoal (5.0 g activated charcoal, 0.5 g dextran adjusted to volume of 100 ml with assay buffer) is added, plates are shaken and incubated for five minutes at 4° C. Plates are then centrifuged in a refrigerated benchtop centrifuge at top speed for 15 minutes. 100 µl of the supernatant from each well is placed into a 96-well PET plate with 200 µl of scintillation cocktail and counted on a beta counter (1450 MicroBetaTrilux, from Wallac, Turku, Finland).

Data analysis: After subtracting non-specific binding, counts bound are expressed as % of total counts. The concentration response for test compounds are fitted to a sigmoidal curve to determine the $IC_{50}$ (concentration of compound that displaces 50% of the bound counts).

Reagents: Assay Buffer: 2.0 ml 1M Tris (pH 7.4), 0.2 ml 0.5 mM EDTA (pH 8.0), 77.1 mg DTT, 0.243 g sodium molybdate in a volume of 100 ml water; Homogenization buffer: 2.0 ml 0.5 M $K_2HPO_4$ (pH 7.6), 20 µl 0.5 M EDTA (pH 8.0), 77.1 mg DTT, 0.486 g sodium molybdate in a volume of 100 ml water.

The following is a description of an assay for determining receptor selectivity: T47D cells (American Type Culture Collection (ATCC), Rockville, Md.) containing endogenous human progesterone and mineralocorticoid receptors are transiently transfected with a 3xpLuxF47-GRE-luciferase using Lipofectamine Plus (GIBCO-DRL, Gaithersburg, Md.). Twenty-four hours post-transfection cells are maintained in charcoal-stripped serum and transferred to 96-well microtiter plates. The next day cells are treated with various concentrations ($10^{-12}$ to $10^{-5}$) of test compounds in the absence and presence of a known progesterone receptor agonist (progesterone) and a known mineralocorticoid receptor agonist (aldosterone) for up to 24 hours. Treatments are performed in triplicate. Cell lysates are prepared and luciferase activity is determined using a luminometer. Agonist activity is assessed by comparing the luciferase activity from cells treated with compound alone to cells treated with either the agonist progesterone or aldosterone. Antagonist activity is assessed by comparing the luciferase activity of an $EC_{50}$ concentration of progesterone or aldosterone in the absence and presence of compound. The $EC_{50}$ (concentration that produced 50% of maximal response) for progesterone and aldosterone is calculated from dose response curves.

The following is a description of an assay for determining anti-diabetes and anti-obesity activity. The obese, diabetic ob/ob mouse is used to assess the anti-diabetes and anti-obesity activity of the compounds. Six to 10 week old ob/ob male mice (Jackson Labs, Bar Harbor, Me.) are dosed with test compound(s) for 2 to 10 days. Plasma glucose levels are determined by measuring glucose from samples obtained by orbital bleeding. Glucose is quantitated using an Abbott Autoanalyzer (Abbott, Inc., Abbott Park, Ill.). Food intake is monitored on a daily basis by differential weighing.

The following is a description of an assay for determining the ability of a compound to inhibit glucocorticoid agonist induction of liver tyrosine amino transferase (TAT) activity in conscious rats:

Animals: Male Sprague Dawley rats (from Charles River, Wilimington Mass.) (adrenal-intact or adrenalectomized at least one week prior to the screen) b.w. 90 g are used. The rats are housed under standard conditions for 7–10 d prior to use in the screen.

Experimental protocol: Rats (usually 3 per treatment group) are dosed with test compound, vehicle or positive control (RU486) either i.p., p.o., s.c. or i.v. (tail vein). The dosing vehicle for the test compounds is typically one of the following: 100% PEG 400, 0.25% methyl cellulose in water, 70% ethanol or 0.1 N HCl and the compounds are tested at doses ranging from 10 to 125 mg/kg. The compounds are dosed in a volume of 1.0 ml/100 g body weight (for p.o.) or 0.1 ml/100 g body weight for other routes of administration . Ten minutes after the administration of the test compound, the rats are injected with dexamethasone (0.03 mg/kg i.p. in a volume of 0.1 ml/100 g) or vehicle. To prepare the dexamethasone dosing solution, dexamethasone (from Sigma, St. Louis, Mo.) is dissolved in 100% ethanol and diluted with water (final: 10% ethanol:90% water, vol:vol). Groups treated with vehicle-vehicle, vehicle-dexamethasone, and Ru486-dexamethasone are included in each screen. The compounds are tested vs. dexamethasone only. Three hours after the injection of dexamethasone the rats are sacrificed by decapitation. A sample of liver (0.3 g) is excised and placed in 2.7 ml of ice cold buffer and homogenized with a polytron. To obtain cytosol the liver homogenate is centrifuged at 105,000 g for 60 min and the supernatant is stored at −80° C. until analysis. TAT is assayed on 100 ul of a 1:20 dilution of the 105,000 g supernatant using the methods of D. K. Granner and G. M. Tomkins, "Tyrosine Aminotransferase (Rat Liver)," Methods in Enzymology, 17A: 633–637 (1970) and a reaction time of 8–10 minutes. TAT activity is expressed as umol product/min/g liver.

Interpretation: Treatment data are analyzed by using analysis of variance (ANOVA) with protected least significant difference (PLSD) post-hoc analysis. Compounds are considered active in this test if the TAT activity in the group pretreated with compound prior to dexamethasone administration is significantly (P<0.05) decreased relative to the TAT activity in the group.

What is claimed is:

1. A pharmaceutical composition for treating syndrome X which comprises a therapeutically effective amount of a compound named 5-(1-ethyl-propoxy)-7-methyl-1-(2,6-dimethyl-4-chloro-phenyl)-1,4-dihydro-2H-3-oxa-1,8-diaza-naphthalene and a pharmaceutically acceptable vehicle, carrier or diluent.

2. A method of treating syndrome X in a mammal which comprises administering to said mammal a therapeutically effective amount of a compound named 5-(1-ethyl-propoxy)-7-methyl-1-(2,6-dimethyl-4-chloro-phenyl)-1,4-dihydro-2H-3-oxa-1,8-diaza-naphthalene.

\* \* \* \* \*